:::

United States Patent
Nomura et al.

(10) Patent No.: US 9,418,314 B2
(45) Date of Patent: Aug. 16, 2016

(54) INFORMATION PROCESSING APPARATUS AND CONTROL METHOD AND CONTROL PROGRAM THEREOF, AND COMMUNICATION TERMINAL AND CONTROL METHOD AND CONTROL PROGRAM THEREOF

(71) Applicant: NEC Corporation, Tokyo (JP)

(72) Inventors: Toshiyuki Nomura, Tokyo (JP); Akio Yamada, Tokyo (JP); Kota Iwamoto, Tokyo (JP); Ryota Mase, Tokyo (JP)

(73) Assignee: NEC CORPORATION, Tokyo (JP)

( * ) Notice: Subject to any disclaimer, the term of this patent is extended or adjusted under 35 U.S.C. 154(b) by 36 days.

(21) Appl. No.: 14/375,452

(22) PCT Filed: Jan. 25, 2013

(86) PCT No.: PCT/JP2013/051573
§ 371 (c)(1),
(2) Date: Jul. 30, 2014

(87) PCT Pub. No.: WO2013/115093
PCT Pub. Date: Aug. 8, 2013

(65) Prior Publication Data
US 2015/0003704 A1 Jan. 1, 2015

(30) Foreign Application Priority Data
Jan. 30, 2012 (JP) ................................. 2012-017383

(51) Int. Cl.
*G06K 9/00* (2006.01)
*G06K 9/62* (2006.01)

(52) U.S. Cl.
CPC ............ *G06K 9/6232* (2013.01); *G06K 9/6201* (2013.01)

(58) Field of Classification Search
None
See application file for complete search history.

(56) References Cited

U.S. PATENT DOCUMENTS 6,711,293 B1 3/2004 Lowe
2010/0045423 A1* 2/2010 Glickman ............ G06Q 10/087
340/5.1

(Continued)

FOREIGN PATENT DOCUMENTS

JP 2010-218149 9/2010
JP 2011-008507 1/2011

(Continued)

OTHER PUBLICATIONS

David G. Lowe, Distinctive Image Features from Scale-Invariant key points, International Journal of Computer Vision, 2004, pp. 91 to 110.

(Continued)

*Primary Examiner* — Bhavesh Mehta
*Assistant Examiner* — Oneal R Mistry
(74) *Attorney, Agent, or Firm* — Young & Thompson

(57) ABSTRACT

A medical article and m-number of first local features which are respectively constituted by a feature vector of 1 dimension to i dimensions of m-number of feature points in an image of the medical article are stored in association with each other, n-number of feature points are extracted from an image in a captured video, n-number of second local features respectively constituted by a feature vector of 1 dimension to j dimensions are generated, a smaller number of dimensions among the number of dimensions i and the number of dimensions j is selected, and an existence of the medical article in the image in the video is recognized when it is determined that a prescribed ratio or more of the m-number of first local features up to the selected number of dimensions corresponds to the n-number of second local features up to the selected number of dimensions.

17 Claims, 50 Drawing Sheets

(56) References Cited

U.S. PATENT DOCUMENTS

| | | | |
|---|---|---|---|
| 2010/0054611 A1* | 3/2010 | Nomura | G06K 9/6212 382/224 |
| 2011/0235920 A1* | 9/2011 | Iwamoto | G06K 9/52 382/195 |
| 2013/0113929 A1* | 5/2013 | DeLand | A61B 19/44 348/143 |

FOREIGN PATENT DOCUMENTS

| | | |
|---|---|---|
| JP | 2011-198130 | 10/2011 |
| JP | 2011-221688 | 11/2011 |
| JP | 2011-248757 | 12/2011 |

OTHER PUBLICATIONS

International Search Report PCT/JP2013/051573 dated Mar. 12, 2013.

Hironobu Fujiyoshi, "Gradient-Based Feature Extraction-SIFT and HOG-", IEICE Technical Report, Aug. 27, 2007, vol. 107, No. 206, pp. 211 to 224.

* cited by examiner

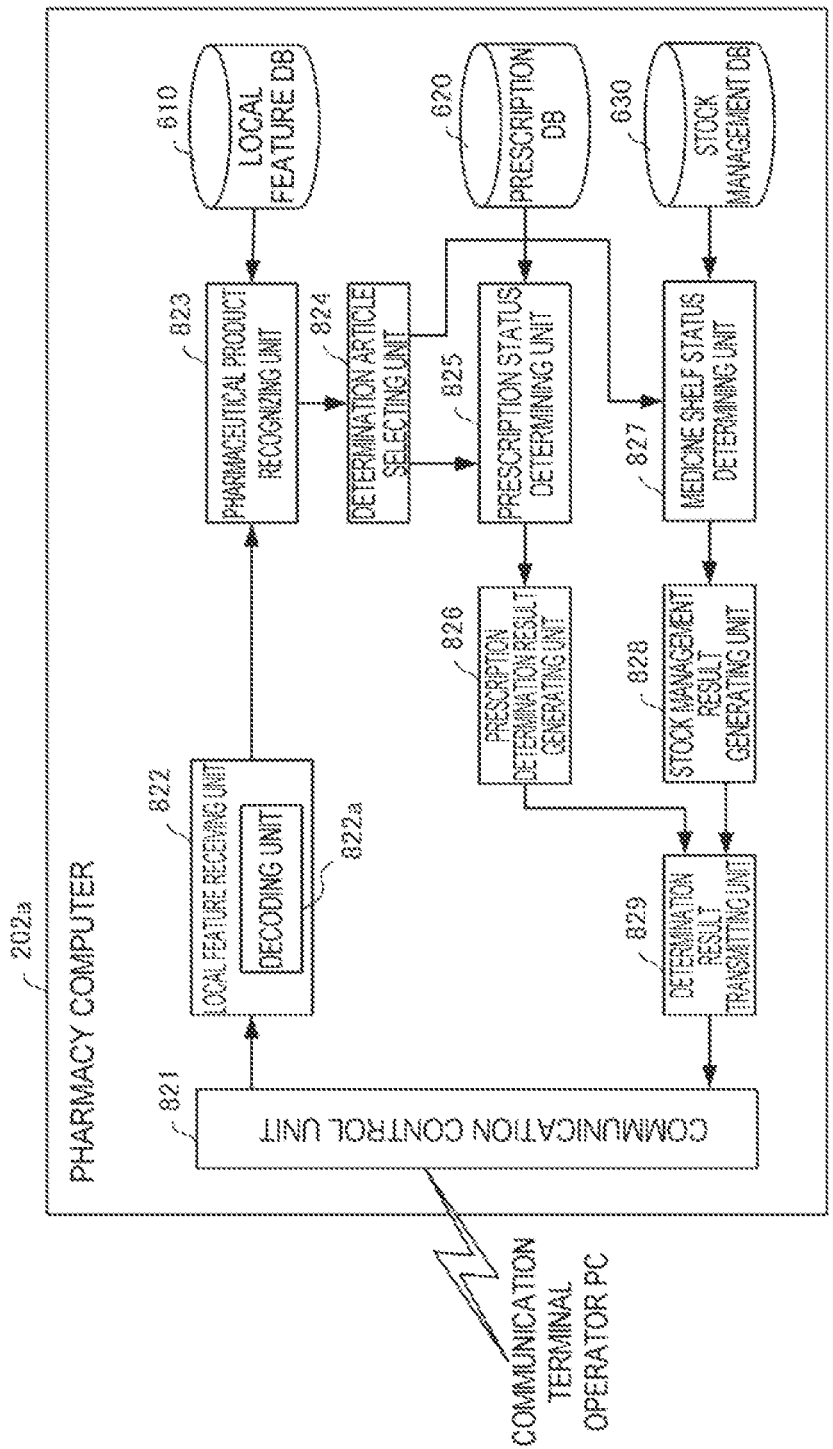

Fig. 9A

| MEDICAL ARTICLE ID/ MEDICAL DEVICE ID/ MEDICAL INSTRUMENT ID | NAME/TYPE | FIRST LOCAL FEATURE | | | SECOND LOCAL FEATURE | ... | m-TH LOCAL FEATURE |
|---|---|---|---|---|---|---|---|
| | | 1ST TO 25TH DIMENSIONS | 26TH TO 50TH DIMENSIONS | ... | 126TH TO 150TH DIMENSIONS | | | |
| 00001 | ELECTROCARDIOGRAM | | | | | | |
| 00002 | SPHYGMOMANOMETER | | | | | | |
| ... | | | | | | | |
| 10001 | SCALPEL | | | | | | |
| 10002 | FORCEPS | | | | | | |
| ... | | | | | | | |

Fig. 9C

| SURGICAL INSTRUMENT ID | NAME/TYPE | MANUFACTURER/ MODEL | SIZE | SHAPE | SURFACE STATE | ... |
|---|---|---|---|---|---|---|
| 00001 | | | | | | |
| 00002 | | | | | | |
| ... | | | | | | |

930 ⎨ (above)

| OPERATION TYPE | 1ST SURGICAL INSTRUMENT ID | | 2ND SURGICAL INSTRUMENT ID | | ... | k-TH SURGICAL INSTRUMENT ID | |
|---|---|---|---|---|---|---|---|
| | TRAY ARRANGEMENT | NUMBER | TRAY ARRANGEMENT | NUMBER | | TRAY ARRANGEMENT | NUMBER |
| ... | | | | | | | |

940 ⎨ (above)

Fig. 10A

| MEDICAL ARTICLE PHARMACEUTICAL PRODUCT ID, MEDICINE SHELF ID | NAME/TYPE | FIRST LOCAL FEATURE | | | SECOND LOCAL FEATURE | ... | m-TH LOCAL FEATURE |
|---|---|---|---|---|---|---|---|
| | | 1ST TO 25TH DIMENSIONS | 26TH TO 50TH DIMENSIONS | 126TH TO 150TH DIMENSIONS | | | |
| ... | | | | | | | |

Fig. 10B

| PATIENT ID (1021) | PATIENT NAME (1022) | DATE/TIME (1023) | PRESCRIPTION (1024) | | |
|---|---|---|---|---|---|
| | | | PHARMACEUTICAL PRODUCT DISPENSER ID | PHARMACEUTICAL PRODUCT DISPENSER ID | ... |
| ... | | | | | |

620

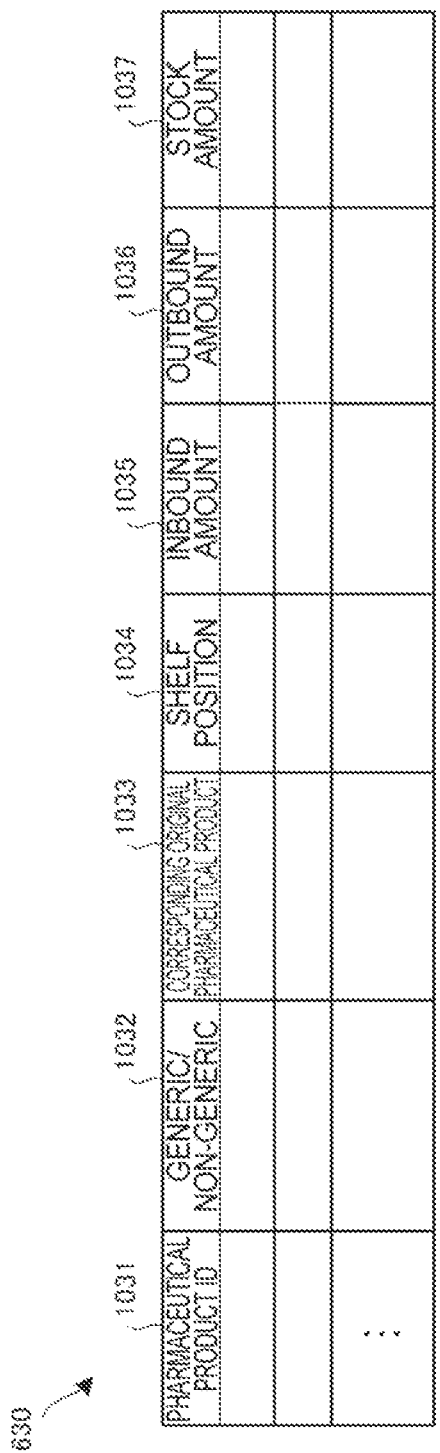

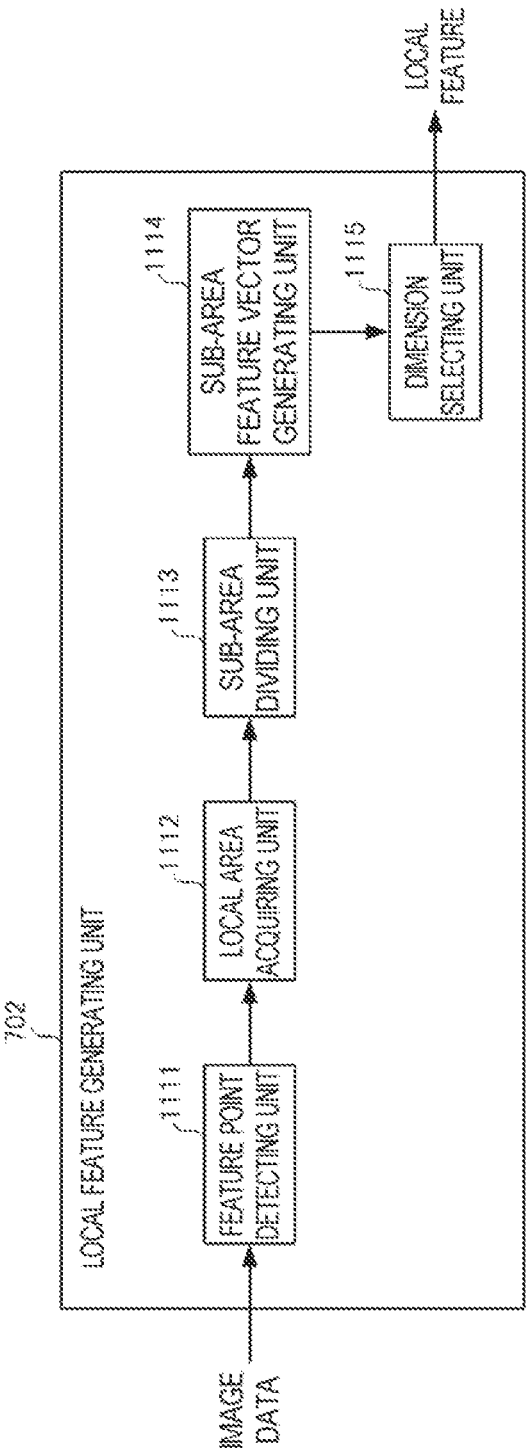

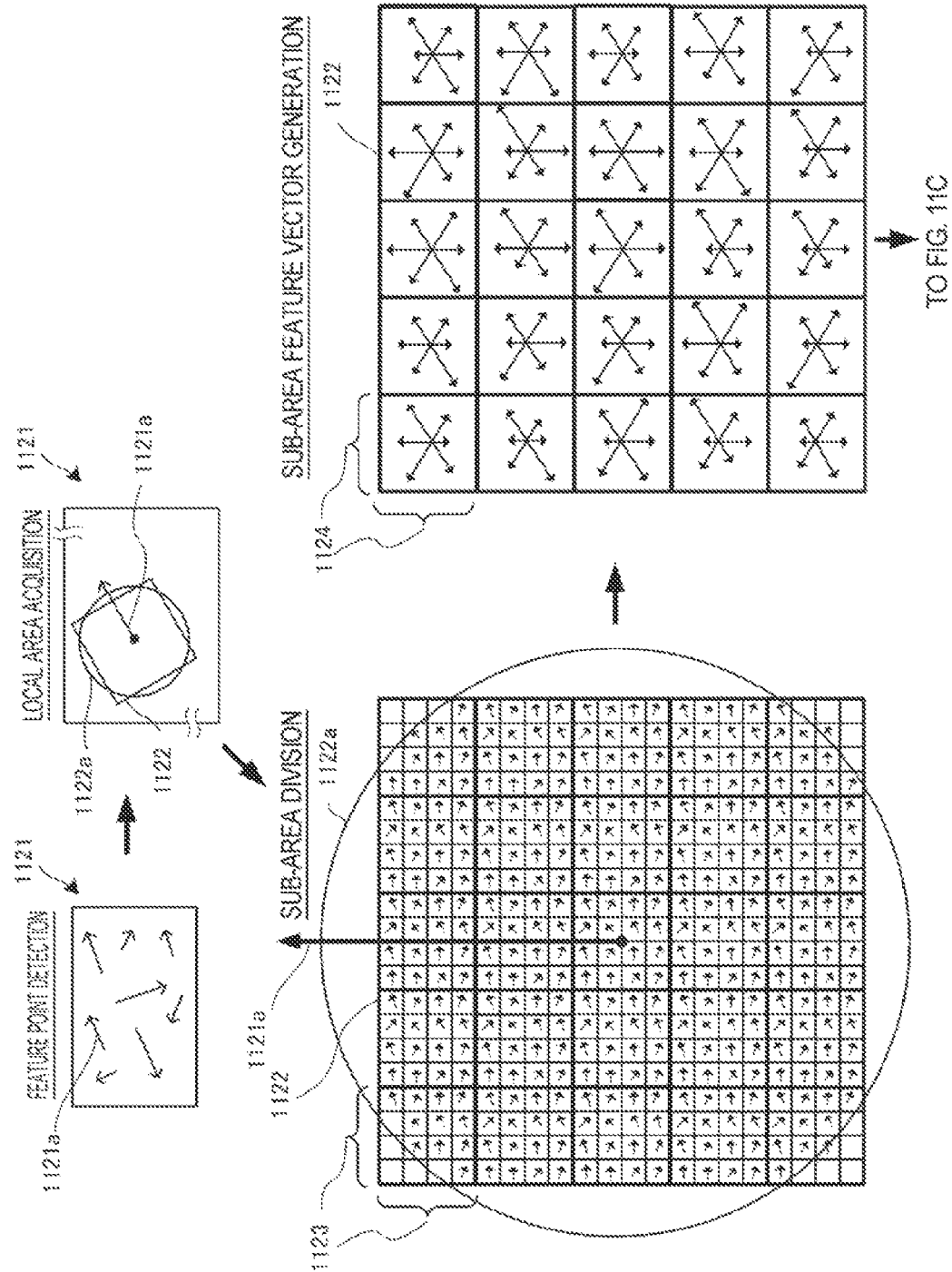

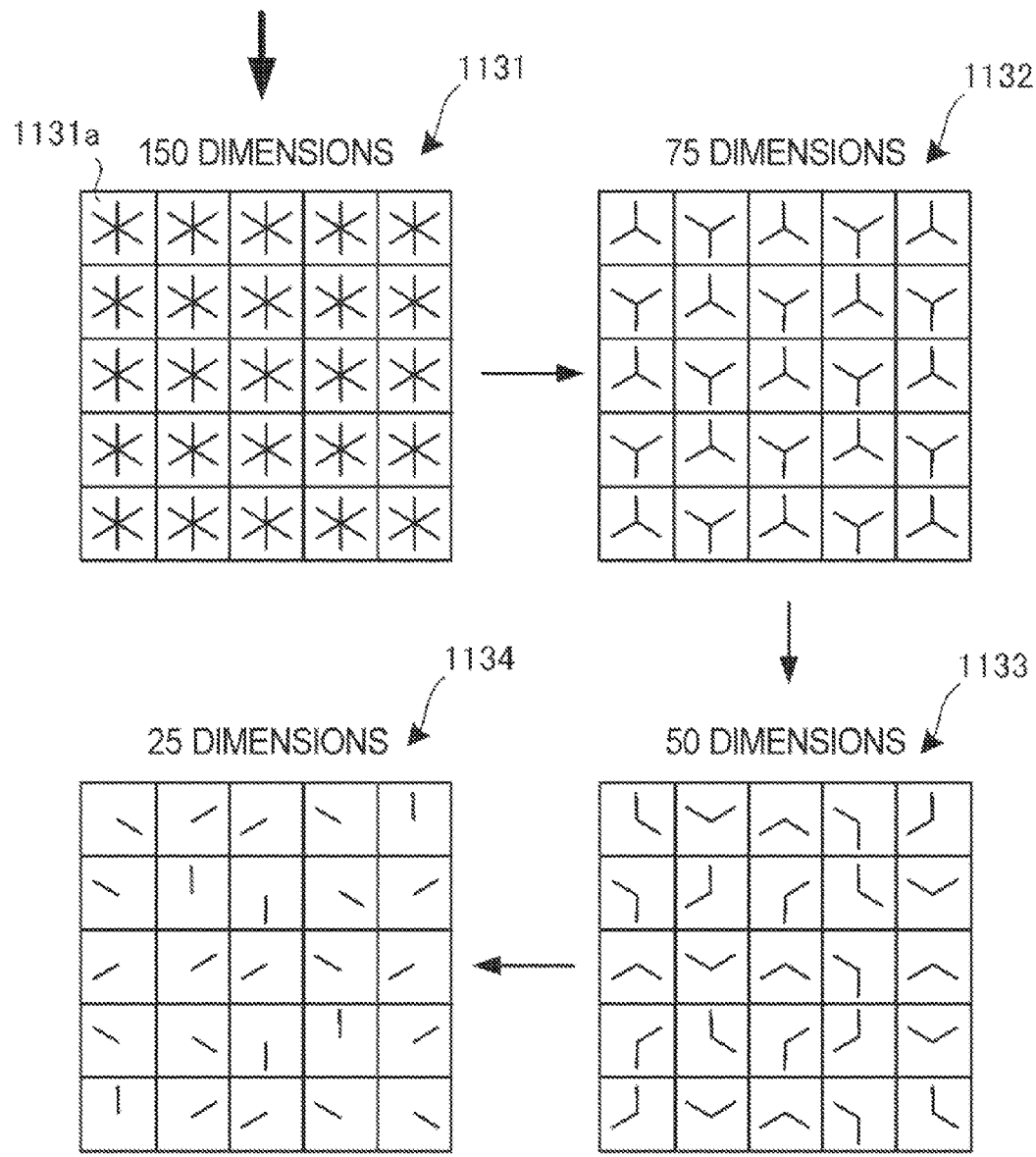

| 22 | 14 | 10 | 18 | 23 |
|----|----|----|----|----|
| 21 | 6  | 2  | 7  | 15 |
| 13 | 5  | 1  | 3  | 11 |
| 17 | 9  | 4  | 8  | 19 |
| 25 | 20 | 12 | 16 | 24 |

1142

| 10 | 18 | 6  | 22 | 11 |
|----|----|----|----|----|
| 25 | 2  | 14 | 3  | 19 |
| 9  | 17 | 1  | 15 | 7  |
| 21 | 5  | 16 | 4  | 23 |
| 13 | 24 | 8  | 20 | 12 |

1143

| 22 | 14 | 10 | 18 | 23 |
|----|----|----|----|----|
| 21 | 6  | 2  | 7  | 15 |
| 13 | 5  | 1  | 3  | 11 |
| 17 | 9  | 4  | 8  | 19 |
| 25 | 20 | 12 | 16 | 24 |

| INPUT IMAGE ID | DETECTED FEATURE POINT | FEATURE POINT COORDINATE | LOCAL AREA INFORMATION | SUB-AREA ID | SUB-AREA INFORMATION | FEATURE VECTOR | SELECTION DIMENSION PRIORITY ORDER | LOCAL FEATURE |
|---|---|---|---|---|---|---|---|---|
| | 001 | | | 001 | | | | |
| | | | | 010 | | | | |
| | 002 | | | 001 | | | | |
| | ... | ... | | ... | | | | |

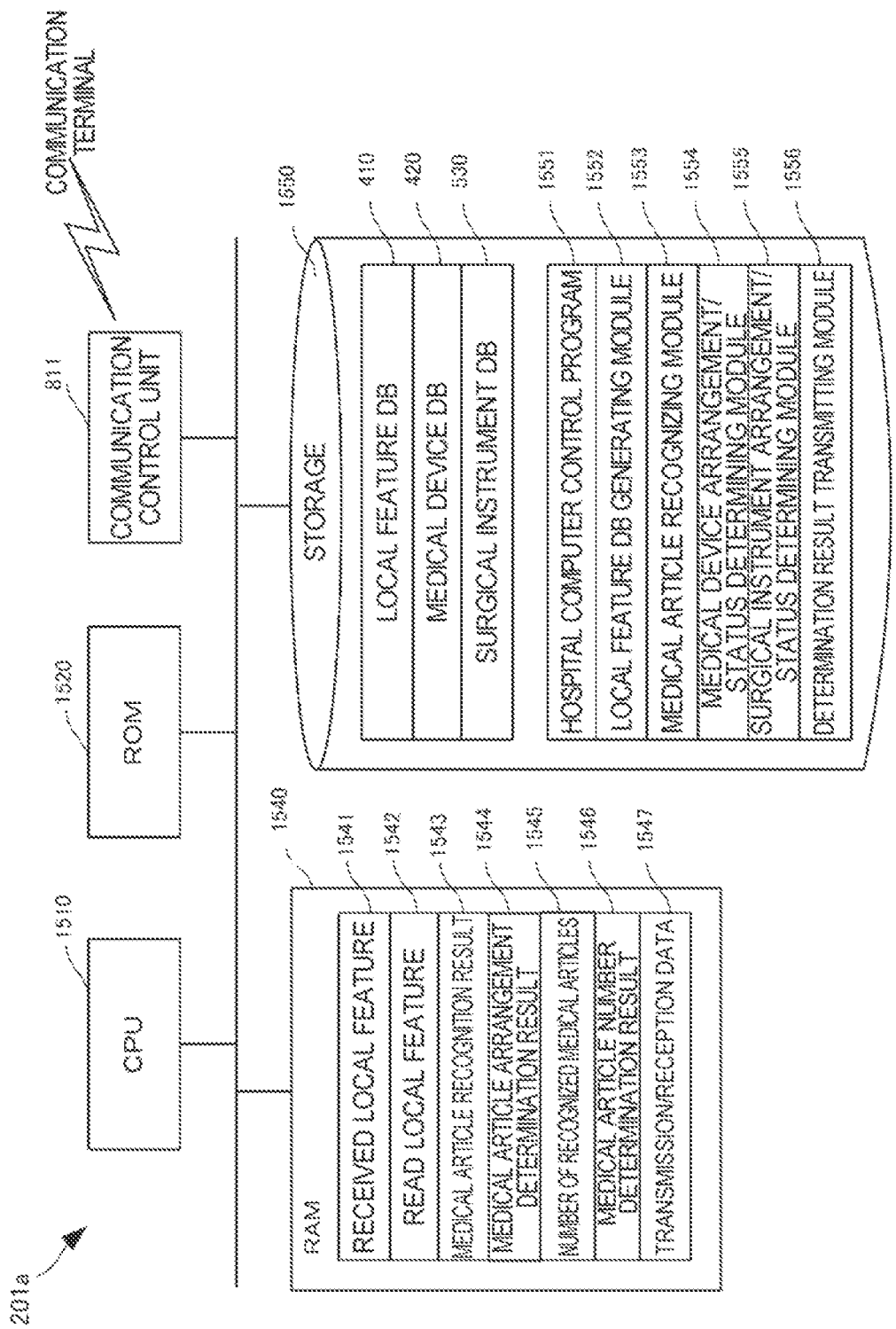

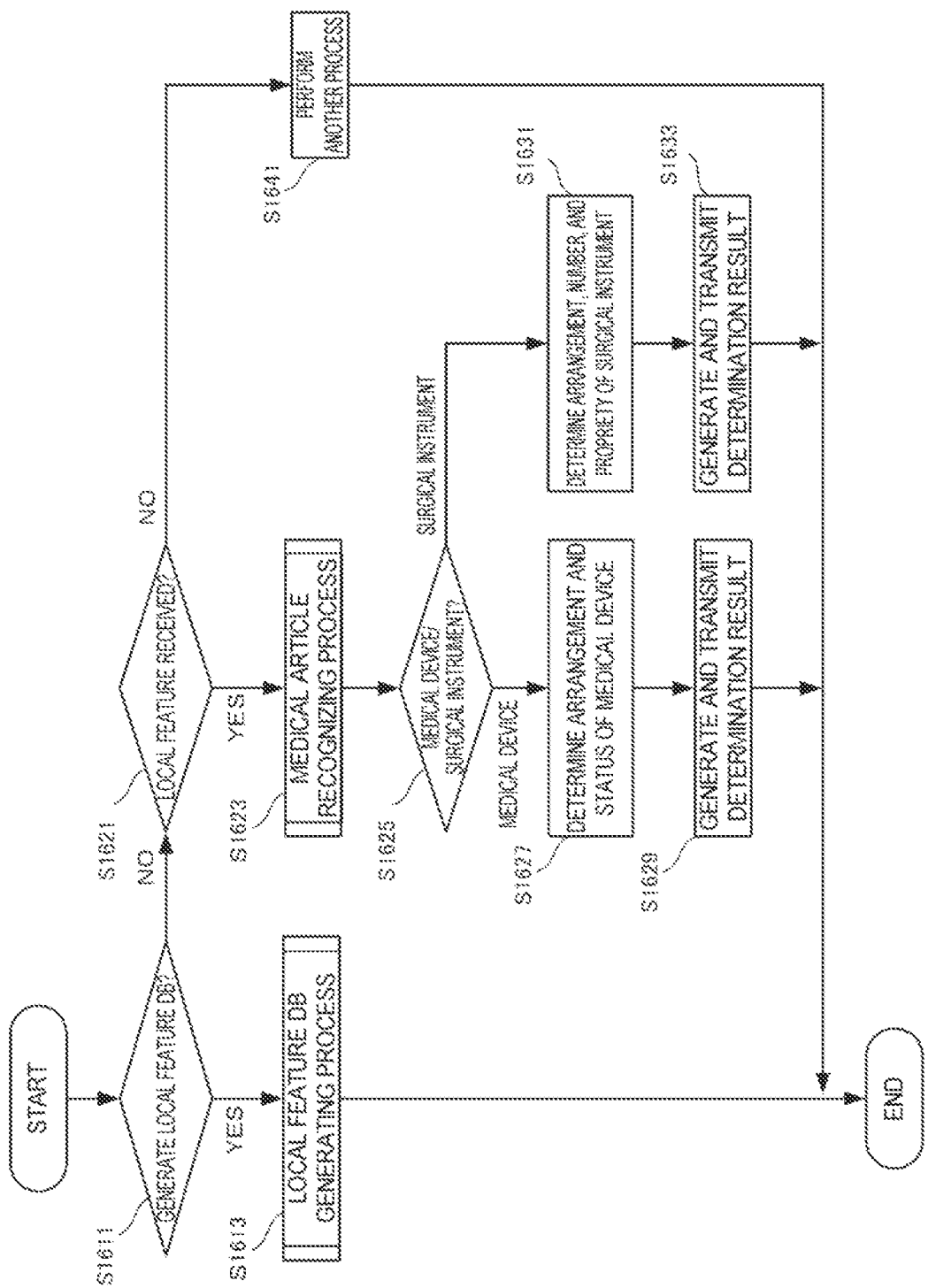

Fig. 28

| MEDICAL ARTICLE ID | NAME/TYPE | FIRST ADJUSTMENT VALUE | | | | SECOND ADJUSTMENT VALUE | ... |
|---|---|---|---|---|---|---|---|
| | | FEATURE POINT PARAMETER | LOCAL AREA PARAMETER | SUB-AREA PARAMETER | FEATURE VECTOR PARAMETER | | |
| | | | | | ... | | |
| ... | | | | | | | |

INFORMATION PROCESSING APPARATUS AND CONTROL METHOD AND CONTROL PROGRAM THEREOF, AND COMMUNICATION TERMINAL AND CONTROL METHOD AND CONTROL PROGRAM THEREOF

BACKGROUND

The present invention relates to a technique for identifying a medical article such as a medical device, a medical instrument, or a pharmaceutical product in a captured video, using a local feature.

In the technical field described above, Patent Document 1 describes a technique for identifying a medical instrument based on a comparison between an input image and a template generated in advance, in terms of a singular point and the number of edges at equal distances from the singular point. In addition, Patent Document 2 describes a technique for improving recognition speed by clustering features when recognizing a query image using a model dictionary generated in advance from a model image.

Patent Document 1: Patent Publication JP-A-2010-218149
Patent Document 2: Patent Publication JP-A-2011-221688

SUMMARY

However, with the techniques described in the documents above, a medical article such as a medical device, a medical instrument, or a pharmaceutical product in an image in a video cannot be recognized in real time.

An object of the present invention is to provide a technique for solving the problem described above.

In order to achieve the object described above, a system according to the present invention includes:

first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article;

second local feature generating unit that extracts n-number of feature points from an image of a video captured by imaging unit, and that generates n-number of second local features respectively constituted by a feature vector of 1 dimension to j dimensions for n-number of local areas including each of the n-number of feature points; and recognizing unit that selects a smaller number of dimensions among the number of dimensions i of the feature vector of the first local feature and the number of dimensions j of the feature vector of the second local feature, and that recognizes that the medical article exists in the image in the video when determining that a prescribed ratio or more of the m-number of first local features constituted by a feature vector up to the selected number of dimensions corresponds to the n-number of second local features constituted by a feature vector up to the selected number of dimensions.

In order to achieve the object described above, a method according to the present invention is an information processing method in an information processing system including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the method including the steps of:

imaging;

extracting n-number of feature points from an image of a video captured in the imaging step and generating n-number of second local features respectively constituted by a feature vector of 1 dimension to j dimensions for n-number of local areas including each of the n-number of feature points; and selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions.

In order to achieve the object described above, an apparatus according to the present invention includes:

second local feature generating unit that extracts n-number of feature points from an image of a video captured by imaging unit, and that generates n-number of second local features respectively constituted by a feature vector of 1 dimension to j dimensions for n-number of local areas including each of the n-number of feature points;

first transmitting unit that transmits the n-number of second local features to an information processing apparatus that recognizes a medical article included in the captured image based on a collation of local features; and first receiving unit that receives information indicating a medical article included in the captured image from the information processing apparatus.

In order to achieve the object described above, a method according to the present invention includes the steps of:

extracting n-number of feature points from an image of a video captured by imaging unit and generating n-number of second local features respectively constituted by a feature vector of 1 dimension to j dimensions for n-number of local areas including each of the n-number of feature points;

transmitting the n-number of second local features to an information processing apparatus that recognizes a medical article included in the captured image based on a collation of local features; and receiving information indicating a medical article included in the captured image from the information processing apparatus.

In order to achieve the object described above, a program according to the present invention causes a computer to execute the steps of:

extracting n-number of feature points from an image of a video captured by imaging unit and generating n-number of second local features respectively constituted by a feature vector of 1 dimension to j dimensions for n-number of local areas including each of the n-number of feature points;

transmitting the n-number of second local features to an information processing apparatus that recognizes a medical article included in the captured image based on a collation of local features; and receiving information indicating a medical article included in the captured image from the information processing apparatus.

In order to achieve the object described above, an apparatus according to the present invention includes:

first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article;

second receiving unit that extracts n-number of feature points from an image of a video captured by a communication terminal and that receives, from the communication terminal, n-number of second local features respectively constituted by a feature vector of 1 dimension to j dimensions for n-number of local areas including each of the n-number of feature points;

recognizing unit that selects a smaller number of dimensions among the number of dimensions i of the feature vector of the first local feature and the number of dimensions j of the feature vector of the second local feature, and that recognizes that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and second transmitting unit that transmits information indicating the recognized medical article to the communication terminal.

In order to achieve the object described above, a method according to the present invention is a control method of an information processing apparatus including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the method including the steps of:

extracting n-number of feature points from an image of a video captured by a communication terminal and receiving, from the communication terminal, n-number of second local features respectively constituted by a feature vector of 1 dimension to j dimensions for n-number of local areas including each of the n-number of feature points;

selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and transmitting information indicating the recognized medical article to the communication terminal.

In order to achieve the object described above, a program according to the present invention is a control program of an information processing apparatus including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the program causing a computer to execute the steps of:

extracting n-number of feature points from an image of a video captured by a communication terminal and receiving, from the communication terminal, n-number of second local features respectively constituted by a feature vector of 1 dimension to j dimensions for n-number of local areas including each of the n-number of feature points;

selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and transmitting information indicating the recognized medical article to the communication terminal.

According to the present invention, a medical article such as a medical device, a medical instrument, or a pharmaceutical product in an image in a video can be recognized in real time.

DESCRIPTION OF DRAWINGS

FIG. 8B is a block diagram showing a functional configuration of a pharmacy computer according to the second embodiment of the present invention;

FIG. 9A is a diagram showing a configuration of a local feature DB of a hospital according to the second embodiment of the present invention;

FIG. 9C is a diagram showing a configuration of a surgical instrument DB according to the second embodiment of the present invention;

FIG. 10A is a diagram showing a configuration of a local feature DB of a pharmacy according to the second embodiment of the present invention;

FIG. 10B is a diagram showing a configuration of a prescription DB according to the second embodiment of the present invention;

FIG. 10C is a diagram showing a configuration of a stock management DB according to the second embodiment of the present invention;

FIG. 11A is a block diagram showing a functional configuration of a local feature generating unit according to the second embodiment of the present invention;

FIG. 11B is a diagram illustrating a procedure of local feature generation according to the second embodiment of the present invention;

FIG. 11C is a diagram illustrating a procedure of local feature generation according to the second embodiment of the present invention;

FIG. 11D is a diagram showing a selection order of sub-areas in a local feature generating unit according to the second embodiment of the present invention;

FIG. 11F is a diagram showing hierarchization of feature vectors in the local feature generating unit according to the second embodiment of the present invention;

FIG. 12B is a diagram showing a local feature generating table of the communication terminal according to the second embodiment of the present invention;

FIG. 15 is a block diagram showing a hardware configuration of a hospital computer according to the second embodiment of the present invention;

FIG. 16 is a flow chart showing a processing procedure of the hospital computer according to the second embodiment of the present invention;

FIG. 28 is a diagram showing a configuration of an accuracy adjustment DB according to the third embodiment of the present invention;

DETAILED DESCRIPTION

Hereinafter, embodiments of the present invention will be illustratively described in detail with reference to the drawings. However, the components described in the following embodiments are merely exemplary and are not intended to limit the technical scope of the present invention thereto.

First Embodiment

An information processing system 100 as a first embodiment of the present invention will be described with reference to FIG. 1. The information processing system 100 is a system that recognizes a medical article in real time. It should be noted that the term "medical article" as used in the present specification includes medical devices, medical instruments, and pharmaceutical products.

Figure 1:
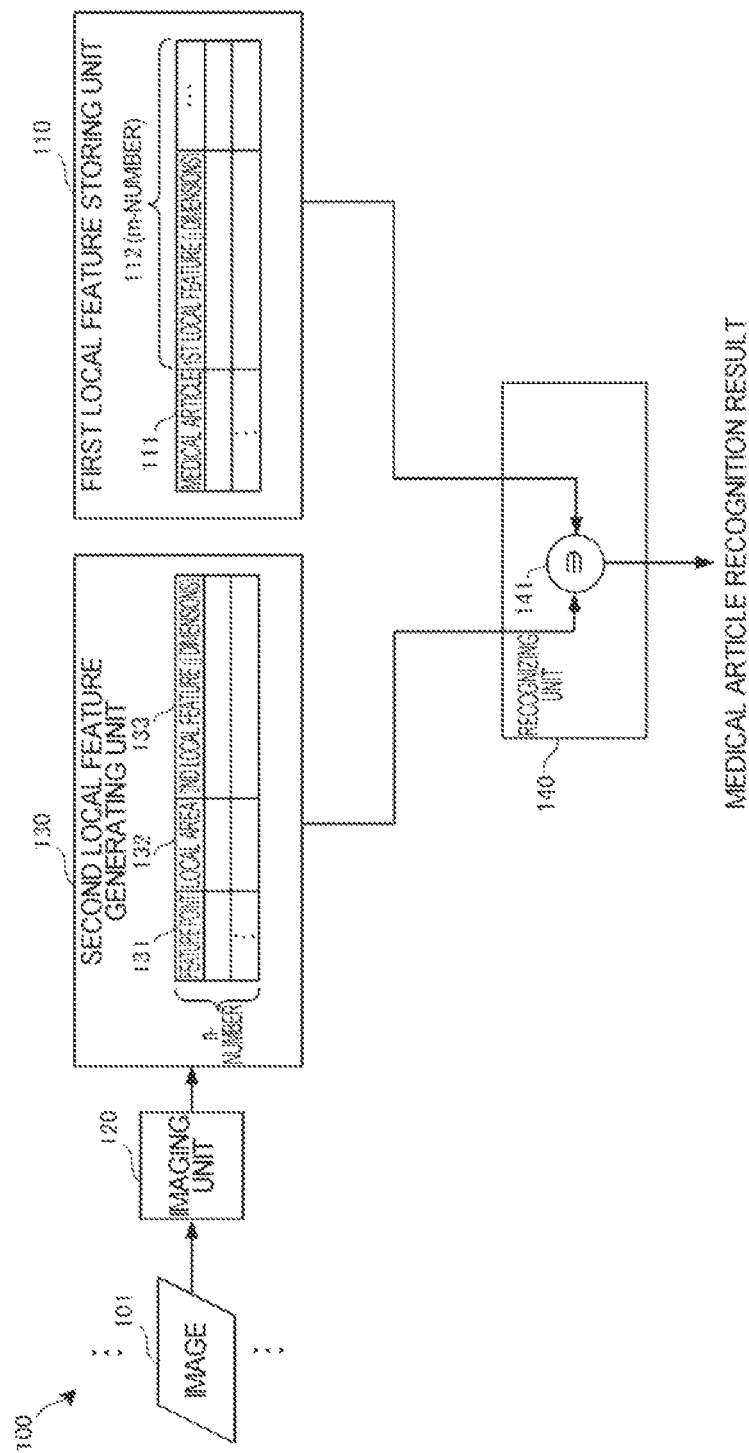
FIG. 1 is a block diagram showing a configuration of an information processing system according to a first embodiment of the present invention.

As shown in FIG. 1, the information processing system 100 includes a first local feature storing unit 110, an imaging unit 120, a second local feature generating unit 130, and a recognizing unit 140. The first local feature storing unit 110 stores, in association with each other, a medical article 111 and m-number of first local features 112 which are respectively constituted by a feature vector of 1 dimension to i dimensions and which are generated for each of m-number of local areas including each of m-number of feature points in an image of the medical article. The second local feature generating unit 130 extracts n-number of feature points 131 from an image 101 in a video captured by the imaging unit 120. In addition, the second local feature generating unit 130 generates n-number of second local features 133 respectively constituted by a feature vector of 1 dimension to j dimensions for n-number of local areas 132 including each of the n-number of feature points. The recognizing unit 140 selects a smaller number of dimensions among the number of dimensions i of a feature vector of the first local feature 112 and the number of dimensions j of a feature vector of the second local feature 133. In addition, the recognizing unit 140 recognizes that the medical article 111 exists in the image 101 in the video when determining (141) that a prescribed ratio or more of the m-number of first local features 112 constituted by feature vectors up to the selected number of dimensions corresponds to the n-number of second local features 133 constituted by feature vectors up to the selected number of dimensions.

According to the present embodiment, a medical article such as a medical device, a medical instrument, or a pharmaceutical product in an image in a video can be recognized in real time.

Second Embodiment

Next, an information processing system according to a second embodiment of the present invention will be described. In the present embodiment, a configuration in which a medical article is recognized and managed at each department in a hospital or a pharmacy will be comprehensively shown.

According to the present embodiment, a medical article such as a medical device, a medical instrument, or a pharmaceutical product in an image in a video can be recognized and managed in real time.

Configuration of Information Processing System

Figure 2:
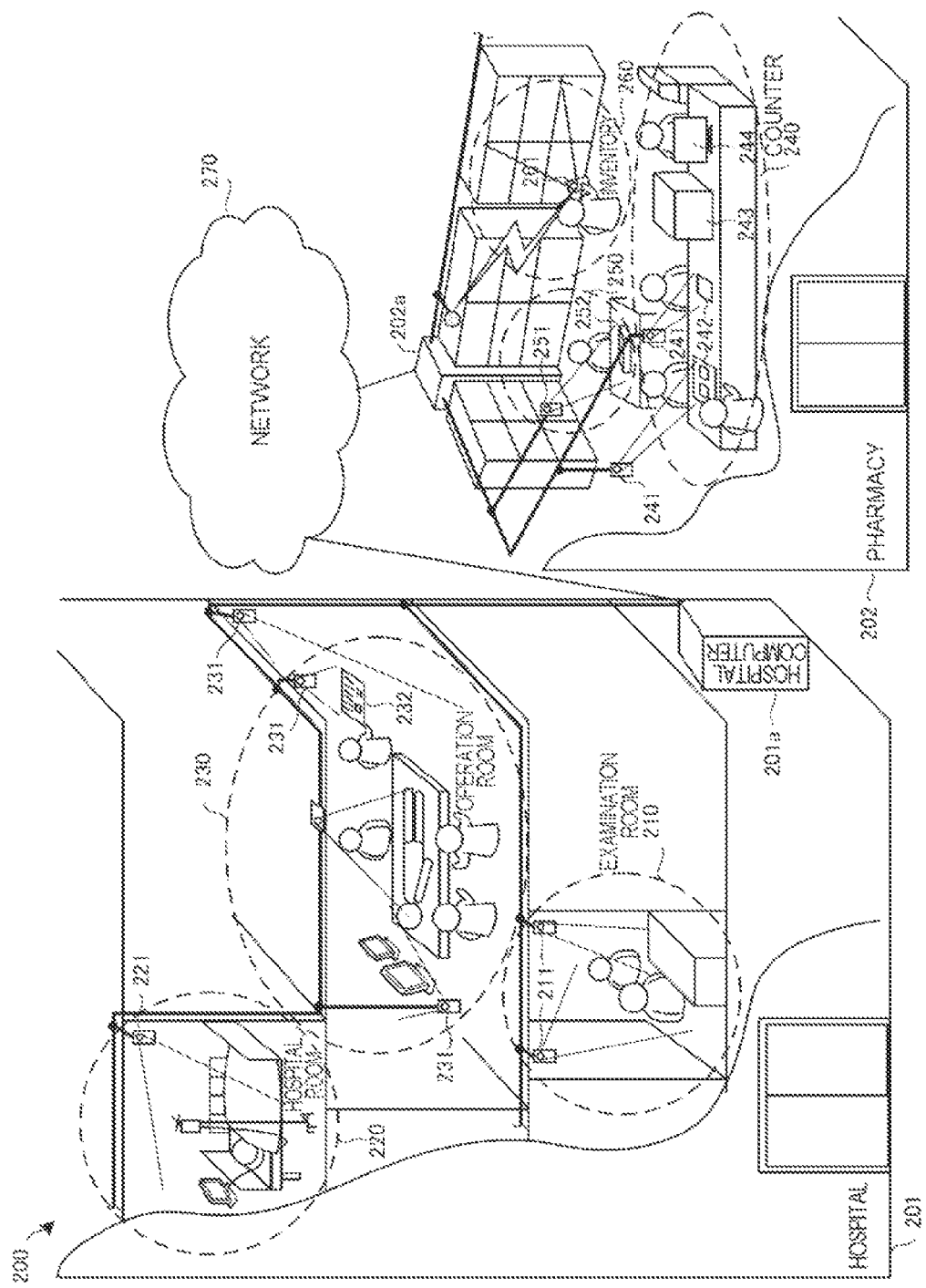
FIG. 2 is a block diagram showing a configuration of an information processing system according to a second embodiment of the present invention.

FIG. 2 is a block diagram showing a configuration of an information processing system 200 according to the present embodiment.

The information processing system 200 shown in FIG. 2 is a system that recognizes and manages a medical article such as a medical device, a medical instrument, or a pharmaceutical product. The information processing system 200 includes a hospital 201 and a pharmacy 202. A hospital computer 201a that is installed at the hospital 201 and a pharmacy computer 202a that is installed at the pharmacy 202 are connected to each other via a network 270. The hospital computer 201a and the pharmacy computer 202a communicate prescription data to one another. Alternatively, in a case where a pharmacy is located inside the hospital 201, the hospital computer 201a may comprehensively control the pharmacy.

With respect to the hospital 201 shown in FIG. 2, an examination room process 210, a hospital room process 220, and an operation room process 230 will be described.

First, in the examination room process 210, a communication terminal 211 captures a video of the examination room or a desktop and generates a local feature from the video. In the present example, the generated local feature is sent to the hospital computer 201a. The hospital computer 201a identifies a medical device or a medical instrument in the examination room or on the desktop from the local feature. Subsequently, the hospital computer 201a determines an arrangement of the medical device or the medical instrument or determines a status regarding whether the medical device or the medical instrument is normal or not. If the communication terminal 211 is a mobile terminal, a determination result may be informed to the communication terminal 211. In addition, monitoring is performed by a doctor or a nurse through a center PC (Personal Computer) (not shown). Furthermore, a medical record on a desk may be recognized.

Next, in the hospital room process 220, a communication terminal 221 captures a video of the hospital room and generates a local feature from the video. The generated local feature is sent to the hospital computer 201a. The hospital computer 201a identifies a medical device or a medical instrument in the hospital room from the local feature. Subsequently, the hospital computer 201a determines an arrangement of the medical device or the medical instrument or determines a status regarding whether the medical device or the medical instrument is normal or not. If the communication terminal 221 is a mobile terminal, a determination result may be informed to the communication terminal 221. In addition, monitoring is performed by a doctor or a nurse through a center PC (not shown). Moreover, medical devices or medical instruments may include a thermometer and drip infusion equipment.

Next, in the operation room process 230, a communication terminal 231 captures a video of the operation room, a surgical instrument tray 232, a patient, or medical devices. A local feature is generated from the captured video. The generated local feature is sent to the hospital computer 201a. The hospital computer 201a identifies a medical device or a medical instrument in the operation room from the local feature. Subsequently, the hospital computer 201a determines an arrangement of the medical device or the medical instrument or determines a status regarding whether the medical device or the medical instrument is normal or not. In particular, an arrangement of a surgical instrument on the surgical instrument tray 232 or a status regarding whether the surgical instrument is normal or not is determined from the video of the surgical instrument tray 232. If the communication terminal 231 is a mobile terminal, a determination result may be informed to the communication terminal 231. In addition, monitoring is performed by a doctor or a nurse through a center PC (not shown).

With respect to the pharmacy 202 shown in FIG. 2, a counter process 240, a process 250 with respect to a medicine tray 252, and an inventory process 260 at a medicine shelf will be described.

In the counter process 240, a communication terminal 241 carried by an employee or installed at the counter captures a video of a medicine bag 242 or a medicine basket. A local feature is generated from the captured video. The generated local feature is sent to the pharmacy computer 202a. The pharmacy computer 202a identifies a medicine bag or a pharmaceutical product at the counter from the local feature. Subsequently, the pharmacy computer 202a determines whether a type or the number of pharmaceutical products corresponds to a prescription read by a prescription reader 243 or whether the pharmaceutical product itself is normal or not. If the communication terminal 241 is a mobile terminal, a determination result may be informed to the communication terminal 241. In addition, an operator performs monitoring through an operator PC 244.

In the process 250 with respect to the medicine tray 252, a video of the medicine tray 252 is captured. A local feature is generated from the captured video. The generated local feature is sent to the pharmacy computer 202a. The pharmacy computer 202a identifies a pharmaceutical product in the medicine tray 252 from the local feature. Subsequently, the pharmacy computer 202a determines whether a type or the number of pharmaceutical products corresponds to a prescription read by a prescription reader 243 or whether the pharmaceutical product itself is normal or not. A determination result is informed by the communication terminal 241.

Moreover, in a case of recognizing individual medicine bags and a plurality of pharmaceutical products in a basket, control may be performed so as to generate local features of different accuracies.

Next, in the inventory process 260, a video of a desired shelf is captured by a communication terminal 261 carried by an employee. A local feature is generated from the captured video. The generated local feature is sent to the pharmacy computer 202a. Moreover, with the inventory process 260, since each pharmaceutical product displayed on the shelf must be recognized in addition to simply recognizing the shelf, local feature generation is performed based on the number of feature points or the number of dimensions of a feature vector at a higher accuracy as compared to the counter process 240 and the medicine tray process 250 (refer to FIGS. 11A to 11F).

As described above, the examination room process 210, the hospital room process 220, the operation room process 230, the counter process 240, the medicine tray process 250, and the pharmaceutical product inventory process 260 can be realized in real time by simply capturing videos using the communication terminals 211 to 261.

Display Screen Example of Communication Terminal

Figure 3:
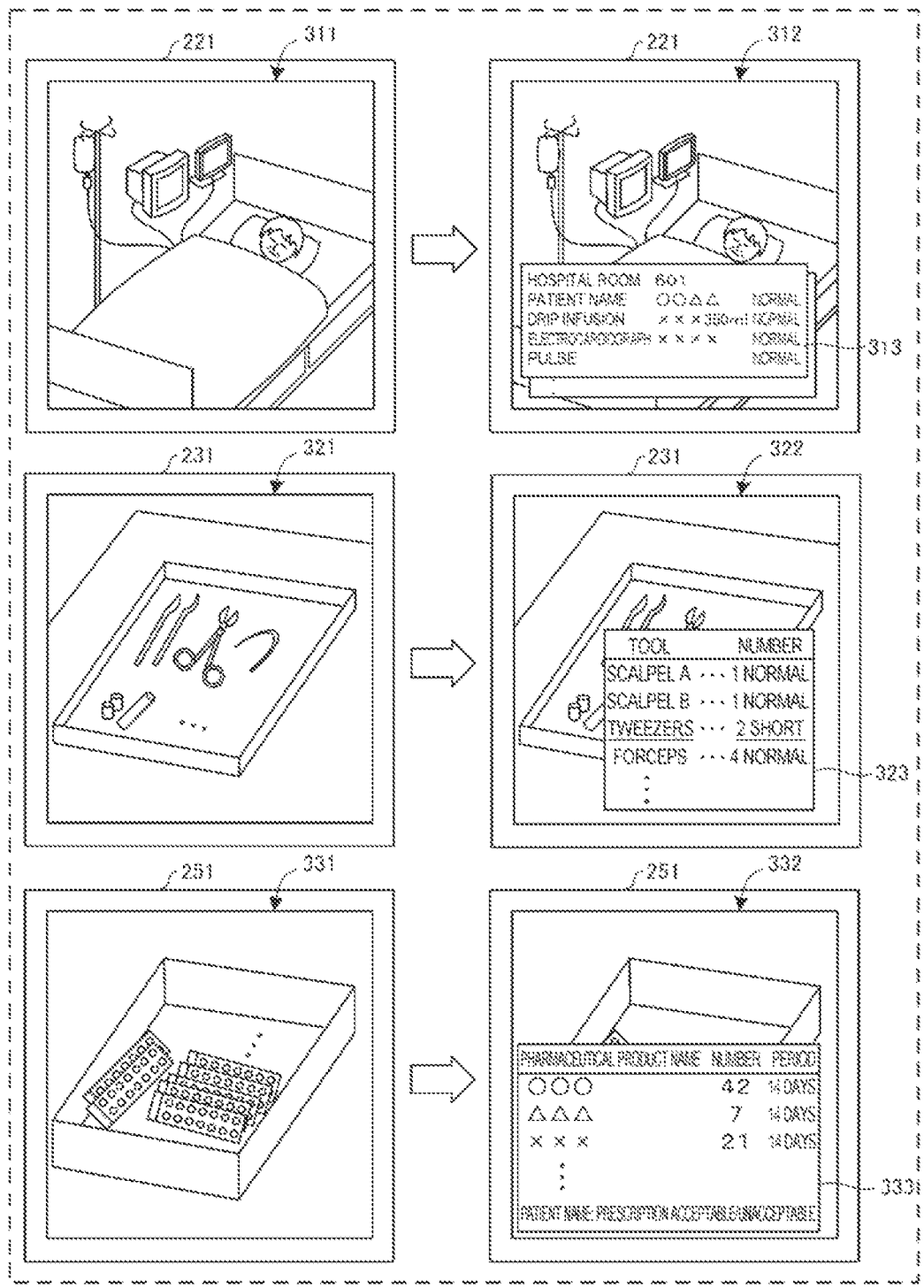
FIG. 3 is a diagram showing a display screen example of a communication terminal according to the second embodiment of the present invention.

FIG. 3 is a diagram showing display screen examples of the communication terminals 221, 231, and 251 according to the present embodiment. Moreover, while the hospital room communication terminal 221, the operation room communication terminal 231, and the medicine tray communication terminal 251 are shown in FIG. 3, similar descriptions may apply to other communication terminals.

An upper part of FIG. 3 represents a display screen of the communication terminal 221 in a hospital room. A local feature is generated from a video screen 311 shown in a left diagram and is collated with a local feature generated in advance from each medical device. In addition, a status of each medical device in a recognition result is determined and a screen 312 on which a status 313 is superimposed on the video screen is displayed as shown in a right diagram. The screen 312 may be displayed on a center PC.

A middle part of FIG. 3 represents a display screen of a video of a surgical instrument tray captured by the communication terminal 231 in an operation room. A local feature is generated from a video screen 321 shown in a left diagram and is collated with a local feature generated in advance from each medical instrument. In addition, the number, an arrangement, and a status of each medical instrument in a recognition result are determined and a screen 322 on which a status 323 is superimposed on the video screen is displayed as shown in a right diagram. The screen 322 may be displayed on a center PC.

A lower part of FIG. 3 represents a display screen of a video of a medicine tray captured by the communication terminal 251 in the pharmacy. A local feature is generated from a video screen 331 shown in a left diagram and is collated with a local feature generated in advance from each pharmaceutical product. In addition, the number and a status of each pharmaceutical product in a recognition result are determined and compared with a prescription, and a screen 332 on which a status 333 is superimposed on the video screen is displayed as shown in a right diagram. The screen 332 may be displayed on an operator PC.

Operational Procedure of Information Processing System

An operational procedure applied to each department in the information processing system 200 according to the present embodiment will be described with reference to FIGS. 4 to 6.

Operational Procedure in Hospital Room

Figure 4:
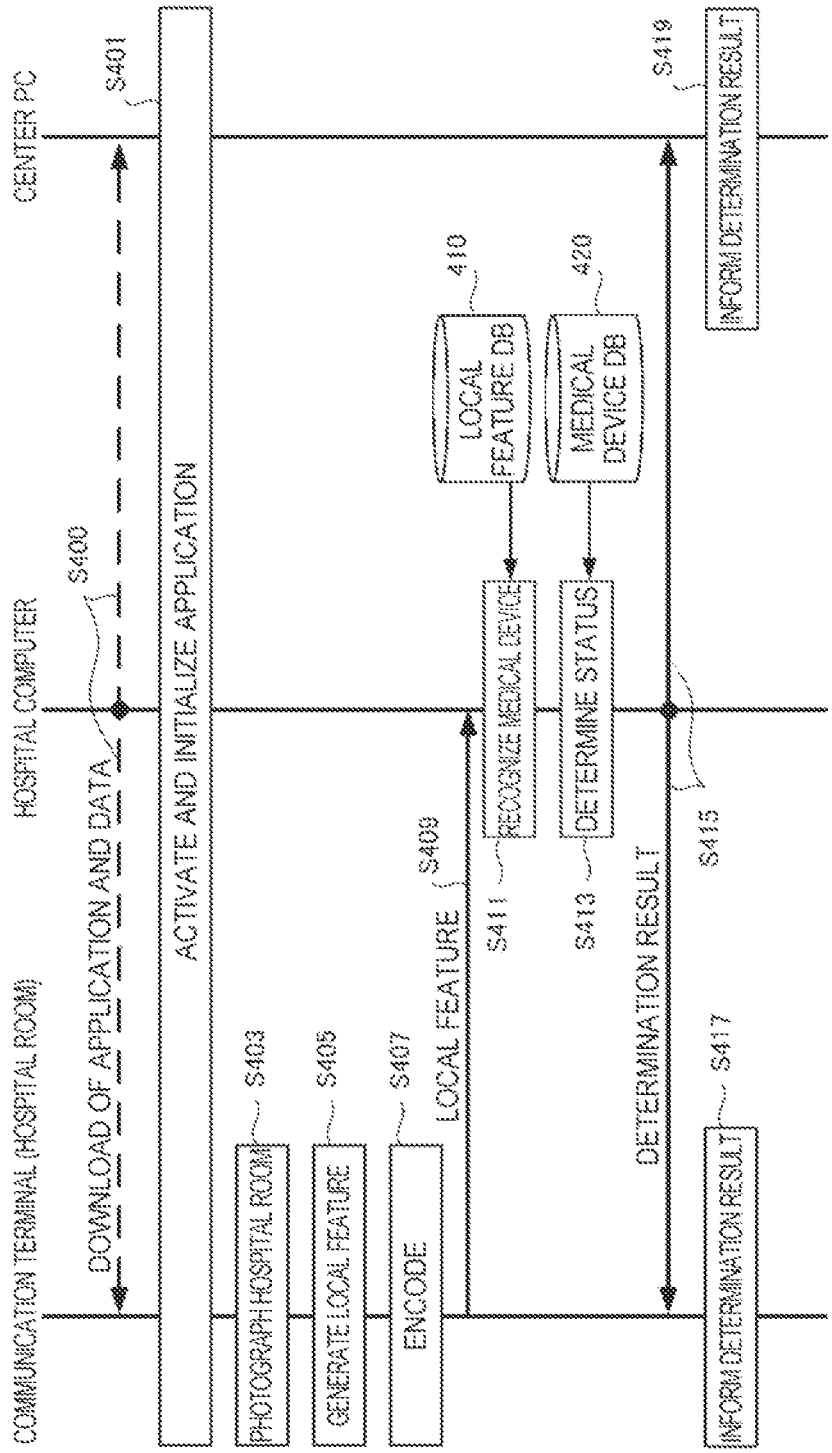
FIG. 4 is a sequence diagram showing an operational procedure in a hospital room of the information processing system according to the second embodiment of the present invention.

FIG. 4 is a sequence diagram showing an operational procedure in a hospital room of the information processing system 200 according to the present embodiment.

First, if necessary, in step S400, an application and/or data is downloaded from the hospital computer 201a to the communication terminal 221 or a center PC. In addition, in step S401, the application is activated and initialized in order to perform processes of the present embodiment.

In step S403, the communication terminal photographs the hospital room. In step S405, a local feature is generated from a video of the hospital room. Subsequently, in step S407, the local feature is encoded together with a feature point coordinate. The encoded local feature is transmitted in step S409 from the communication terminal to the hospital computer 201a.

In step S411, the hospital computer 201a references a local feature DB 410 generated and stored with respect to each medical device that is a medical article and performs recognition of a medical device. Subsequently, in step S413, the hospital computer 201a references a medical device DB 420 that stores a normal status of the medical device and determines a status of the medical device. In step S415, a status determination result is transmitted from the hospital computer 201a to a communication terminal and a center PC.

The communication terminal informs the received determination result in step S417 and the center PC informs the received determination result in step S419.

Operational Procedure in Operation Room

Figure 5:
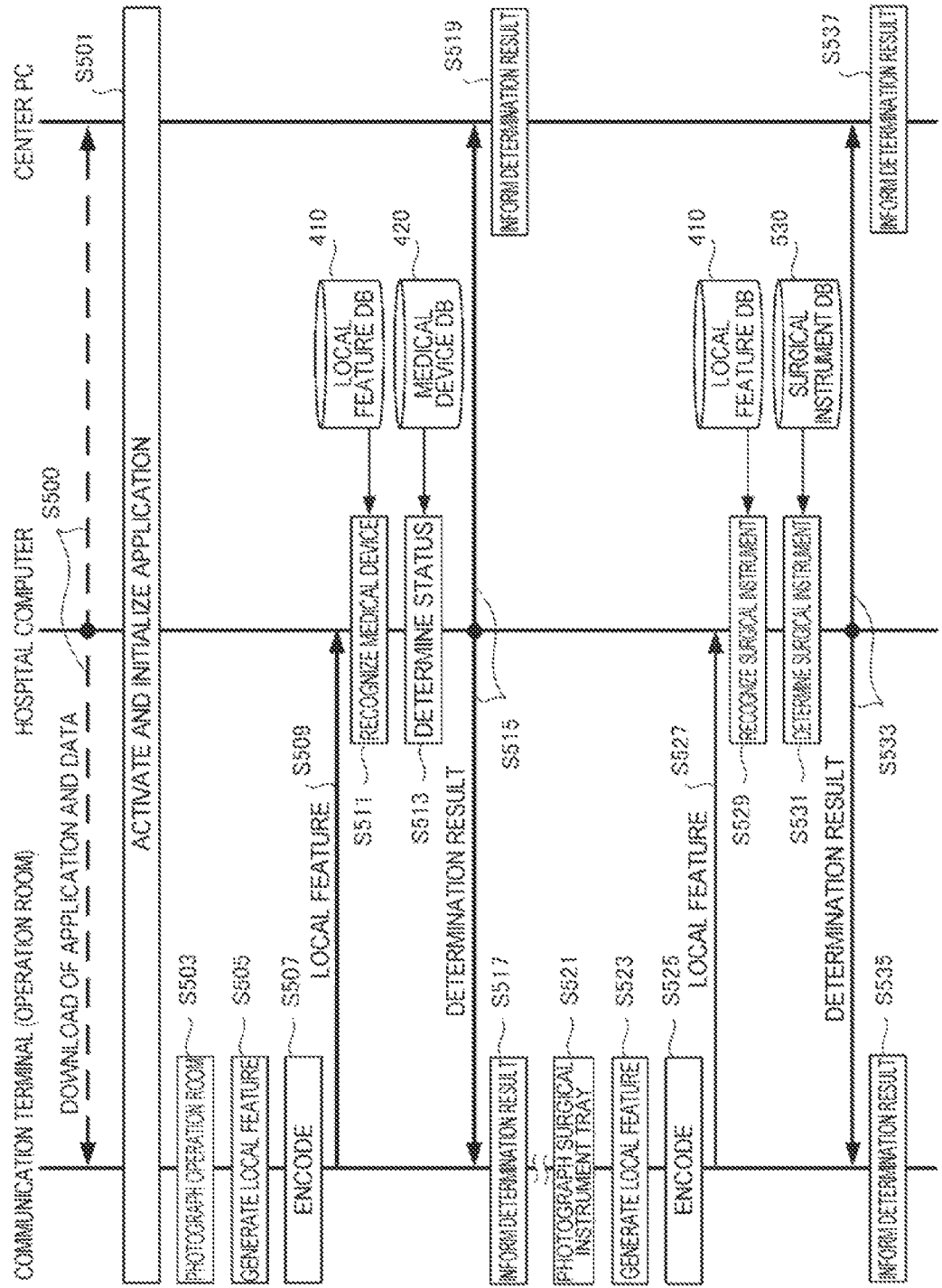
FIG. 5 is a sequence diagram showing an operational procedure in an operation room of the information processing system according to the second embodiment of the present invention.

FIG. 5 is a sequence diagram showing an operational procedure in an operation room of the information processing system 200 according to the present embodiment.

First, if necessary, in step S500, an application and/or data is downloaded from the hospital computer 201a to the communication terminal 231 or a center PC. In addition, in step S501, the application is activated and initialized in order to perform processes of the present embodiment.

In step S503, the communication terminal photographs the operation room. In step S505, a local feature is generated from a video of the operation room. Subsequently, in step S507, the local feature is encoded together with a feature point coordinate. The encoded local feature is transmitted in step S509 from the communication terminal to the hospital computer 201a.

In step S511, the hospital computer 201a references a local feature DB 410 generated and stored with respect to each medical device that is a medical article and performs recognition of a medical device. Subsequently, in step S513, the hospital computer 201a references a medical device DB 420 that stores a normal status of the medical device and determines a status of the medical device. In step S515, a status determination result is transmitted from the hospital computer 201a to a communication terminal and a center PC.

The communication terminal informs the received determination result in step S517 and the center PC informs the received determination result in step S519.

In addition, in step S521, the communication terminal photographs a surgical instrument tray. In step S523, a local feature is generated from a video of the surgical instrument tray. Subsequently, in step S525, the local feature is encoded together with a feature point coordinate. The encoded local feature is transmitted in step S527 from the communication terminal to the hospital computer 201a.

In step S529, the hospital computer 201a references a local feature DB 410 generated and stored with respect to each surgical instrument that is a medical article and performs recognition of a surgical instrument. Subsequently, in step S531, the hospital computer 201a references a surgical instrument DB 530 that stores a normal status of the surgical instrument and determines a status such as a mistake or a defect of the surgical instrument. In step S533, a status determination result is transmitted from the hospital computer 201a to a communication terminal and a center PC.

The communication terminal informs the received determination result in step S535 and the center PC informs the received determination result in step S537.

Operational Procedure in Pharmacy

Figure 6:
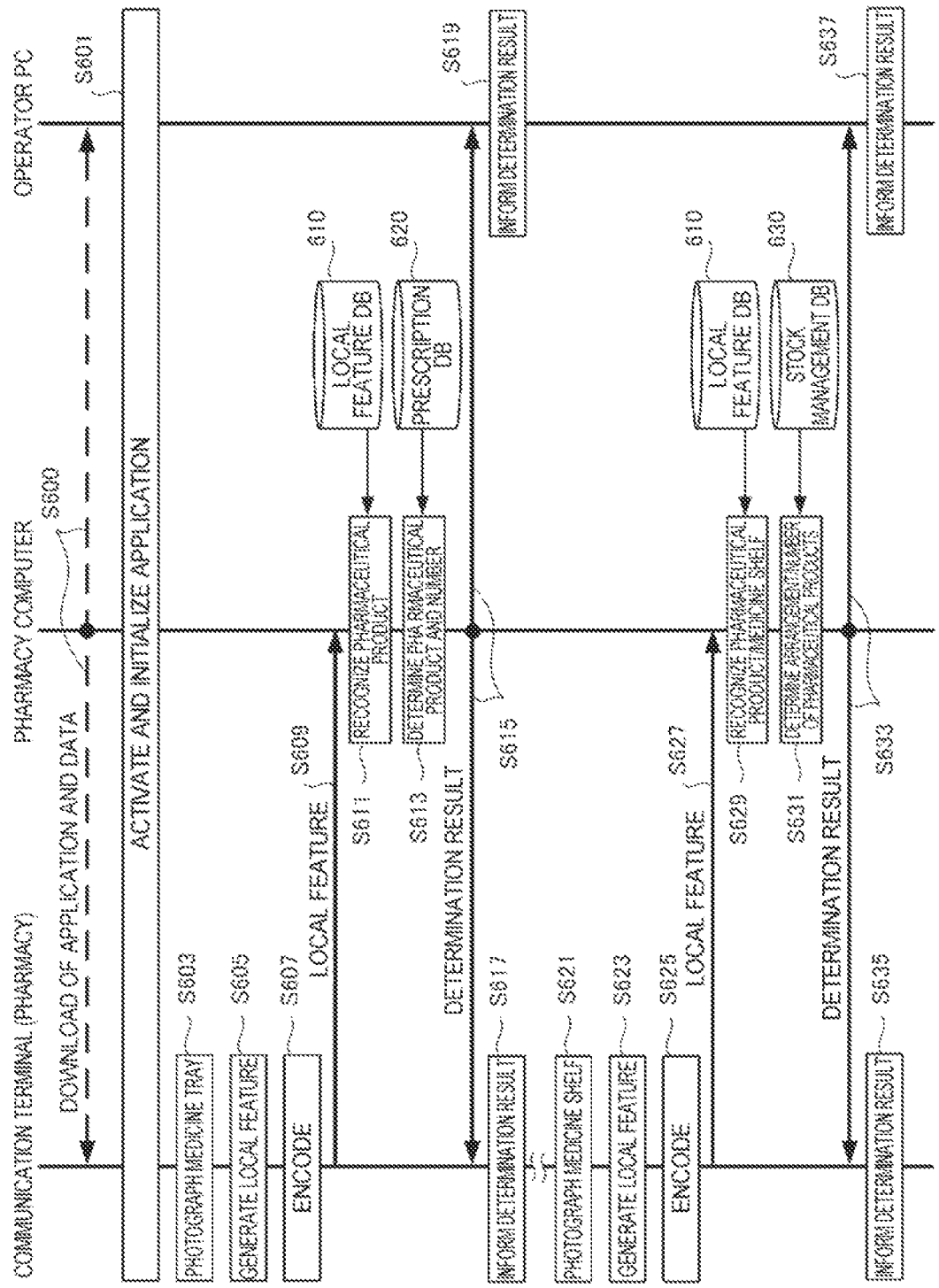
FIG. 6 is a sequence diagram showing an operational procedure in a pharmacy of the information processing system according to the second embodiment of the present invention.

FIG. 6 is a sequence diagram showing an operational procedure in the pharmacy of the information processing system 200 according to the present embodiment.

First, if necessary, in step S600, an application and/or data is downloaded from the pharmacy computer 202a to the communication terminal 251 or an operator PC. In addition, in step S601, the application is activated and initialized in order to perform processes of the present embodiment.

In step S603, the communication terminal photographs a medicine tray. In step S605, a local feature is generated from a video of the medicine tray. Subsequently, in step S607, the local feature is encoded together with a feature point coordinate. The encoded local feature is transmitted in step S609 from the communication terminal to the pharmacy computer 202a.

In step S611, the pharmacy computer 202a references a local feature DB 610 generated and stored with respect to each pharmaceutical product that is a medical article and performs recognition of a pharmaceutical product. Subsequently, in step S613, the pharmacy computer 202a references a prescription DB 620 that stores pharmaceutical products and the number of pharmaceutical products and determines a status of the pharmaceutical product. In step S615, a status determination result is transmitted from the pharmacy computer 202a to a communication terminal and an operator PC.

The communication terminal informs the received determination result in step S617 and the operator PC informs the received determination result in step S619.

In addition, in step S621, the communication terminal photographs a medicine shelf. In step S623, a local feature is generated from a video of the medicine shelf. Subsequently, in step S625, the local feature is encoded together with a feature point coordinate. The encoded local feature is transmitted in step S627 from the communication terminal to the pharmacy computer 202a.

In step S629, the pharmacy computer 202a references a local feature DB 610 generated and stored with respect to each pharmaceutical product that is a medical article and performs recognition of a medicine shelf and a pharmaceutical product. Subsequently, in step S631, the pharmacy computer 202a references a stock management DB 630 that stores stock of pharmaceutical products and determines an arrangement and the number of pharmaceutical products in the medicine shelf. In step S633, a determination result is transmitted from the pharmacy computer 202a to a communication terminal and an operator PC.

The communication terminal informs the received determination result in step S635 and the operator PC informs the received determination result in step S637.

Functional Configuration of Communication Terminal

Figure 7:
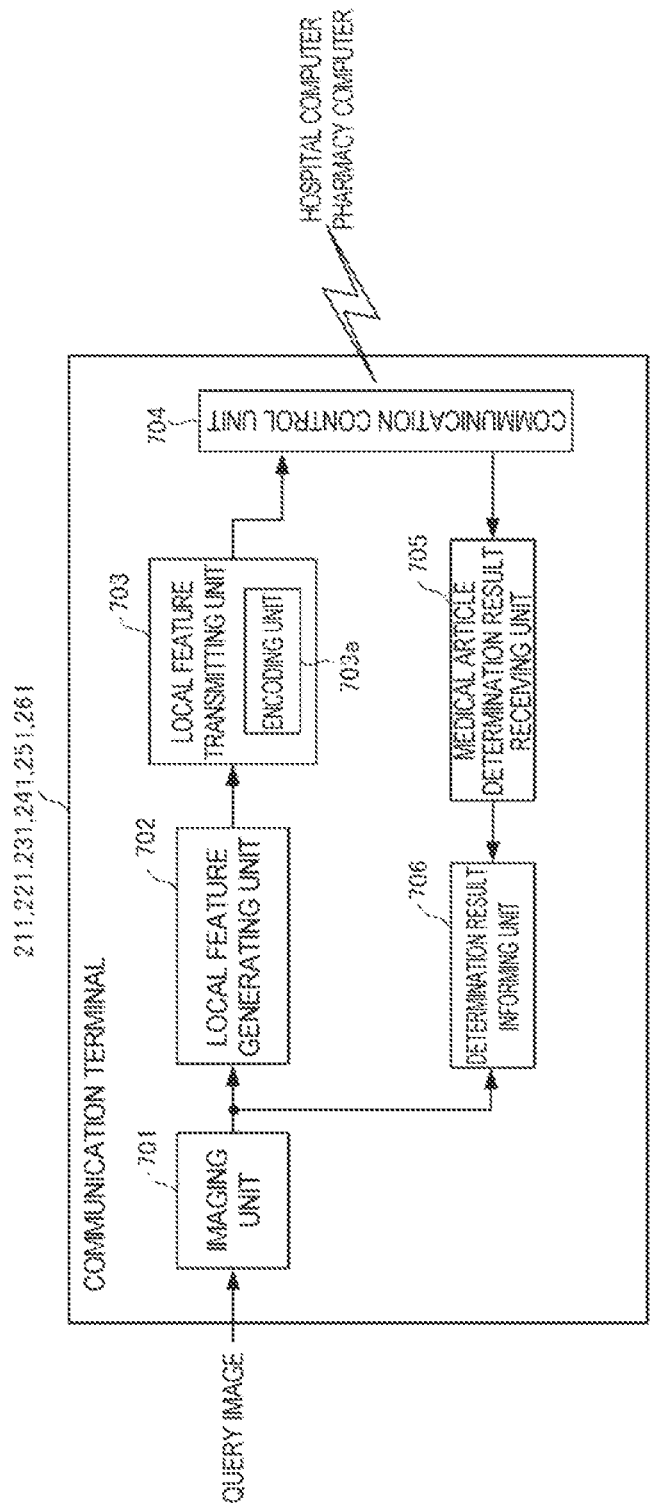
FIG. 7 is a block diagram showing a functional configuration of the communication terminal according to the second embodiment of the present invention.

FIG. 7 is a block diagram showing a functional configuration of the communication terminals 211, 221, 231, 241, and 251 according to the present embodiment.

In FIG. 7, an imaging unit 701 inputs a query image. A local feature generating unit 702 generates a local feature from a video from the imaging unit 701. The generated local feature is encoded together with a feature point coordinate by a local feature transmitting unit 703 using an encoding unit 703a and transmitted via a communication control unit 704 to a hospital computer or a pharmacy computer that performs recognition and status determination of a medical article based on the local feature.

A medical article result receiving unit 705 receives a medical article determination result via the communication control unit 704. In addition, a determination result informing unit 706 informs the received medical article determination result to a user. The determination result informing unit 706 includes a display that superimposes the video from the imaging unit 701 and the medical article determination result on one another.

Functional Configuration of Hospital Computer

Figure 8A:
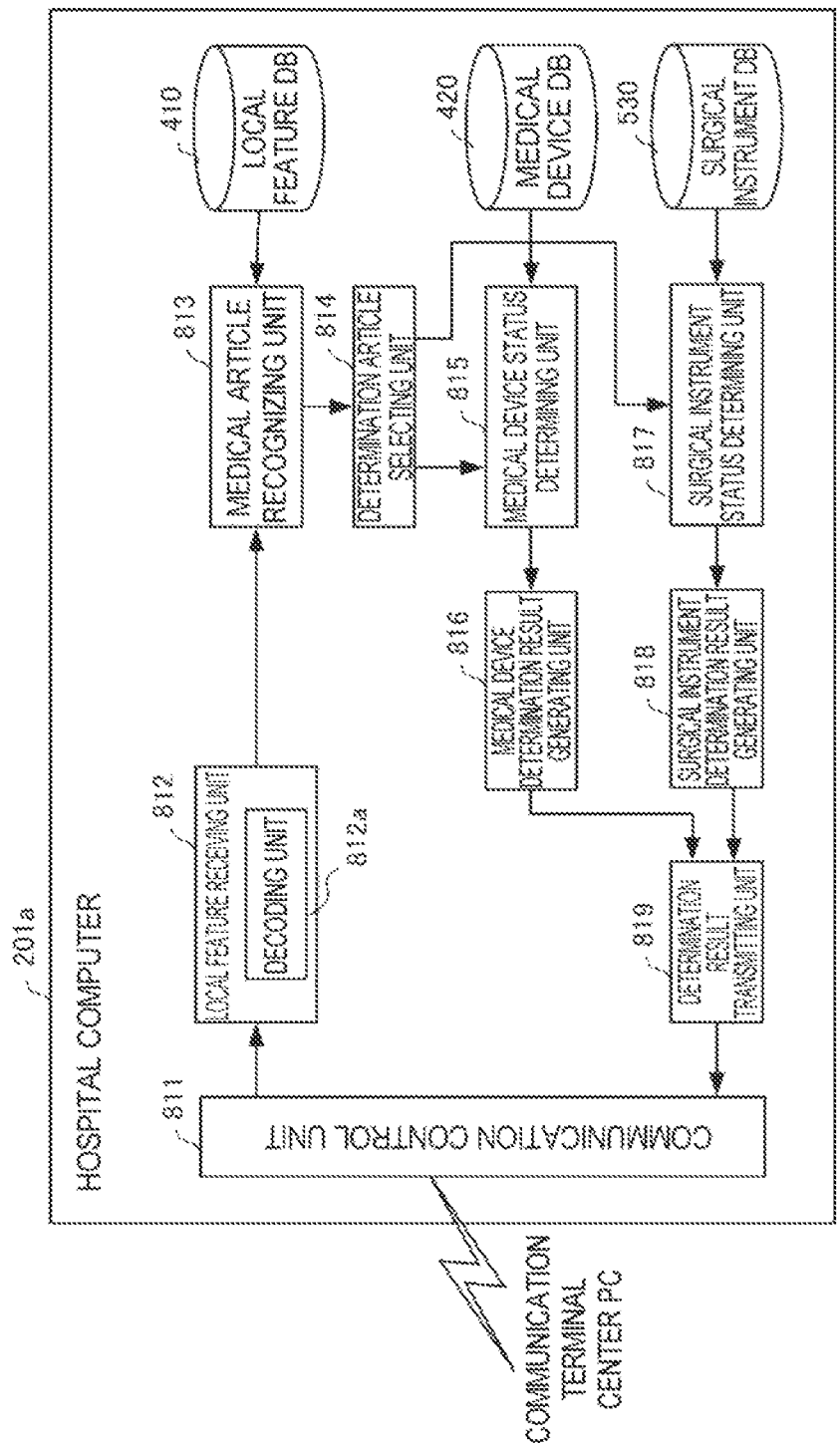
FIG. 8A is a block diagram showing a functional configuration of a hospital computer according to the second embodiment of the present invention.

FIG. 8A is a block diagram showing a functional configuration of the hospital computer 201a according to the present embodiment.

In FIG. 8A, a local feature receiving unit 812 decodes a local feature received from a communication terminal via a communication control unit 811 using a decoding unit 812a. A medical article recognizing unit 813 collates a received local feature with a local feature of the local feature DB 410 that stores local features corresponding to medical articles and recognizes a medical article.

A determination article selecting unit 814 selects a different determination depending on whether a recognized medical article is a medical device or a surgical instrument. In the case of a medical device, a status of the medical device is determined by having a medical device status determining unit 815 reference the medical device DB 420. A medical device determination result generating unit 816 generates data of a determination result.

On the other hand, in the case of a surgical instrument, a status including an arrangement and the number of the surgical instrument is determined by having a surgical instrument status determining unit 817 reference the surgical instrument DB 530. A surgical instrument determination result generating unit 818 generates data of a determination result.

A determination result transmitting unit 819 transmits data of the determination result to a communication terminal or a center PC via the communication control unit 811.

Functional Configuration of Pharmacy Computer

FIG. 8B is a block diagram showing a functional configuration of the pharmacy computer 202a according to the present embodiment.

In FIG. 8B, a local feature receiving unit 822 decodes a local feature received from a communication terminal via a communication control unit 821 using a decoding unit 822a. A pharmaceutical product recognizing unit 823 collates a received local feature with a local feature of the local feature DB 610 that stores local features corresponding to pharmaceutical products (medicine shelf) and recognizes the pharmaceutical product (medicine shelf).

A determination article selecting unit 814 selects a different determination depending on whether a recognized medical article is a pharmaceutical product or includes a medicine shelf. In the case of a pharmaceutical product, a status of the pharmaceutical product is determined by having a prescription status determining unit 825 reference the prescription DB 620. A prescription determination result generating unit 826 generates data of a determination result.

On the other hand, when a medicine shelf is included, a status including an arrangement and the number of pharmaceutical products in the medicine shelf is determined by having a medicine shelf status determining unit 827 reference the stock management DB 630. A stock management result generating unit 828 generates data of a determination result.

A determination result transmitting unit 829 transmits data of the determination result to a communication terminal or an operator PC via the communication control unit 821.

Hospital Local Feature DB

FIG. 9A is a diagram showing a configuration of the local feature DB 410 of a hospital according to the present embodiment. It should be noted that the shown configuration is not restrictive.

The local feature DB 410 stores a first local feature 913, a second local feature 914, . . . , and an m-th local feature 915 in association with a medical article ID (a medical device ID or a medical instrument ID) 911 and a name/type 912. Each local feature corresponds to a 5×5 sub-area and stores a feature vector constituted by 1-dimensional to 150-dimensional elements that are hierarchized in unit of 25 dimensions (refer to FIG. 11F).

Moreover, m denotes a positive integer and may be a different number corresponding to a medical article ID. In addition, in the present embodiment, a feature point coordinate that is used in a collating process is stored together with each local feature.

Medical Device DB

Figure 9B:
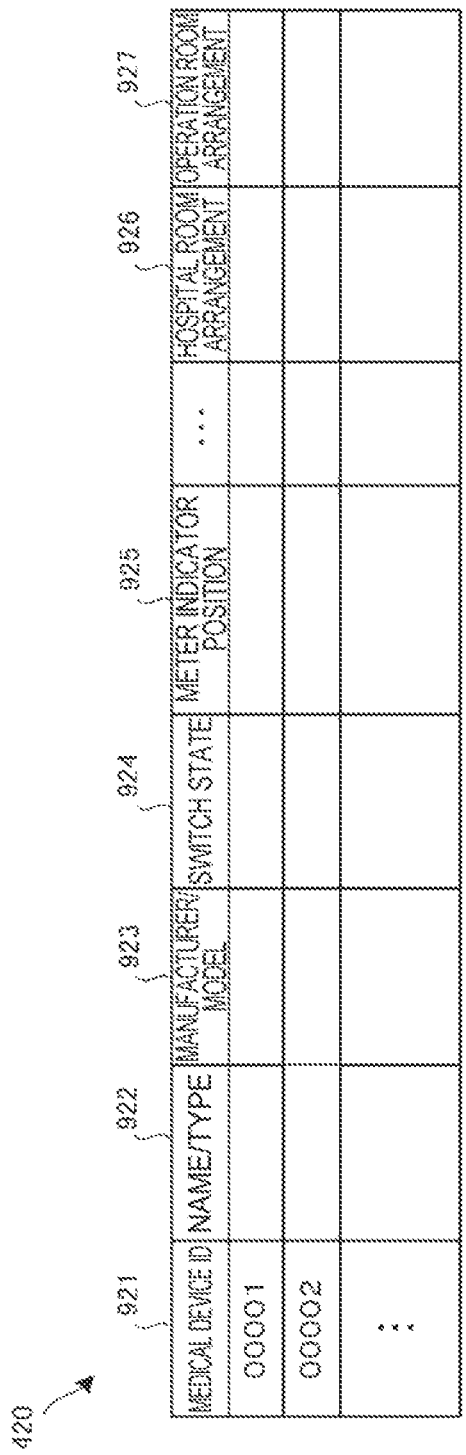
FIG. 9B is a diagram showing a configuration of a medical device DB according to the second embodiment of the present invention.

FIG. 9B is a diagram showing a configuration of the medical device DB 420 according to the present embodiment. It should be noted that the shown configuration is not restrictive.

The medical device DB 420 stores a manufacturer/model 923, a switch state 924, a meter indicator position (a display waveform position) 925, a hospital room arrangement 926, and an operation room arrangement 927 in association with a medical device ID 921 and a name/type 922.

Surgical Instrument DB

FIG. 9C is a diagram showing a configuration of the surgical instrument DB 530 according to the present embodiment. The surgical instrument DB 530 includes a DB 930 storing information on each surgical instrument and a DB 940 storing an arrangement in a tray and the number of a surgical instrument in association with an operation. It should be noted that the shown configuration is not restrictive.

The DB 930 that stores information on each surgical instrument stores a manufacturer/model 933, a size 934, shape 935, and a surface state 936 in association with a surgical instrument ID 931 and a name/type 932.

The DB 940 that stores an arrangement in a tray and the number of a surgical instrument stores a tray arrangement and the number 942 of a first surgical instrument ID, a tray arrangement and the number 943 of a second surgical instrument ID, and a tray arrangement and the number 944 of a k-th surgical instrument ID in association with an operation type 941.

Pharmacy Local Feature DB

FIG. 10A is a diagram showing a configuration of the local feature DB 610 of a pharmacy according to the present embodiment. It should be noted that the shown configuration is not restrictive.

The local feature DB 610 stores a first local feature 1013, a second local feature 1014, . . . , and an m-th local feature 1015 in association with a medical article ID (a pharmaceutical product ID or a medicine shelf ID) 1011 and a name/type 1012. Each local feature corresponds to a 5×5 sub-area and stores a feature vector constituted by 1-dimensional to 150-dimensional elements that are hierarchized in units of 25 dimensions (refer to FIG. 11F).

Moreover, m denotes a positive integer and may be a different number corresponding to a medical article ID. In addition, in the present embodiment, a feature point coordinate that is used in a collating process is stored together with each local feature.

Prescription DB

FIG. 10B is a diagram showing a configuration of the prescription DB 620 according to the present embodiment. It should be noted that the shown configuration is not restrictive.

The prescription DB 620 stores a prescription 1024 in association with a patient ID 1021, a patient name 1022, and a date/time 1023. A pharmaceutical product ID or a generic ID is stored in a name field of the prescription 1024.

Stock Management DB

FIG. 10C is a diagram showing a configuration of the stock management DB 630 according to the present embodiment. It should be noted that the shown configuration is not restrictive.

Whether generic or not 1032, a corresponding original pharmaceutical product in case of generic 1033, a shelf position 1034, an inbound amount 1035, an outbound amount 1036, and a stock amount 1037 are stored in association with a pharmaceutical product ID 1031.

Local Feature Generating Unit

FIG. 11A is a block diagram showing a configuration of the local feature generating unit 702 according to the present embodiment.

The local feature generating unit 702 is configured so as to include a feature point detecting unit 1111, a local area acquiring unit 1112, a sub-area dividing unit 1113, a sub-area feature vector generating unit 1114, and a dimension selecting unit 1115.

The feature point detecting unit 1111 detects a large number of characteristic points (feature points) from image data and outputs a coordinate position, a scale (size), and an angle of each feature point.

The local area acquiring unit 1112 acquires a local area to be subjected to feature extraction from the coordinate position, the scale, and the angle of each detected feature point.

The sub-area dividing unit 1113 divides the local area into sub-areas. For example, the sub-area dividing unit 1113 can divide the local area into 16 blocks (4×4 blocks) or 25 blocks (5×5 blocks). It should be noted that the number of divisions is not restrictive. In the present embodiment, a case where a local area is divided into 25 blocks (5×5 blocks) will be described below as a representative example.

The sub-area feature vector generating unit 1114 generates a feature vector for each sub-area of the local area. For example, a gradient direction histogram can be used as a feature vector of a sub-area.

Based on a positional relationship between sub-areas, the dimension selecting unit 1115 selects (for example, thins) a dimension to be outputted as a local feature so as to lower a correlation between feature vectors of adjacent sub-areas. In addition, besides simply selecting a dimension, the dimension selecting unit 1115 can determine a priority order of selection. In other words, for example, the dimension selecting unit 1115 can select a dimension by applying a priority order so that a dimension with a same gradient direction is not selected between adjacent sub-areas. Furthermore, the dimension selecting unit 1115 outputs a feature vector constituted by a selected dimension as a local feature. Moreover, the dimension selecting unit 1115 can output a local feature in a state where dimensions are sorted based on a priority order.

Processes by Local Feature Generating Unit

FIGS. 11B to 11F are diagrams showing processes by the local feature generating unit 702 according to the present embodiment.

First, FIG. 11B is a diagram showing a series of processes including feature point detection, local area acquisition, sub-area division, and feature vector generation performed by the local feature generating unit 702. Regarding the series of processes, refer to U.S. Pat. No. 6,711,293 and David G Lowe, "Distinctive image features from scale-invariant keypoints", USA, International Journal of Computer Vision, 60 (2), 2004, pages 91-110.

Feature Point Detecting Unit

An image 1121 shown in FIG. 11B is a diagram representing a state where a feature point has been detected from an image in a video by the feature point detecting unit 1111 shown in FIG. 11A. Hereinafter, generation of a local feature will be described using one piece of feature point data 1121a as a representative example. An origin of an arrow depicting the feature point data 1121a indicates a coordinate position of a feature point, a length of the arrow indicates a scale (size) thereof, and a direction of the arrow indicates an angle thereof. In this case, with respect to the scale (size) and direction, brightness, chroma, hue, or the like can be selected according to an object video. In addition, while a case of six directions at 60-degree intervals will be described in the example shown in FIG. 11B, this example is not restrictive.

Local Area Acquiring Unit

For example, the local area acquiring unit 1112 shown in FIG. 11A generates a Gaussian window 1122a centered on the origin of the feature point data 1121a and generates a local area 1122 that approximately includes the Gaussian window 1122a. While the local area acquiring unit 1112 generates a square local area 1122 in the example shown in FIG. 11B, the local area may be circular or have other shapes. This local area is acquired for each feature point. A circular local area creates an effect of improved robustness with respect to a direction of photography.

Sub-Area Dividing Unit

Next, a state is shown where the sub-area dividing unit 1113 has divided a scale and an angle of each pixel included in the local area 1122 of the feature point data 1121a into sub-areas 1123. Moreover, FIG. 11B shows an example of a division into 5×5=25 sub-areas, where each sub-area is constituted by 4×4=16 pixels. However, besides 4×4=16, the sub-areas may have other shapes and numbers of divisions.

Sub-Area Feature Vector Generating Unit

The sub-area feature vector generating unit 1114 quantizes a scale of each pixel in a sub-area by generating a histogram in angle units of six directions to obtain a sub-area feature vector 1124. In other words, the directions are normalized with respect to angles outputted by the feature point detecting unit 1111. In addition, the sub-area feature vector generating unit 1114 sums up frequencies of the six quantized directions for each sub-area and generates a histogram. In this case, the sub-area feature vector generating unit 1114 outputs a feature vector constituted by a histogram of 25 sub-area blocks×6 directions=150 dimensions that is generated with respect to each feature point. Alternatively, besides quantizing a gradient direction in six directions, quantization may be performed in any quantization number such as 4 directions, 8 directions, and 10 directions. When a gradient direction is quantized in D-number of directions, if the gradient direction prior to quantization is denoted by G (0 to 2π radian), then a quantization value Qq (q=0, ..., D−1) of the gradient direction can be calculated using, for example, Equation (1) or Equation (2). However, these equations are not restrictive and other equations may be used.

$$Qq = \text{floor}(G \times D/2\pi) \quad (1)$$

$$Qq = \text{round}(G \times D/2\pi) \bmod D \quad (2)$$

In the equations above, floor ( ) denotes a function for truncating a fractional part, round ( ) denotes a rounding-off function, and mod denotes an operation for determining a remainder. In addition, when generating a gradient histogram, the sub-area feature vector generating unit 1114 may calculate a sum by adding a magnitude of gradients instead of simply summing up frequencies. Alternatively, when summing up gradient histograms, the sub-area feature vector generating unit 1114 may add a weight value not only to a sub-area to which a pixel belongs but also to a neighboring sub-area (such as an adjacent block) depending on a distance between sub-areas. Alternatively, the sub-area feature vector generating unit 1114 may also add weight values to gradient directions before and after the quantized gradient direction. Moreover, a feature vector of a sub-area is not limited to a gradient direction histogram and may be any information having a plurality of dimensions (elements) such as color information. The present embodiment will be described on the assumption that a gradient direction histogram is to be used as a feature vector of a sub-area.

Dimension Selecting Unit

Next, processes of the dimension selecting unit 1115 in the local feature generating unit 702 will be described with reference to FIGS. 11C to 11F.

Based on a positional relationship between sub-areas, the dimension selecting unit 1115 selects (thins) a dimension (element) to be outputted as a local feature so as to lower a correlation between feature vectors of adjacent sub-areas. More specifically, for example, the dimension selecting unit 1115 selects a dimension so that at least one gradient direction differs between adjacent sub-areas. Moreover, while the dimension selecting unit 1115 is to mainly use adjacent sub-areas as neighboring sub-areas in the present embodiment, neighboring sub-areas are not limited to adjacent sub-areas and, for example, sub-areas within a predetermined distance from an object sub-area may be considered neighboring sub-areas.

FIG. 11C is a diagram showing an example in which a local area is divided into sub-areas of 5×5 blocks and a dimension is selected from a feature vector 1131 of a 150-dimensional gradient histogram that is generated by quantizing a gradient direction in six directions 1131a. In the example shown in FIG. 11C, dimensions are selected from a 150-dimensional (5×5=25 sub-area blocks×6 directions) feature vector.

Dimension Selection of Local Area

FIG. 11C is a diagram showing how a selecting process of the number of dimensions of a feature vector is performed by the local feature generating unit 702.

As shown in FIG. 11C, the dimension selecting unit 1115 selects a feature vector 1132 of a 75-dimensional gradient histogram that is half of the dimensions from the feature vector 1131 of the 150-dimensional gradient histogram. In this case, dimensions can be selected so that a dimension with a same gradient direction is not selected for upper and lower sub-area blocks or left and right sub-area blocks that are adjacent to one another.

In this example, when a quantized gradient direction of a gradient direction histogram is denoted by q (q=0, 1, 2, 3, 4, 5), a block in which elements of q=0, 2, 4 are selected and a sub-area block in which elements of q=1, 3, 5 are selected are alternately arranged. Furthermore, in the examples shown in FIG. 11C, the gradient directions selected between adjacent sub-area blocks add up to a total of six directions.

In addition, the dimension selecting unit 1115 selects a feature vector 1133 of a 50-dimensional gradient histogram from the feature vector 1132 of the 75-dimensional gradient histogram. In this case, dimensions can be selected so that only one direction is the same (the remaining one direction is different) between sub-area blocks positioned at an oblique 45 degrees with respect to one another.

In addition, when selecting a feature vector 1134 of a 25-dimensional gradient histogram from the feature vector 1133 of the 50-dimensional gradient histogram, the dimension selecting unit 1115 can select dimensions so that selected gradient directions are not consistent between sub-area blocks positioned at an oblique 45 degrees with respect to one another. In the example shown in FIG. 11C, the dimension selecting unit 1115 selects one gradient direction from each sub-area for 1 to 25 dimensions, two gradient directions for 26 to 50 dimensions, and three gradient directions for 51 to 75 dimensions.

As described above, dimensions are desirably selected so that gradient directions do not overlap each other between adjacent sub-area blocks and that all gradient directions are evenly selected. In addition, at the same time, dimensions are desirably selected evenly from an entire local area as in the example shown in FIG. 11C. Moreover, the dimension selection method shown in FIG. 11C is merely an example and selection methods are not limited thereto.

Priority Order of Local Area

FIG. 11D is a diagram showing an example of a selection order of a feature vector from a sub-area by the local feature generating unit 702.

Besides simply selecting dimensions, the dimension selecting unit 1115 can determine a priority order of selection so that dimensions are selected in a descending order of their contributions to a feature of a feature point. In other words, for example, the dimension selecting unit 1115 can select dimensions by applying a priority order so that a dimension of a same gradient direction is not selected between adjacent sub-area blocks. Furthermore, the dimension selecting unit 1115 outputs a feature vector constituted by selected dimensions as a local feature. Moreover, the dimension selecting unit 1115 can output a local feature in a state where dimensions are sorted based on a priority order.

In other words, for example, the dimension selecting unit 1115 may select dimensions for 1 to 25 dimensions, 26 to 50 dimensions, and 51 to 75 dimensions so as to add dimensions in an order of sub-area blocks such as that represented by a matrix 1141 shown in FIG. 11D. When using the priority order represented by the matrix 1141 shown in FIG. 11D, the dimension selecting unit 1115 can select gradient directions by giving a high priority order to a sub-area block close to center.

Figure 11E:
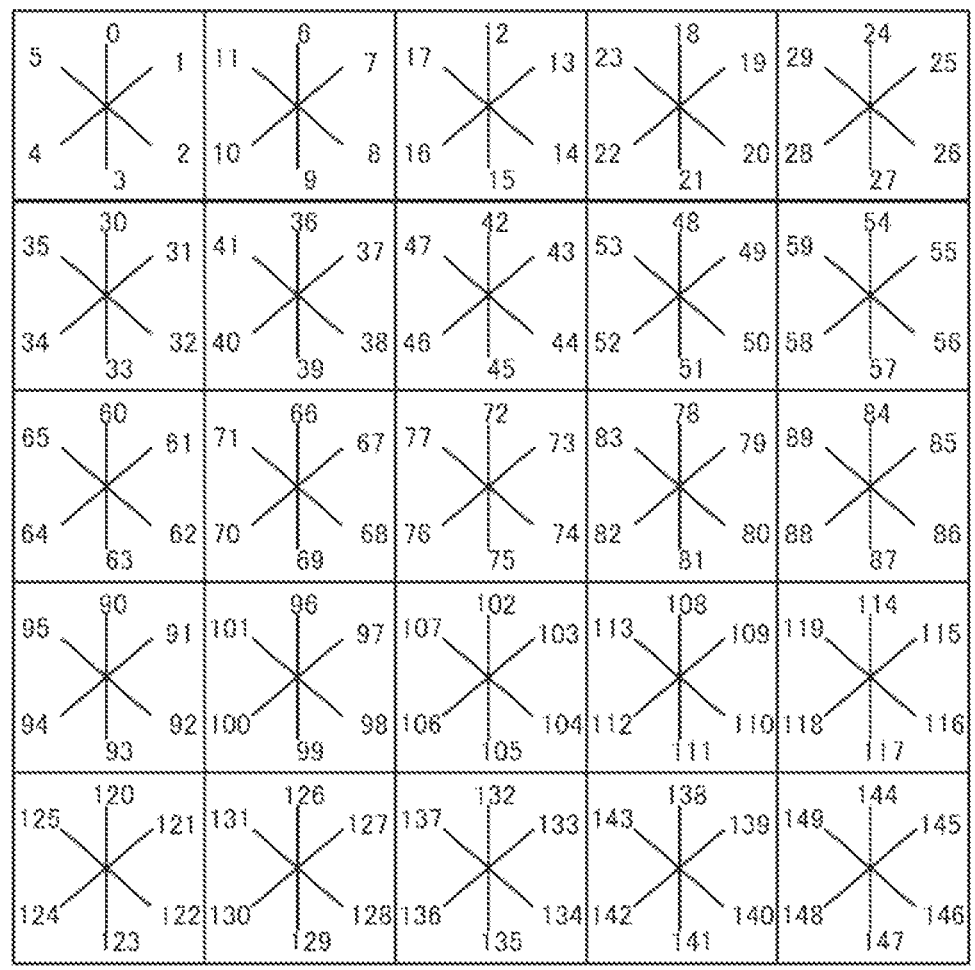
FIG. 11E is a diagram showing a selection order of feature vectors in the local feature generating unit according to the second embodiment of the present invention.

A matrix 1151 shown in FIG. 11E is a diagram showing an example of numbers of elements of a 150-dimensional feature vector in accordance with the selection order shown in FIG. 11D. In this example, if 5×5=25 blocks are denoted in a raster-scanning order by a number p (p=0, 1, . . . , 25) and a quantized gradient direction is denoted by q (q=0, 1, 2, 3, 4, 5), then a number of an element of a feature vector is expressed as 6×p+q.

Figure 11F:
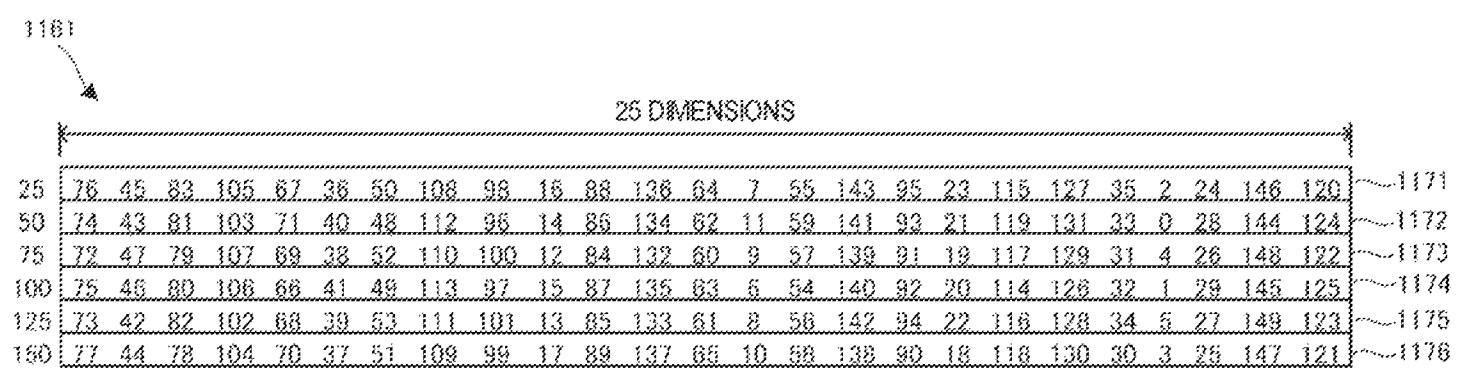

A matrix 1161 shown in FIG. 11F is a diagram showing that orders of 150 dimensions according to the selection order shown in FIG. 11E are hierarchized in units of 25 dimensions. In other words, the matrix 1161 shown in FIG. 11F is a diagram showing a configuration example of a local feature that is obtained by selecting the elements shown in FIG. 11E according to the priority order represented by the matrix 1141 shown in FIG. 4D. The dimension selecting unit 1115 can output dimensional elements in the order shown in FIG. 11F. Specifically, for example, when outputting a 150-dimensional local feature, the dimension selecting unit 1115 can output elements of all 150 dimensions in the order shown in FIG. 11F. In addition, for example, when outputting a 25-dimensional local feature, the dimension selecting unit 1115 can output elements 1171 of a first row (76th, 45th, 83rd, . . . , 120th) shown in FIG. 11F in an order (from left to right) shown in FIG. 11F. Furthermore, for example, when outputting a 50-dimensional local feature, the dimension selecting unit 1115 can output elements 1172 of a second row shown in FIG. 11F in addition to the first row shown in FIG. 11F in the order (from left to right) shown in FIG. 11F.

In the example shown in FIG. 11F, a local feature has a hierarchical structure. In other words, for example, between a 25-dimensional local feature and a 150-dimensional local feature, arrangements of the elements 1171 to 1176 of a local feature corresponding to the first 25 dimensions are the same. As shown, by selecting dimensions hierarchically (progressively), the dimension selecting unit 1115 can extract and output a local feature of an arbitrary number of dimensions or, in other words, a local feature of an arbitrary size in accordance with applications, communication capacity, terminal specifications, or the like. In addition, due to the dimension selecting unit 1115 selecting dimensions hierarchically and outputting the dimensions after sorting based on a priority order, image collation can be performed using local features with different numbers of dimensions. For example, when image collation is performed using a 75-dimensional local feature and a 50-dimensional local feature, a calculation of a distance between the local features can be performed using only the first 50 dimensions.

Moreover, the priority orders represented by the matrix 1141 shown in FIG. 11D to FIG. 11F are simply examples and an order that is applied when selecting dimensions is not limited thereto. For example, regarding an order of blocks, orders represented by a matrix 1142 shown in FIG. 11D and a matrix 1143 shown in FIG. 11D may be adopted in addition to the example of the matrix 1141 shown in FIG. 11D. In addition, for example, a priority order may be set so that dimensions are evenly selected from all sub-areas. Alternatively, on the assumption that a vicinity of a center of a local area is important, a priority order may be set so that selection frequency is high in sub-areas in the vicinity of the center. Furthermore, for example, information indicating a selection order of dimensions may be defined in a program or stored in a table or the like (a selection order storing unit) that is referenced by the program upon execution.

Alternatively, the dimension selecting unit 1115 may select dimensions by selecting every other sub-area block. In other words, six dimensions are selected in a given sub-area and zero dimensions are selected in another sub-area that is adjacent to the given sub-area. Even in such a case, it is safe to say that dimensions are selected for each sub-area so that a correlation between neighboring sub-areas is lowered.

In addition, shapes of a local area and a sub-area are not limited to a square and may be arbitrary shapes. For example, the local area acquiring unit 1112 may be configured so as to acquire a circular local area. In this case, for example, the sub-area dividing unit 1113 can divide the circular local area as a concentric circle having a plurality of local areas into 9 sub-areas or 17 sub-areas. Even in this case, the dimension selecting unit 1115 can select dimensions in each sub-area.

As described above and shown in FIGS. 11B to 11F, with the local feature generating unit 702 according to the present embodiment, dimensions of a generated feature vector are hierarchically selected while maintaining an information amount of a local feature. According to these processes, medical article recognition and recognition result display can be realized in real time while maintaining recognition accuracy. Moreover, configurations and processes of the local feature generating unit 702 are not limited to the present example. It is obvious that other processes that enable medical article recognition and recognition result display to be realized in real time while maintaining recognition accuracy are also applicable.

Encoding Unit

Figure 11G:
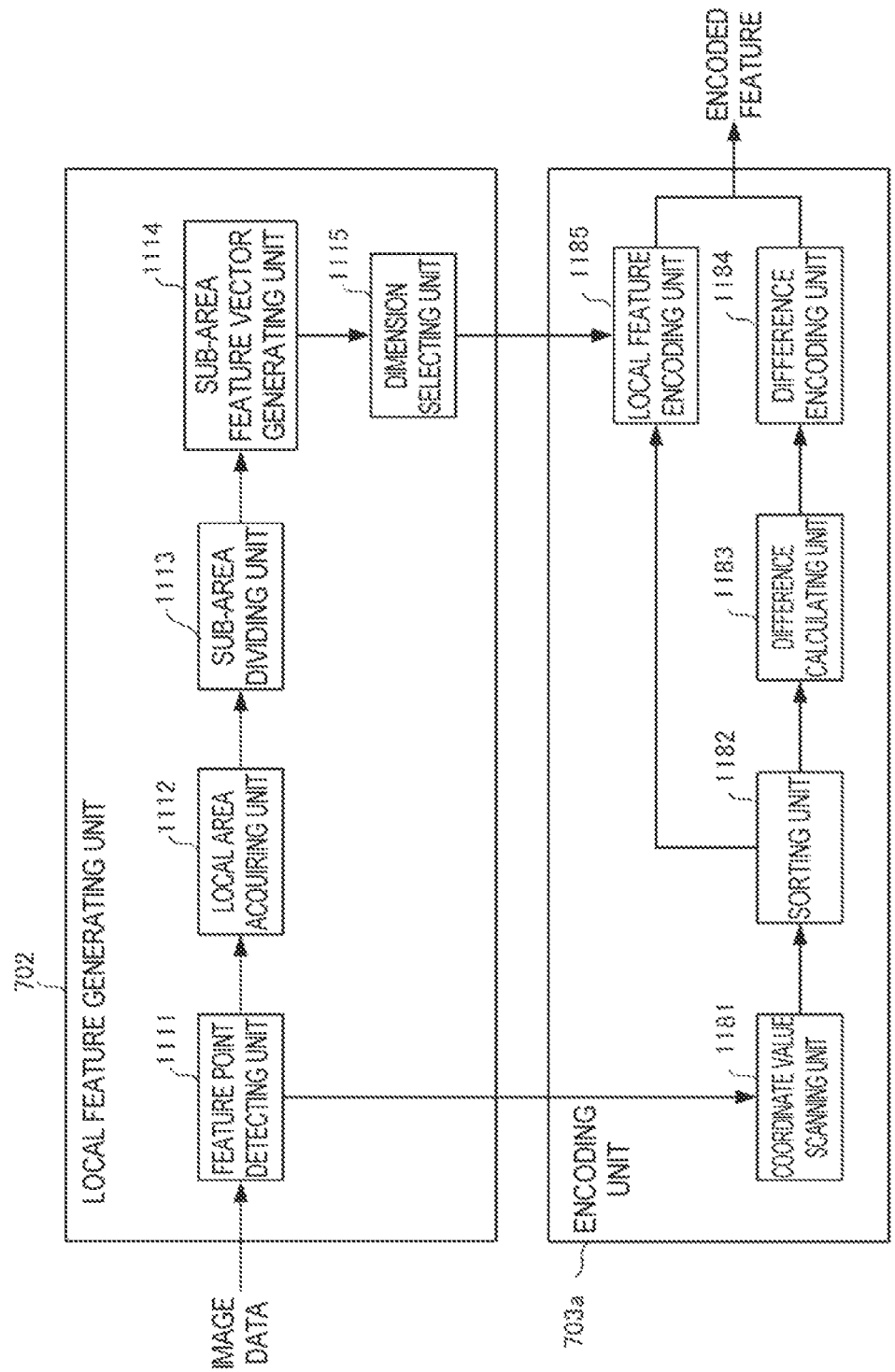
FIG. 11G is a diagram showing a configuration of an encoding unit according to the second embodiment of the present invention.

FIG. 11G is a block diagram showing the encoding unit 703a according to the present embodiment. Moreover, the encoding unit is not limited to the present example and other encoding processes are also applicable.

The encoding unit 703a has a coordinate value scanning unit 1181 which receives input of a coordinate of a feature point from the feature point detecting unit 1111 of the local feature generating unit 702 and which scans the coordinate value. The coordinate value scanning unit 1181 scans an image according to a particular scanning method and converts a two-dimensional coordinate value (an X coordinate value and a Y coordinate value) of a feature point into a one-dimensional index value. The index value represents a scanning distance from an origin according to the scanning. Moreover, a scanning direction is not restrictive.

In addition, the encoding unit 703a has a sorting unit 1182 which sorts index values of a feature point and outputs information on a permutation after sorting. In this case, for example, the sorting unit 1182 performs sorting in an ascending order. Alternatively, sorting may be performed in a descending order.

Furthermore, the encoding unit 703a has a difference calculating unit 1183 which calculates a difference value between two adjacent index values among the sorted index values and which outputs a series of difference values.

In addition, the encoding unit 703a has a difference encoding unit 1184 that encodes a series of difference values in a series order. The encoding of a series of difference values may be, for example, fixed bit length encoding. When encoding with a fixed bit length, the bit length may be defined in advance. However, in this case, since the number of bits necessary for expressing a conceivable maximum value of the difference values is required, encoding size is not reduced. In consideration thereof, when encoding with a fixed bit length, the difference encoding unit 1184 can determine a bit length based on an inputted difference value series. Specifically, for example, the difference encoding unit 1184 can obtain a maximum value of the difference values from the inputted difference value series, obtain the number of bits necessary for expressing the maximum value (the number of expression bits), and encode the difference value series with the obtained number of expression bits.

Meanwhile, the encoding unit 703a has a local feature encoding unit 1185 that encodes a local feature of a corresponding feature point with a same permutation as the sorted index values of the feature points. Performing encoding with the same permutation as the sorted index values enables a coordinate value encoded by the difference encoding unit 1184 and a corresponding local feature to be associated with each other on a one-to-one basis. In the present embodiment, the local feature encoding unit 1185 can encode a local feature resulting from a dimension selection from a 150-dimensional local feature corresponding to one feature point with bytes of the number of dimensions by, for example, encoding one dimension as one byte.

Medical Article Recognizing Unit/Pharmaceutical Product Recognizing Unit

Figure 11H:
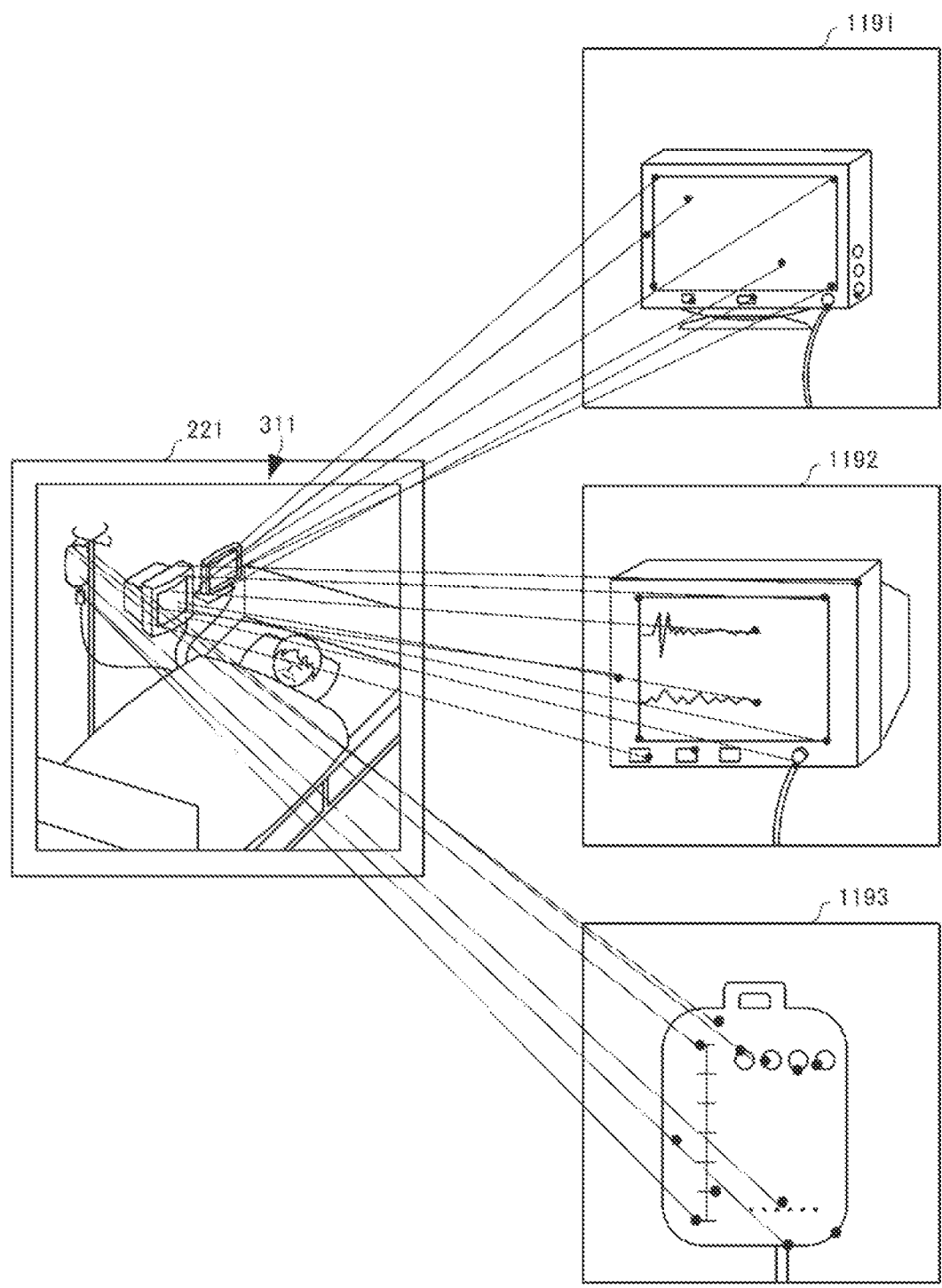
FIG. 11H is a diagram showing processing by a medical article recognizing unit in a hospital room according to the second embodiment of the present invention.
Figure 11J:
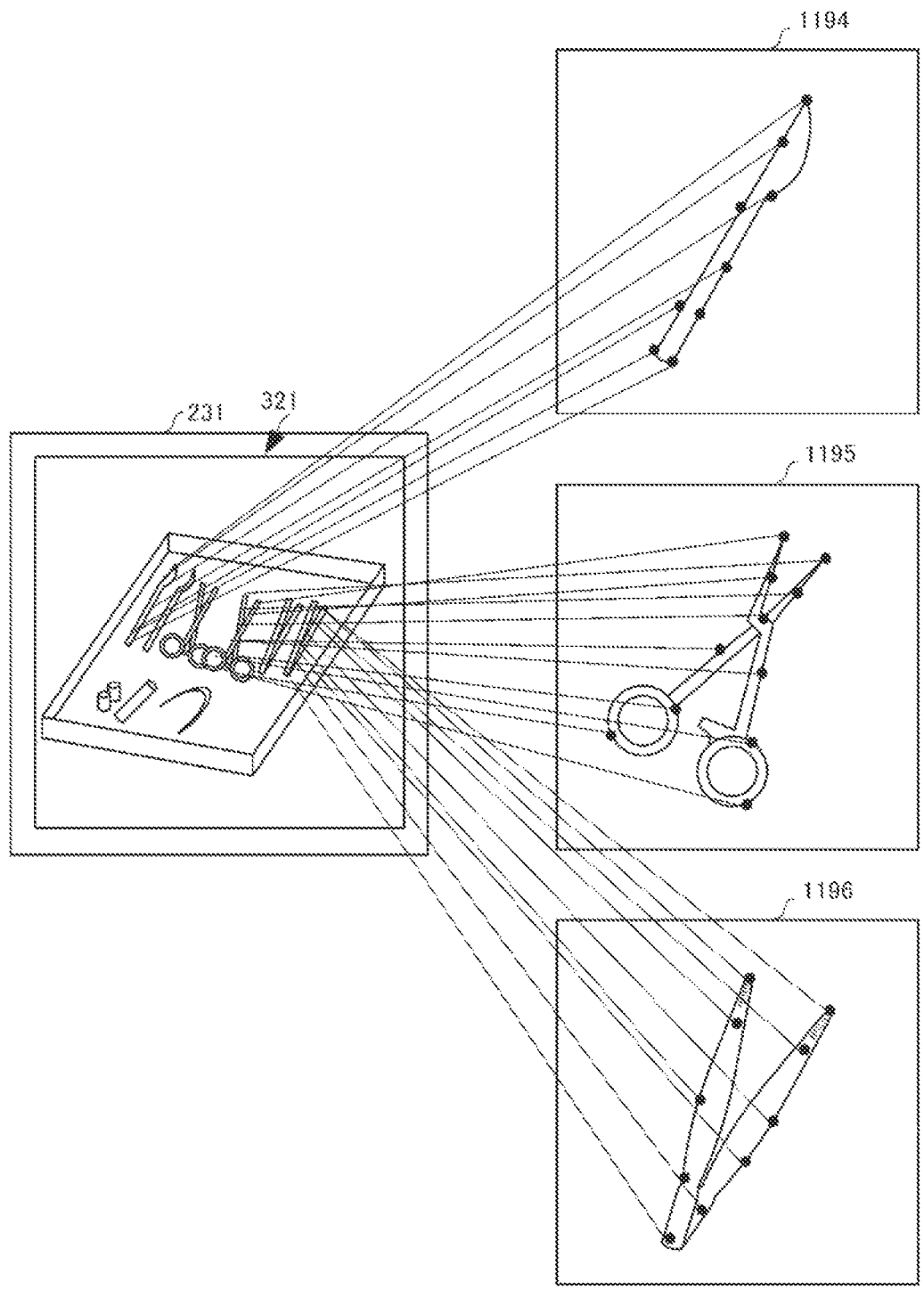
FIG. 11J is a diagram showing processing by a medical article recognizing unit in an operation room according to the second embodiment of the present invention.
Figure 11K:
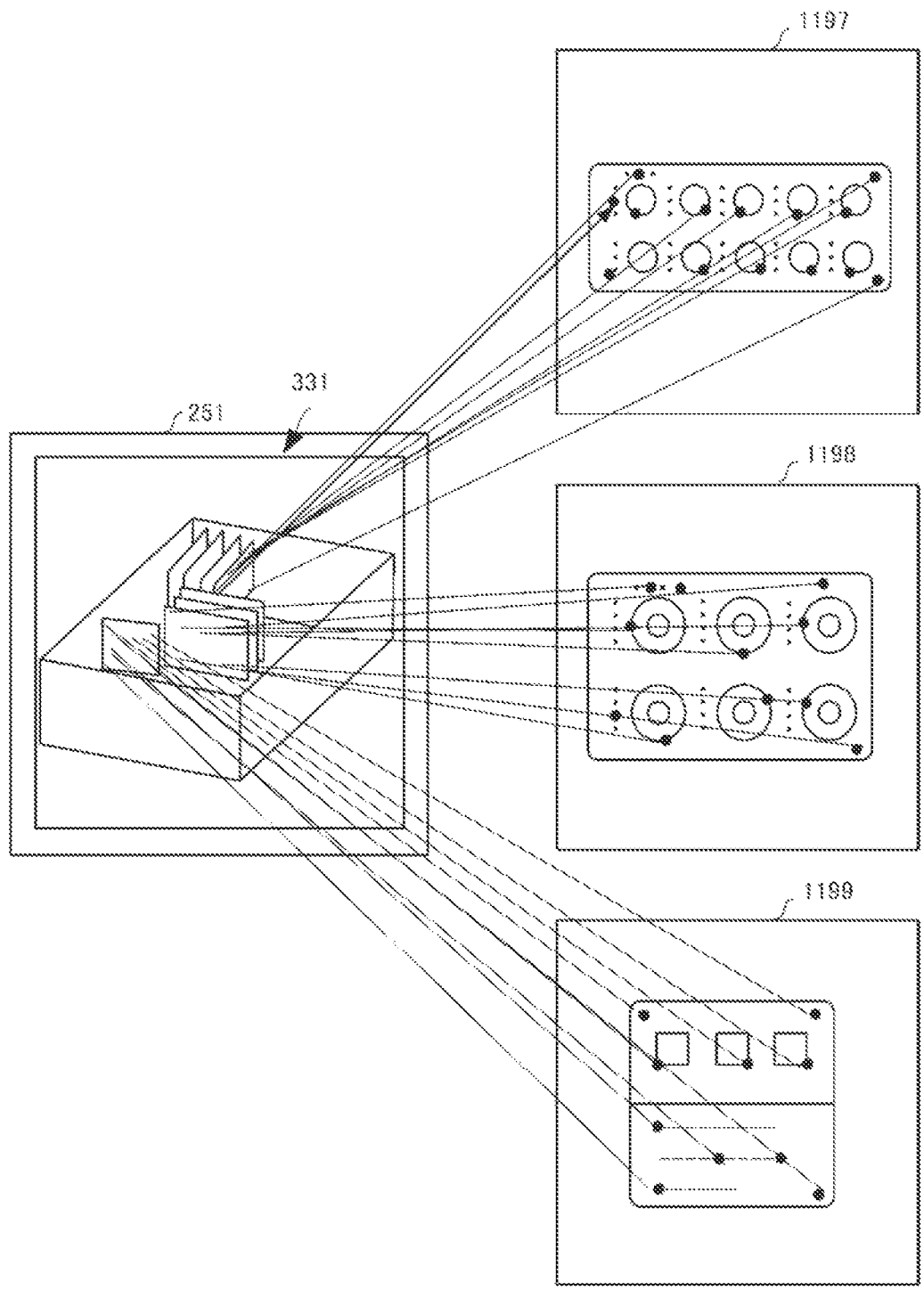
FIG. 11K is a diagram showing processing by a pharmaceutical product recognizing unit in a pharmacy according to the second embodiment of the present invention.

FIGS. 11H, 11J, and 11K are diagrams showing processes by the medical article recognizing unit 813 and the pharmaceutical product recognizing unit 823 according to the present embodiment.

FIG. 11H is a diagram showing a process by the medical article recognizing unit 813 in the hospital room shown in FIG. 2. Local features 1191 to 1193 which are shown in FIG. 11H and which are generated in advance according to the present embodiment from a medical device or an infusion bag are stored in the local feature DB 410. Meanwhile, a local feature is generated according to the present embodiment from the video screen 311 captured by the communication terminal 221 shown in a left diagram in FIG. 11H. In addition, collation is performed with respect to whether or not the local features 1191 to 1193 stored in the local feature DB 410 can be found in the local features generated from the video screen 311.

As shown in FIG. 11H, the medical article recognizing unit 813 associates a local feature stored in the local feature DB 410 with each feature point which the local feature matches as depicted by a fine line. Moreover, the medical article recognizing unit 813 assumes a case where a prescribed ratio or more of the local features is consistent to be a feature point match. In addition, if a positional relationship between sets of the associated feature points is a linear relationship, the medical article recognizing unit 813 recognizes an object medical article. By performing such recognition, recognition can be made even in a case where sizes or orientations (viewpoints) differ, a case of inversion, or the like. Furthermore, since recognition accuracy can be obtained when there is a prescribed number or more of associated feature points, a medical article can be recognized even if a part of the medical article is hidden from view.

In FIG. 11H, three medical articles with different orientations in the hospital room which match the local features 1191 to 1193 of three medical articles in the local feature DB 410 are recognized with precision corresponding to the accuracy of the local features.

FIG. 11J is a diagram showing a process by the medical article recognizing unit 813 with respect to a medical article (a surgical instrument) in the operation room shown in FIG. 2. Local features 1194 to 1196 which are shown in FIG. 11J and which are generated in advance according to the present embodiment from medical devices such as a scalpel, forceps, and tweezers are stored in the local feature DB 410. Meanwhile, a local feature is generated according to the present embodiment from the video screen 321 captured by the communication terminal 231 shown in a left diagram in FIG. 11J. In addition, collation is performed with respect to whether or not the local features 1194 to 1196 stored in the local feature DB 410 can be found in the local features generated from the video screen 321.

As shown in FIG. 11J, the medical article recognizing unit 813 associates a local feature stored in the local feature DB 410 with each feature point which the local feature matches as depicted by a fine line. Moreover, the medical article recognizing unit 813 assumes a case where a prescribed ratio or more of the local features is consistent to be a feature point match. In addition, if a positional relationship between sets of the associated feature points is a linear relationship, the medical article recognizing unit 813 recognizes an object medical article. By performing such recognition, recognition can be made even in a case where sizes or orientations (viewpoints) differ, a case of inversion, or the like. Furthermore, since recognition accuracy can be obtained when there is a prescribed number or more of associated feature points, a medical article can be recognized even if a part of the medical article is hidden from view.

In FIG. 11J, surgical instruments with different orientations in the surgical instrument tray which match the local features 1194 to 1196 of three medical articles in the local feature DB 410 are recognized with precision corresponding to the accuracy of the local features. Moreover, while FIG. 11J shows only one surgical instrument in the surgical instrument tray being associated with each surgical instrument in order to avoid complexity, a similar process is applied when recognizing other surgical instruments that are the same.

FIG. 11K is a diagram showing a process by the pharmaceutical product recognizing unit 823 with respect to a pharmaceutical product in a medicine tray in the pharmacy shown in FIG. 2. Local features 1197 to 1199 which are shown in FIG. 11K and which are generated in advance according to the present embodiment from each pharmaceutical product are stored in the local feature DB 610. Meanwhile, a local feature is generated according to the present embodiment from the video screen 331 captured by the communication terminal 251 shown in a left diagram in FIG. 11K. In addition, collation is performed with respect to whether or not the local features 1197 to 1199 stored in the local feature DB 610 can be found in the local features generated from the video screen 331.

As shown in FIG. 11K, the pharmaceutical product recognizing unit 823 associates a local feature stored in the local feature DB 610 with each feature point which the local feature matches as depicted by a fine line. Moreover, the pharmaceutical product recognizing unit 823 assumes a case where a prescribed ratio or more of the local features is consistent to be a feature point match. In addition, if a positional relationship between sets of the associated feature points is a linear relationship, the pharmaceutical product recognizing unit 823 recognizes an object medical article. By performing such recognition, recognition can be made even in a case where sizes or orientations (viewpoints) differ, a case of inversion, or the like. Furthermore, since recognition accuracy can be obtained when there is a prescribed number or more of associated feature points, a medical article can be recognized even if a part of the medical article is hidden from view.

In FIG. 11K, pharmaceutical products with different orientations in the medicine tray which match the local features 1197 to 1199 of three pharmaceutical products in the local feature DB 610 are recognized with precision corresponding to the accuracy of the local features. Moreover, while FIG. 11K shows only one pharmaceutical product in the medicine tray being associated with each pharmaceutical product in order to avoid complexity, a similar process is applied when recognizing other pharmaceutical products that are the same.

Moreover, while collation is performed based on a feature point coordinate and a local feature in the collating processes by the medical article recognizing unit 813 and the pharmaceutical product recognizing unit 823 according to the present embodiment, recognition can also be performed solely based on a linear relationship of an arrangement order of a local feature generated from a matching medical article and a local feature generated from an image in a video. Meanwhile, while a description has been given based on a two-dimensional image in the present embodiment, a similar process can also be performed using a three-dimensional feature point coordinate.

Hardware Configuration of Communication Terminal

Figure 12A:
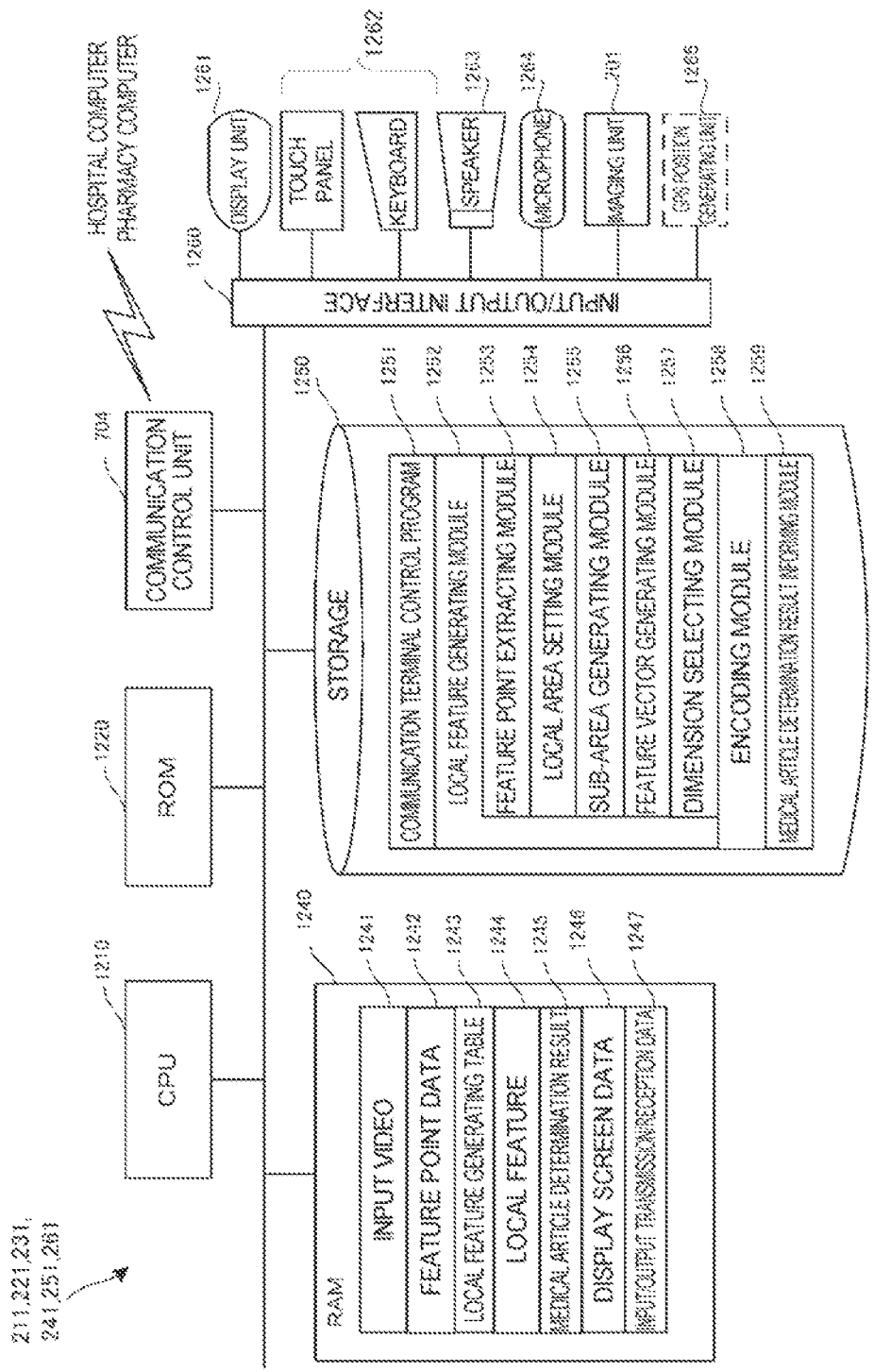
FIG. 12A is a block diagram showing a hardware configuration of the communication terminal according to the second embodiment of the present invention.

FIG. 12A is a block diagram showing a hardware configuration of the communication terminals 211 to 261 according to the present embodiment.

In FIG. 12A, a CPU 1210 is an arithmetic control processor which realizes the respective functional constituents of the communication terminals 211 to 261 by executing a program. A ROM 1220 stores initial data, fixed data of a program or the like, and a program. In addition, the communication control unit 704 is a communication control unit which, in the present embodiment, communicates with the hospital computer 201a or the pharmacy computer 202a via a network. Moreover, the CPU 1210 is not limited to one unit and a plurality of CPUs may be provided or a GPU (Graphics Processing Unit) for image processing may be provided.

A RAM 1240 is a random access memory that is used by the CPU 1210 as a work area for temporary storage. An area for storing data necessary for realizing the present embodiment is secured in the RAM 1240. An input video 1241 represents an input video captured and inputted by the imaging unit 701. Feature point data 1242 represents feature point data including a feature point coordinate, a scale, and an angle detected from the input video 1241. A local feature generating table 1243 represents a local feature generating table that retains data until a local feature is generated (refer to 12B). A local feature 1244 is generated using the local feature generating table 1243 and represents a local feature that is sent via the communication control unit 704 to a transmission destination that performs recognition and determination of a medical article. A medical article determination result 1245 represents a medical article determination result that is sent back via the communication control unit 704 from the transmission destination. Display screen data 1246 represents display screen data for informing information including the medical article determination result 1245 to a user. Moreover, in a case where audio output is provided, the display screen data 1246 may include audio data. Input/output transmission/reception data 1247 represents input/output data that is inputted/outputted via an input/output interface 1260 and transmission/reception data that is transmitted/received via the communication control unit 704.

A storage 1250 stores databases and various parameters or data or programs described below which are necessary for realizing the present embodiment. The storage 1250 stores the following programs. A communication terminal control program 1251 represents a communication terminal control program that is responsible for overall control of the present communication terminals 211 to 261. The communication terminal control program 1251 includes the following modules.

In the communication terminal control program 1251, a local feature generating module 1252 is a module that generates a local feature from an input video according to FIGS. 11B to 11F. An encoding module 1258 is a module for encoding the local feature generated by the local feature generating module 1252 for transmission. A medical article determination result informing module 1259 is a module for receiving a medical article determination result and informing the medical article determination result to a user by means of display or audio.

The input/output interface 1260 provides an interface for input/output data with an input/output device. A display unit 1261, a touch panel or a keyboard that is an operating unit 1262, a speaker 1263, a microphone 1264, and the imaging unit 701 are connected to the input/output interface 1260. Input/output devices are not limited to the examples given above. In addition, if necessary, a GPS (Global Positioning System) position generating unit 1265 is mounted and a current position is acquired based on a signal from a GPS satellite.

It should be noted that FIG. 12A only shows data and programs essential to the present embodiment and, as such, data and programs not related to the present embodiment are not shown.

Local Feature Generating Table

FIG. 12B is a diagram showing the local feature generating table 1243 of the communication terminals 211 to 261 according to the present embodiment.

The local feature generating table 1243 stores, in association with an input image ID 1201, a plurality of detected feature points 1202 which have been detected, feature point coordinates 1203, and local area information 1204 corresponding to the feature points. Furthermore, in association with each detected feature point 1202, the feature point coordinate 1203, and the local area information 1204, a plurality of sub-area IDs 1205, sub-area information 1206, a feature vector 1207 corresponding to each sub-area, and a selection dimension 1208 including a priority order are stored.

From the data described above, a local feature 1209 is generated for each detected feature point 1202.

Processing Procedure of Communication Terminal

Figure 13:
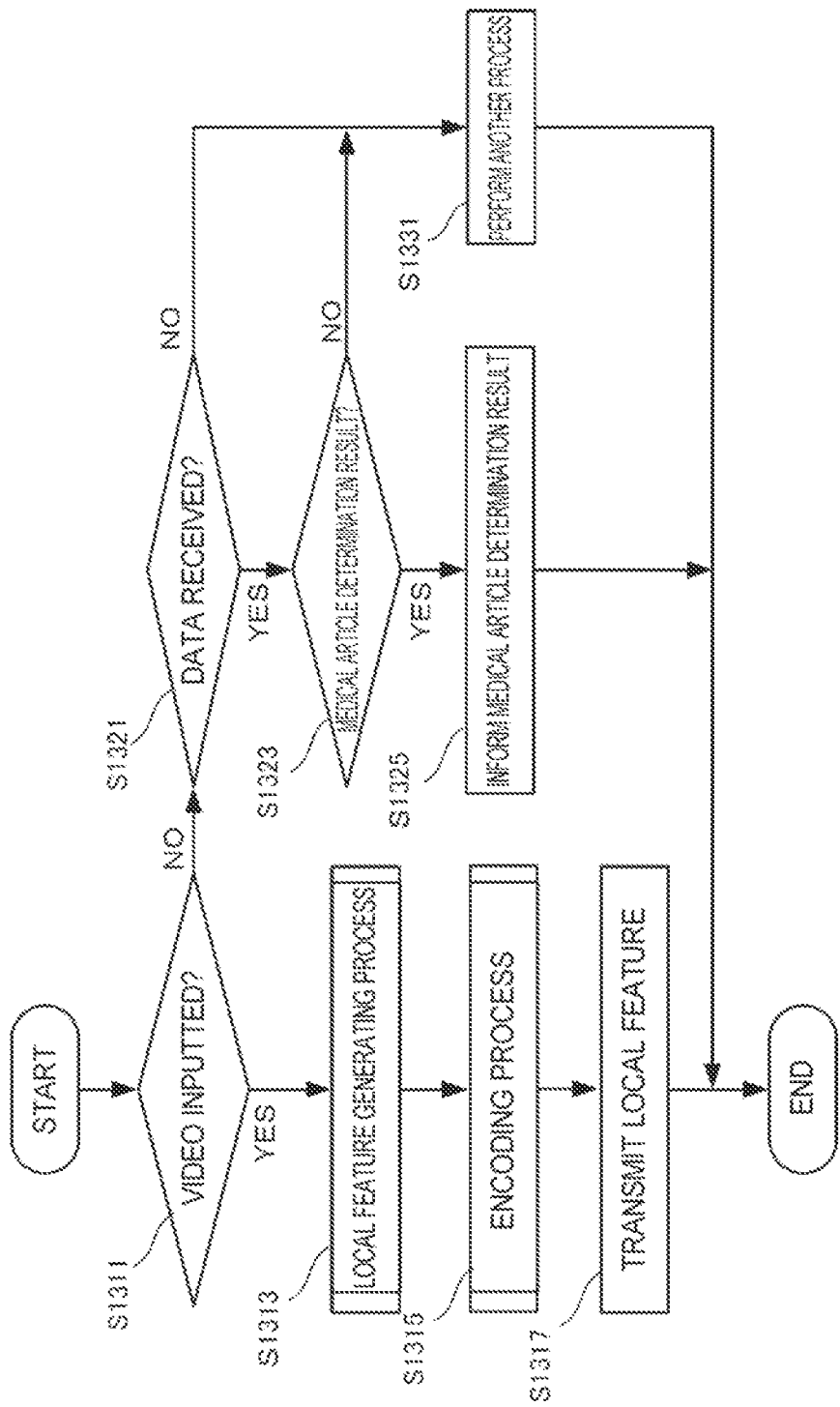
FIG. 13 is a flow chart showing a processing procedure of the communication terminal according to the second embodiment of the present invention.

FIG. 13 is a flow chart showing a processing procedure of the communication terminals 211 to 261 according to the present embodiment. The flow chart is executed by the CPU 1210 shown in FIG. 12A using the RAM 1240 and realizes the respective functional constituents shown in FIG. 7.

First, in step S1311, a determination is made as to whether or not there has been a video input in order to perform recognition of a medical article. In addition, in step S1321, data reception is determined. If neither, another process is performed in step S1331. Moreover, a description of a normal transmitting process will be omitted.

Figure 14A:
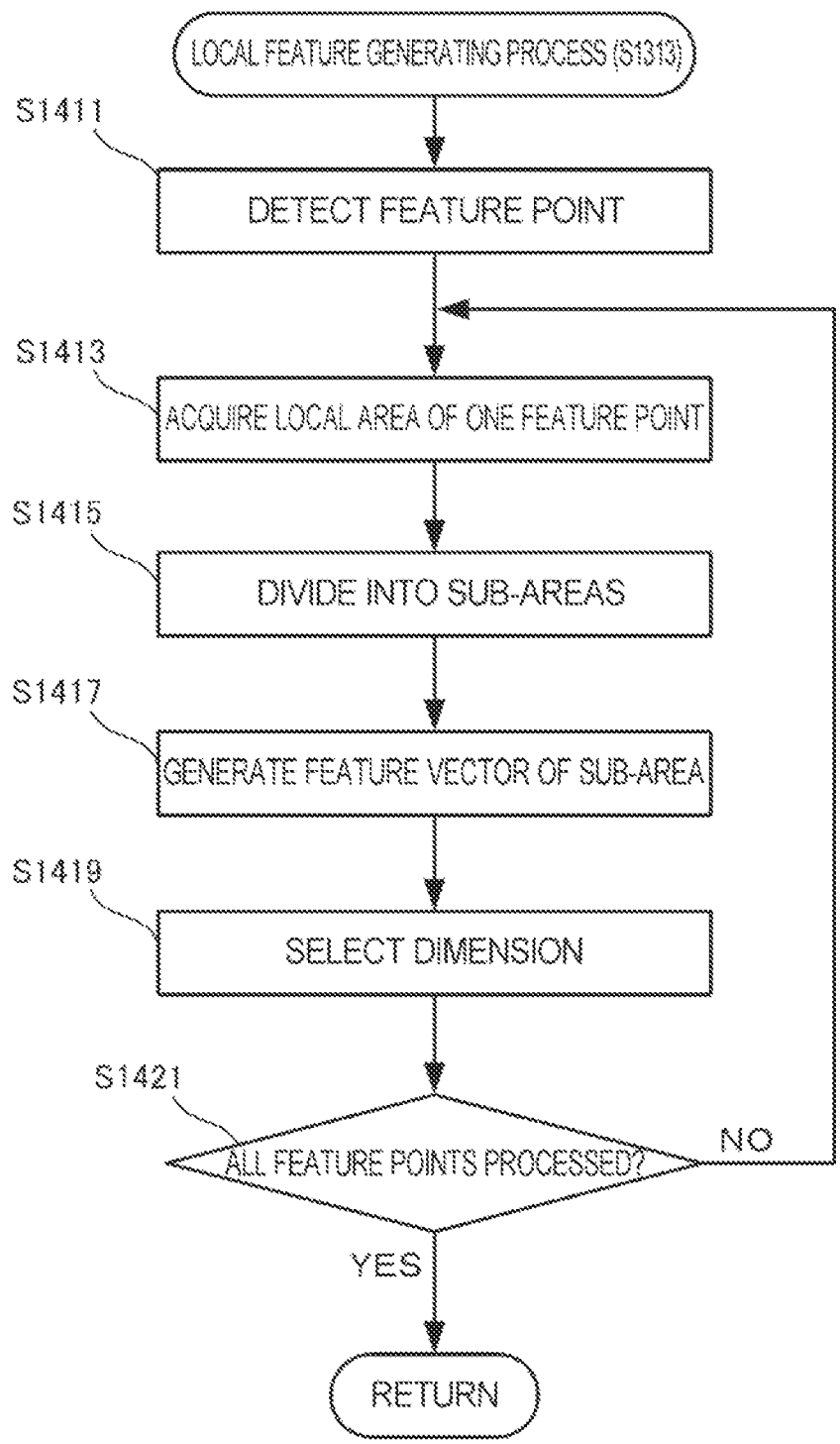
FIG. 14A is a flow chart showing a processing procedure of a local feature generating process according to the second embodiment of the present invention.

If there has been a video input, the procedure advances to step S1313 to execute a local feature generating process from the input video (refer to FIG. 14A). Next, in step S1315, a local feature and a feature point coordinate are encoded (refer to FIGS. 14B and 14C). In step S1317, the encoded data is transmitted to the hospital computer 201a or the pharmacy computer 202a.

In a case of data reception, the procedure advances to step S1323 to determine whether or not reception of a medical article determination result from the hospital computer 201a or the pharmacy computer 202a has been performed. In a case of reception of a medical article determination result, the procedure advances to step S1325 to inform the received medical article determination result.

Local Feature Generating Process

FIG. 14A is a flow chart showing a processing procedure of the local feature generating process S1313 according to the present embodiment.

First, in step S1411, a position coordinate, a scale, and an angle of feature points are detected from the input video. In step S1413, a local area is acquired with respect to one of the feature points detected in step S1411. Next, in step S1415, the local area is divided into sub-areas. In step S1417, a feature vector of each sub-area is generated to generate a feature vector of the local area. The processes of steps S1411 to S1417 are illustrated in FIG. 11B.

Next, in step S1419, dimension selection is executed with respect to the feature vector of the local area generated in step S1417. The dimension selection is illustrated in FIGS. 11D to 11F.

In step S1421, a determination is made on whether local feature generation and dimension selection have been completed with respect to all feature points detected in step S1411. If not, the procedure returns to step S1413 to repeat the processes with respect to a next feature point.

Encoding Process

Figure 14B:
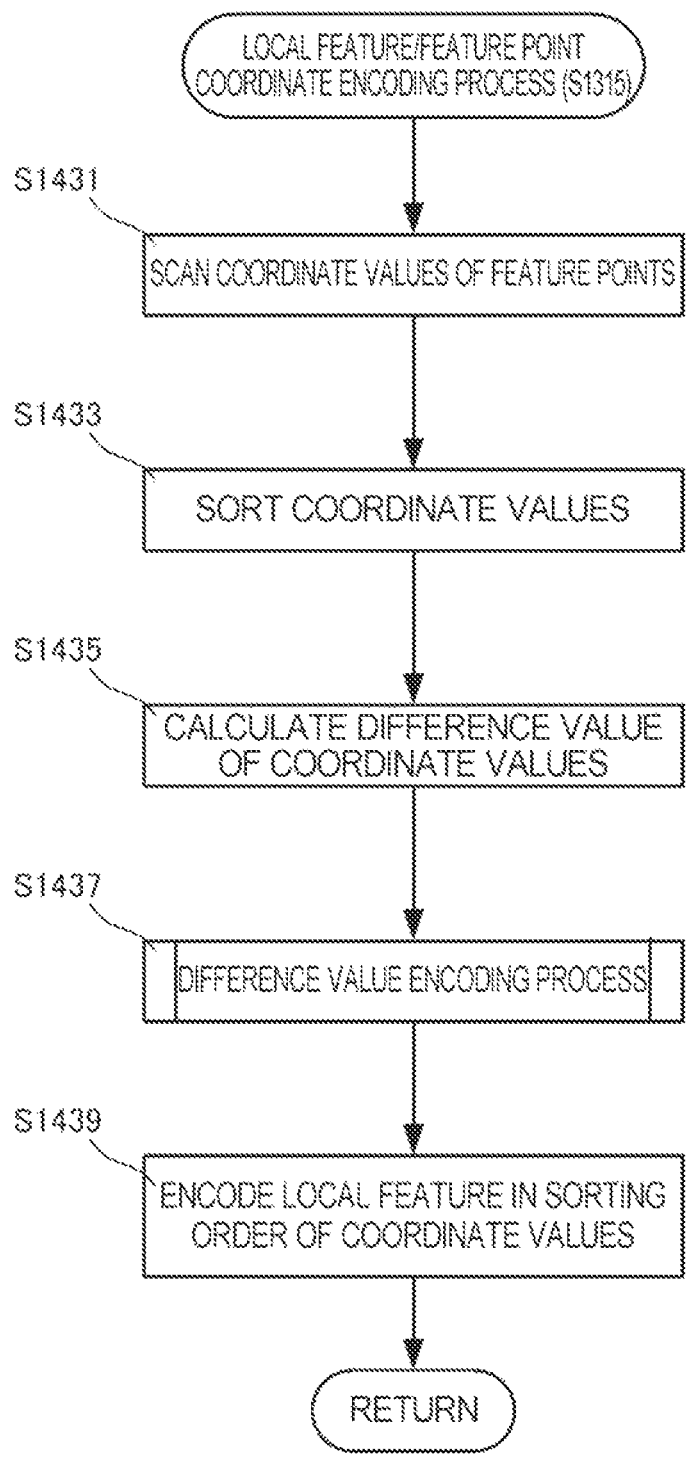
FIG. 14B is a flow chart showing a processing procedure of an encoding process according to the second embodiment of the present invention.

FIG. 14B is a flow chart showing a processing procedure of the encoding process S1315 according to the present embodiment.

First, in step S1431, coordinate values of feature points are scanned in a desired order. Next, in step S1433, the scanned coordinate values are sorted. In step S1435, difference values of the coordinate values are calculated in the sorting order. In step S1437, the difference values are encoded (refer to FIG. 14C). In addition, in step S1439, local features are encoded in the sorting order of the coordinate values. Moreover, encoding of the difference values and encoding of the local features may be performed in parallel.

Difference Value Encoding Process

Figure 14C:
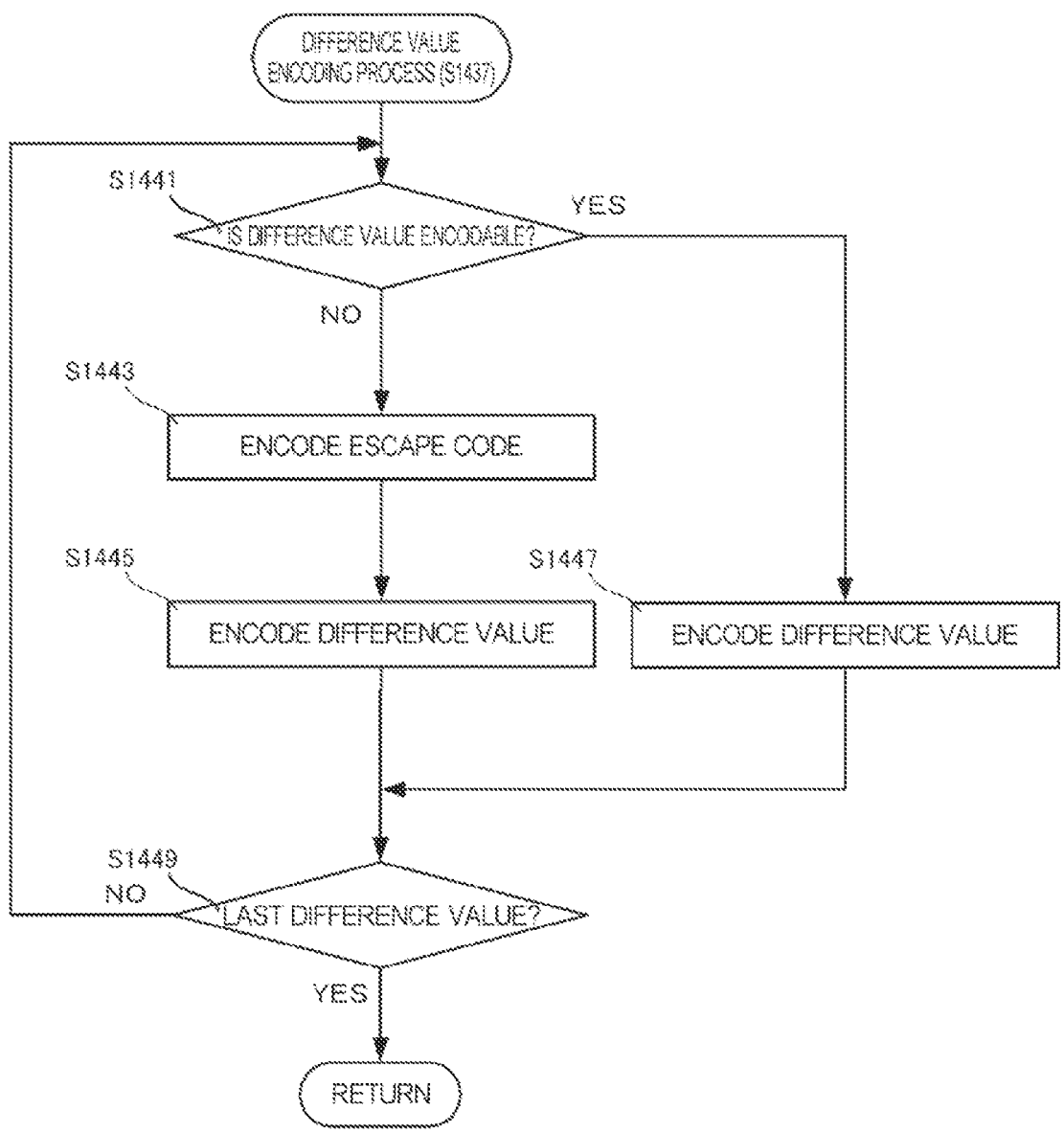
FIG. 14C is a flow chart showing a processing procedure of an encoding process of a difference value according to the second embodiment of the present invention.

FIG. 14C is a flow chart showing a processing procedure of the difference value encoding process S1437 according to the present embodiment.

First, in step S1441, a determination is made on whether or not a difference value is within an encodable range. If the difference value is within an encodable range, the procedure advances to step S1447 to encode the difference value. Subsequently, a transition is made to step S1449. If the difference value is not within an encodable range (out of range), the procedure advances to step S1443 to encode an escape code. In addition, in step S1445, the difference value is encoded using a different encoding method from the encoding in step S1447. Subsequently, a transition is made to step S1449. In step S1449, a determination is made on whether or not the processed difference value is a last element in a series of difference values. If so, the process is completed. If not, the procedure returns to step S1441 to execute the process on a next difference value in the series of difference values.

Hardware Configuration of Hospital Computer

FIG. 15 is a block diagram showing a hardware configuration of the hospital computer 201a according to the present embodiment.

In FIG. 15, a CPU 1510 is an arithmetic control processor which realizes the respective functional constituents of the hospital computer 201a by executing a program. A ROM 1520 stores initial data, fixed data of a program or the like, and a program. In addition, the communication control unit 811 is a communication control unit which, in the present embodiment, communicates with a communication terminal or the pharmacy computer 202a via a network. Moreover, the CPU 1510 is not limited to one unit and a plurality of CPUs may be provided or a GPU for image processing may be provided.

A RAM 1540 is a random access memory that is used by the CPU 1510 as a work area for temporary storage. An area for storing data necessary for realizing the present embodiment is secured in the RAM 1540. A received local feature 1541 represents a local feature including a feature point coordinate received from the communication terminal. A read local feature 1542 represents a local feature including a feature point coordinate read from the local feature DB 410. A medical article recognition result 1543 represents a medical article recognition result that is recognized by collating the received local feature with a local feature stored in the local feature DB 410. A medical article arrangement determination result 1544 represents a medical article arrangement determination result that is a determined arrangement of a medical device or a surgical instrument. A number of recognized medical articles 1545 particularly represents the number of medical articles 1545 that are the number of recognized surgical instruments. Transmission/reception data 1547 represents transmission/reception data that is transmitted/received via the communication control unit 811.

A storage 1550 stores databases and various parameters or data or programs described below which are necessary for realizing the present embodiment. The local feature DB 410 represents a local feature DB similar to that shown in FIG. 9A. The medical device DB 420 represents a medical device DB similar to that shown in FIG. 9B. The surgical instrument DB 530 represents a surgical instrument DB similar to that shown in FIG. 9C.

The storage 1550 stores the following programs. A hospital computer control program 1551 represents a hospital computer control program that controls all computers of the present hospital. A local feature DB creating module 1552 is a module in the hospital computer control program 1551 which generates a local feature from an image of a medical article and stores the local feature in a local feature DB. A medical article recognizing module 1553 is a module in the hospital computer control program 1551 which collates a received local feature with a local feature stored in the local feature DB 410 to recognize a medical article. A medical device arrangement/status determining module 1554 is a module in the hospital computer control program 1551 which determines an arrangement or a status based on a medical device recognized from a local feature. A surgical instrument arrangement/status determining module 1555 is a module in the hospital computer control program 1551 which determines an arrangement or a status based on a surgical instrument recognized from a local feature. A determination result transmitting module 1556 is a module in the hospital computer control program 1551 which transmits a determination result to a communication terminal or a center PC.

It should be noted that FIG. 15 only shows data and programs essential to the present embodiment and, as such, data and programs not related to the present embodiment are not shown.

Processing Procedure of Hospital Computer

FIG. 16 is a flow chart showing a processing procedure of the hospital computer 201a according to the present embodiment. The flow chart is executed by the CPU 1510 shown in FIG. 15 using the RAM 1540 and realizes the respective functional constituents shown in FIG. 8A.

First, in step S1611, a determination is made on whether or not generation of a local feature DB is to be performed. In addition, in step S1621, a determination is made on whether or not local feature reception from a communication terminal has been performed. If neither, another process is performed in step S1641.

Figure 17:
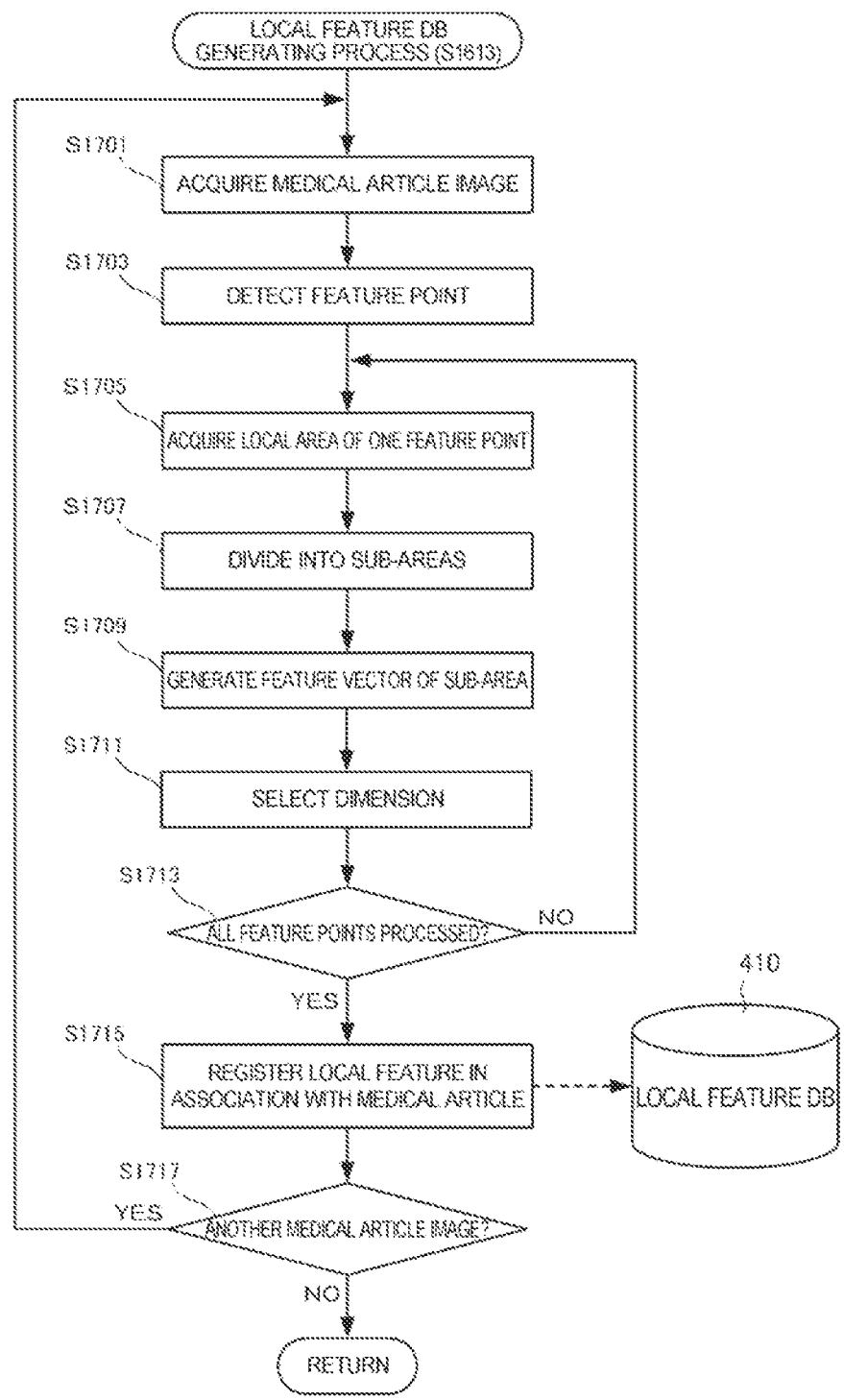
FIG. 17 is a flow chart showing a processing procedure of a local feature DB generating process according to the second embodiment of the present invention.

In case of generation of a local feature DB, the procedure advances to step S1613 to execute a local feature DB generating process (refer to FIG. 17). In addition, in case of reception of a local feature, the procedure advances to step S1623 to perform a medical article recognizing process (refer to FIGS. 18A and 18B).

Next, in step S1625, a determination is made on whether the recognized medical article is a medical device or a surgical instrument. If the recognized medical article is a medical device, the procedure advances to step S1627 to reference the medical device DB 420 (FIG. 9B) and determine an arrangement and a status of the medical device. Subsequently, in step S1629, a determination result is transmitted. On the other hand, if the recognized medical article is a surgical instrument, the procedure advances to step S1631 to reference the surgical instrument DB 530 (FIG. 9C) and determine an arrangement, the number, and propriety of the surgical instrument. Subsequently, in step S1633, a determination result is transmitted.

Moreover, while medical articles have been represented by a medical device and a surgical instrument, a document such as a medical record or other articles may be recognized and determined. In addition, an accuracy of a local feature in the determining processes of steps S1627 and S1631 may be set higher than an accuracy of a local feature in the recognizing process of step S1623.

Local Feature DB Generating Process

FIG. 17 is a flow chart showing a processing procedure of the local feature DB generating process S1613 according to the present embodiment.

First, in step S1701, an image of a medical article is acquired. In step S1703, a position coordinate, a scale, and an angle of feature points are detected. In step S1705, a local area is acquired with respect to one of the feature points detected in step S1703. Next, in step S1707, the local area is divided into sub-areas. In step S1709, a feature vector of each sub-area is generated to generate a feature vector of the local area. The processes of steps S1705 to S1709 are illustrated in FIG. 11B.

Next, in step S1711, dimension selection is executed with respect to the feature vector of the local area generated in step S1709. The dimension selection is illustrated in FIGS. 11D to 11F. However, while hierarchization is executed upon dimension selection in the generation of the local feature DB 410, all of the generated feature vectors are desirably stored.

In step S1713, a determination is made on whether local feature generation and dimension selection have been completed with respect to all feature points detected in step S1703. If not, the procedure returns to step S1705 to repeat the processes with respect to a next feature point. If so, the procedure advances to step S1715 to register a local feature and a feature point coordinate in the local feature DB 410 in association with a medical article.

In step S1717, a determination is made on whether or not there is an image of another medical article. If there is an image of another medical article, the procedure returns to step S1701 to acquire the image of another medical article and repeat the process.

Medical Article Recognizing Process

Figure 18A:
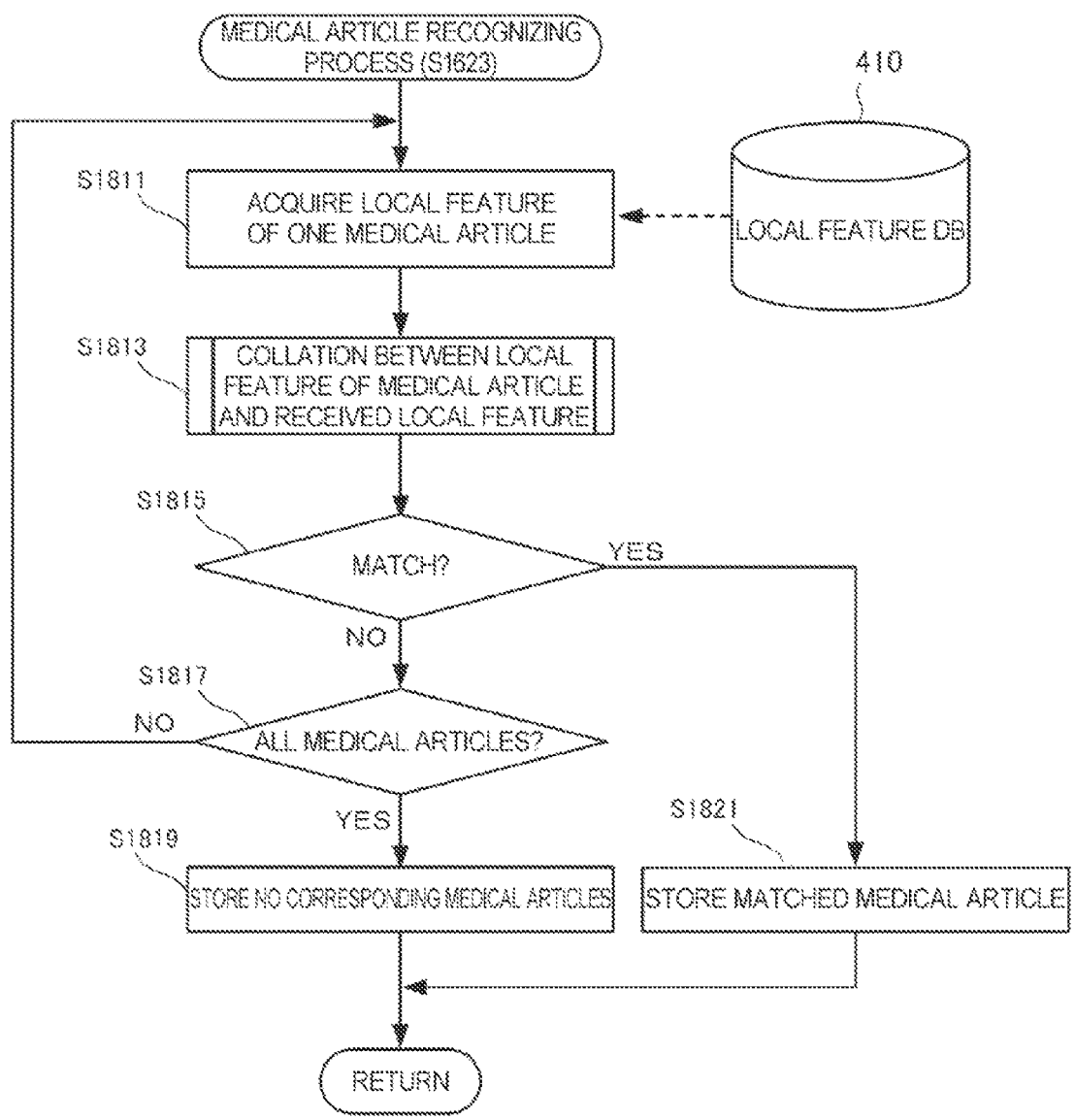
FIG. 18A is a flow chart showing a processing procedure of a medical article recognizing process according to the second embodiment of the present invention.

FIG. 18A is a flow chart showing a processing procedure of the medical article recognizing process S1623 according to the present embodiment.

First, in step S1811, a local feature of one medical article is acquired from the local feature DB 410. Subsequently, in step S1813, collation is performed between the local feature of the medical article and a local feature received from a communication terminal (refer to FIG. 18B).

In step S1815, a determination is made on whether or not the local features match. In case of a match, the procedure advances to step S1821 and stores the matching medical article on the assumption that the medical article exists in a video.

In step S1817, a determination is made on whether all medical articles registered in the local feature DB 410 have been collated and, if not, the procedure returns to step S1811 to repeat collation of a next medical article. Moreover, in performing the collation, a field limitation may be applied in advance in order to realize real-time processing by improving processing speed or to reduce processing load on a hospital computer.

Collating Process

Figure 18B:
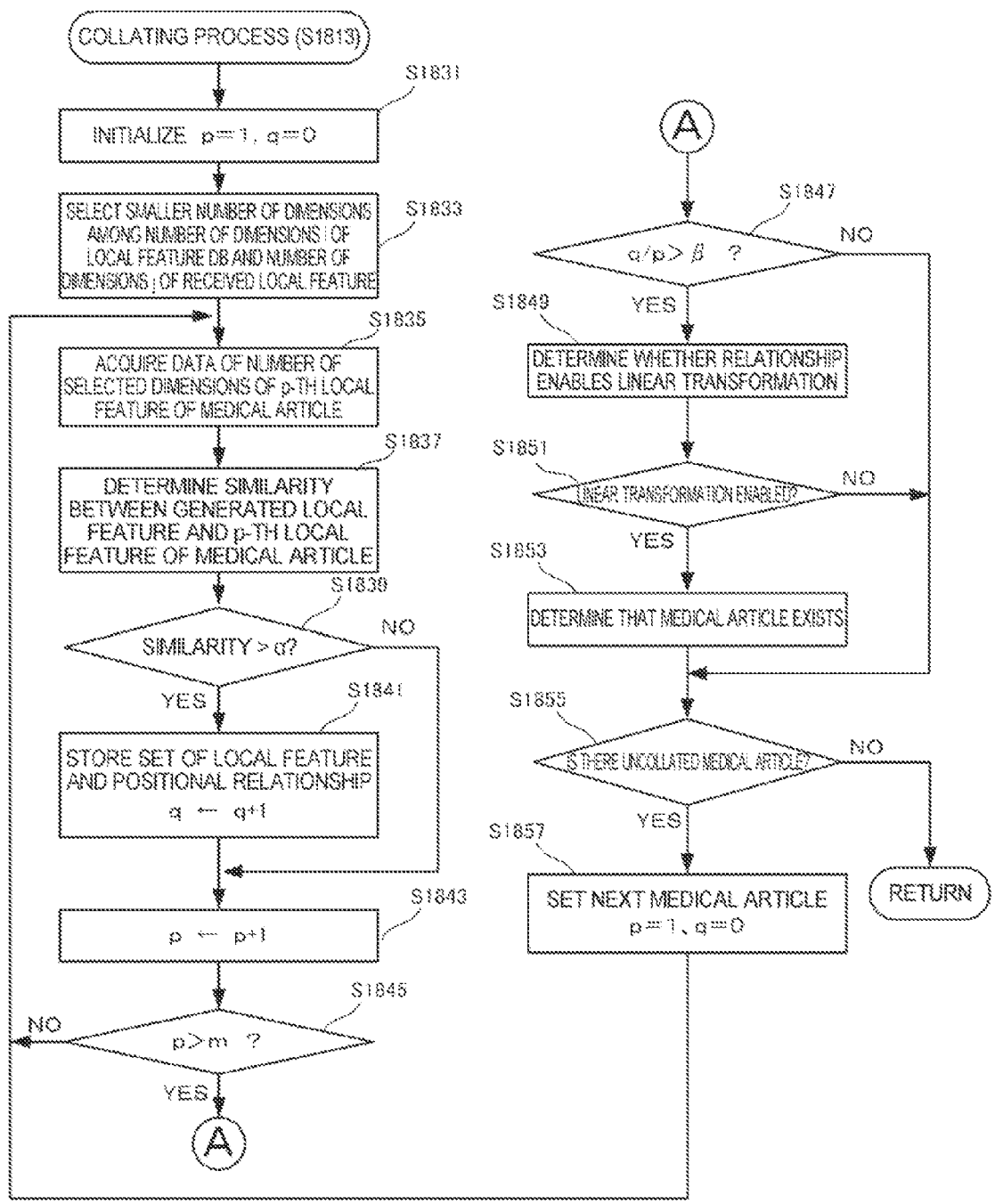
FIG. 18B is a flow chart showing a processing procedure of a collating process according to the second embodiment of the present invention.

FIG. 18B is a flow chart showing a processing procedure of the collating process S1813 according to the present embodiment.

First, in step S1831, parameters p=1 and q=0 are set as initialization. Next, in step S1833, whichever is smaller between the number of dimensions i of a local feature in the local feature DB 410 and the number of dimensions j of a received local feature is selected.

In a loop constituted by steps S1835 to S1845, collation of each local feature is repeated until p>m (m=the number of feature points of a medical article). First, in step S1835, data of the number of selected dimensions of a p-th local feature of a medical article stored in the local feature DB 410 is acquired. In other words, the number of selected dimensions is acquired starting from the 1st dimension. Next, in step S1837, the p-th local feature acquired in step S1835 and local features of all feature points generated from an input video are sequentially collated with each other to determine whether or not the local features are similar. In step S1839, a determination is made on whether or not a result of collation between local features exceeds a threshold $\alpha$ and, if so, in step S1841, a set of the local feature and a positional relationship of feature points that match between the input video and the medical article is stored. Subsequently, q that is a parameter representing the number of matched feature points is counted up by one. In step S1843, the feature point of the medical article is advanced to a next feature point (p←p+1), and when collation of all feature points of the medical article is not completed (p≤m), the procedure returns to step S1835 to repeat collation of matching local features. Moreover, the threshold $\alpha$ can be modified in accordance with a recognition accuracy that is required by the medical article. In a case of a medical article with a low correlation with another medical article, accurate recognition can be realized even when recognition accuracy is lowered.

Once collation with all feature points of the medical article is completed, the procedure advances from step S1845 to S1847. In steps S1847 to S1853, a determination is made on whether or not the medical article exists in the input video. First, in step S1847, a determination is made on whether or not a ratio of the number of feature points q matching a local feature of a feature point of the input image among the number of feature points p of the medical article exceeds a threshold $\rho$. If so, the procedure advances to step S1849 to further determine, as a medical article candidate, whether the positional relationship between a feature point of the input video and a feature point of the medical article is a relationship that enables linear transformation. In other words, a determination is made on whether or not the positional relationship between a feature point of the input video and a feature point of the medical article which has been stored in step S1841 as having matching local features is a positional relationship that remains intact even after a change such as rotation, inversion, or modification of a viewpoint position or a positional relationship that cannot be modified. Since such a determination method is geometrically known, a detailed description thereof will be omitted. In step S1851, as a result of the determination on whether or not linear transformation is enabled, when it is found that linear transformation is enabled, the procedure advances to step S953 and a determination is made that the collated medical article exists in the input video. Moreover, the threshold $\beta$ can be modified in accordance with a recognition accuracy that is required by the medical article. In a case of a medical article with a low correlation with another medical article or a medical article that enables a feature thereof to be determined from a part of the medical article, accurate recognition can be performed even when the number of matching feature points is low. In other words, recognition of a medical article can be realized even if a part of the medical article is hidden from view or as long as a characteristic part of the medical article is visible.

In step S1855, a determination is made on whether or not an uncollated medical article remains in the local feature DB 410. If an uncollated medical article remains, a next medical article is set in step S957, the parameters are initialized to p=1 and q=0, and the procedure returns to step S935 to repeat collation.

Moreover, as is apparent from the description of the collating process given above, a process involving storing all medical articles in the local feature DB 410 and collating all medical articles significantly increases processing load. Therefore, for example, a user may conceivably select a range of medical articles from a menu prior to medical article recognition from an input video, in which case collation is performed by searching the range from the local feature DB 410. Alternatively, processing load can also be reduced by storing only local features of a range used by a user in the local feature DB 410.

Hardware Configuration of Pharmacy Computer

Figure 19:
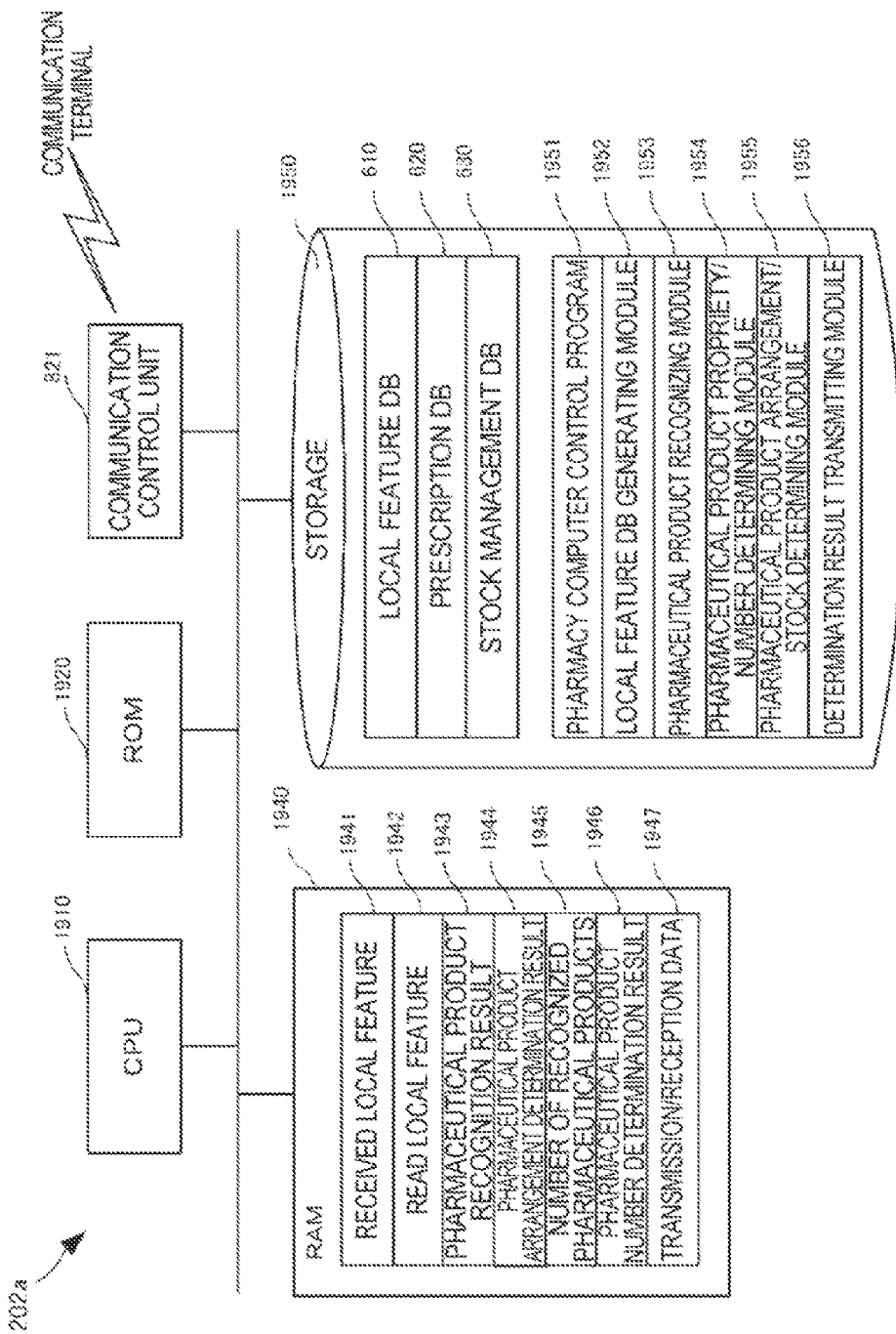
FIG. 19 is a block diagram showing a hardware configuration of a pharmacy computer according to the second embodiment of the present invention.

FIG. 19 is a block diagram showing a hardware configuration of the pharmacy computer 202a according to the present embodiment.

In FIG. 19, a CPU 1910 is an arithmetic control processor which realizes the respective functional constituents of the pharmacy computer 202a by executing a program. A ROM 1920 stores initial data, fixed data of a program or the like, and a program. In addition, the communication control unit 821 is a communication control unit which, in the present embodiment, communicates with a communication terminal or the hospital computer 201a via a network. Moreover, the CPU 1910 is not limited to one unit and a plurality of CPUs may be provided or a GPU for image processing may be provided.

A RAM 1940 is a random access memory that is used by the CPU 1910 as a work area for temporary storage. An area for storing data necessary for realizing the present embodiment is secured in the RAM 1940. A received local feature 1941 represents a local feature including a feature point coordinate received from the communication terminal. A read local feature 1942 represents a local feature including a feature point coordinate read from the local feature DB 610. A pharmaceutical product recognition result 1943 represents a pharmaceutical product recognition result that is recognized by collating the received local feature with a local feature stored in the local feature DB 610. A pharmaceutical product arrangement determination result 1944 represents a pharmaceutical product arrangement determination result that is a determined arrangement of a pharmaceutical product. The number of recognized pharmaceutical products 1945 represents the number of pharmaceutical products. A pharmaceutical product number determination result 1946 represents a determination result of a determination made on whether or not the number of pharmaceutical products 1945 is consistent with the number that is described on a prescription. Transmission/reception data 1947 represents transmission/reception data that is transmitted/received via the communication control unit 821.

A storage 1950 stores databases and various parameters or data or programs described below which are necessary for realizing the present embodiment. The local feature DB 610 represents a local feature DB similar to that shown in FIG. 10A. The prescription DB 620 represents a prescription DB similar to that shown in FIG. 10B. The stock management DB 630 represents a stock management DB similar to that shown in FIG. 10C.

The storage 1950 stores the following programs. A pharmacy computer control program 1951 represents a pharmacy computer control program that controls all computers of the present pharmacy. A local feature DB creating module 1952 is a module in the pharmacy computer control program 1951 which generates a local feature from an image of a pharmaceutical product and stores the local feature in the local feature DB 610. A pharmaceutical product recognizing module 1953 is a module in the pharmacy computer control program 1951 which collates a received local feature with a local feature stored in the local feature DB 610 to recognize a pharmaceutical product. A pharmaceutical product propriety/number determining module 1954 is a module in the pharmacy computer control program 1951 which determines propriety or the number based on a pharmaceutical product recognized from a local feature. A pharmaceutical product arrangement/stock determining module 1955 is a module in the pharmacy computer control program 1951 which performs an arrangement determination and stock management of a medicine shelf based on a pharmaceutical product recognized from a local feature. A determination result transmitting module 1956 is a module in the pharmacy computer control program 1951 which transmits a determination result to a communication terminal or an operator PC.

It should be noted that FIG. 19 only shows data and programs essential to the present embodiment and, as such, data and programs not related to the present embodiment are not shown.

Processing Procedure of Pharmacy Computer

Figure 20:
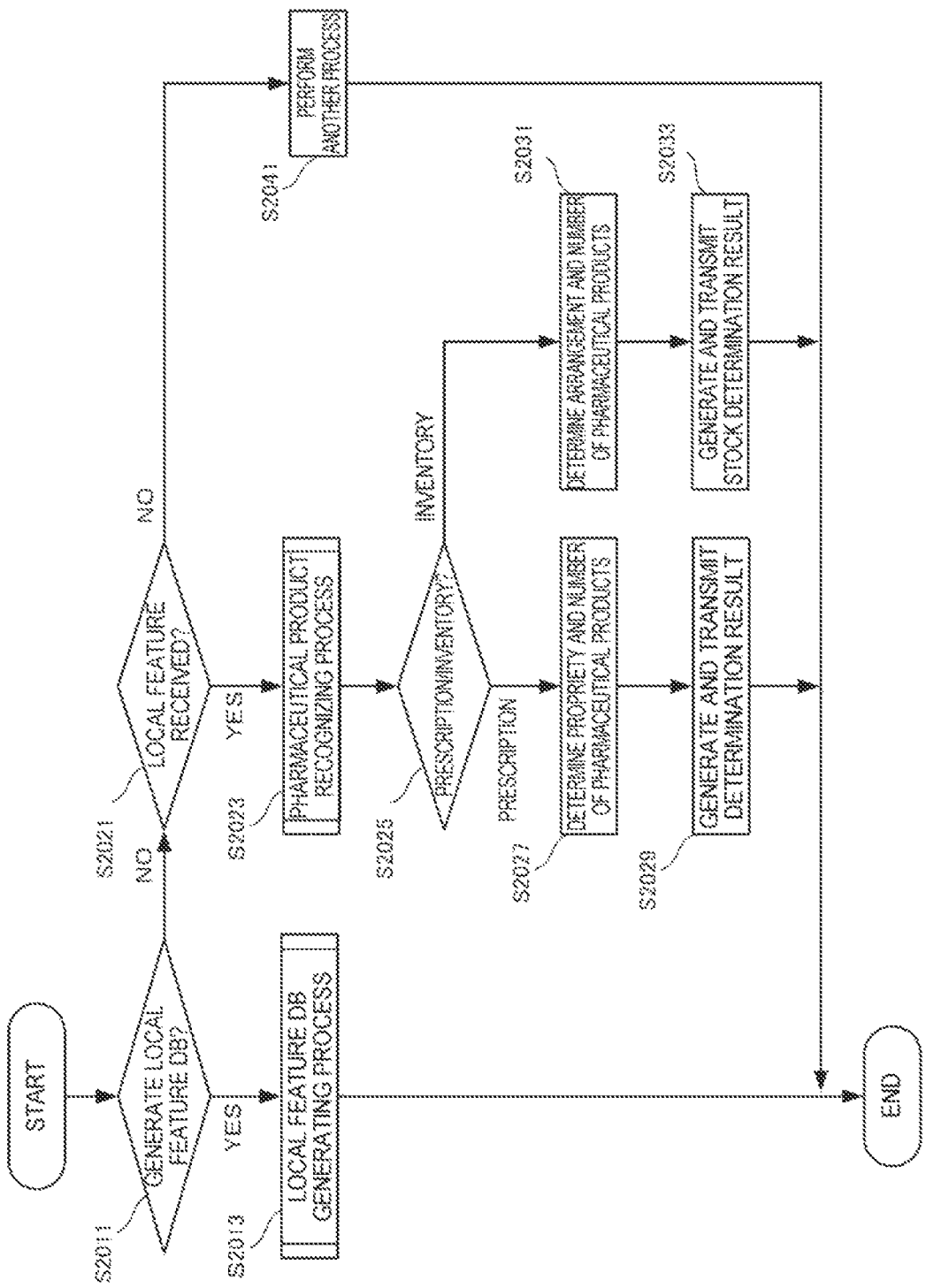
FIG. 20 is a flow chart showing a processing procedure of the pharmacy computer according to the second embodiment of the present invention.

FIG. 20 is a flow chart showing a processing procedure of the pharmacy computer 202a according to the present embodiment. The flow chart is executed by the CPU 1010 shown in FIG. 19 using the RAM 1940 and realizes the respective functional constituents shown in FIG. 8B.

First, in step S2011, a determination is made on whether or not generation of a local feature DB is to be performed. In addition, in step S2021, a determination is made on whether or not local feature reception from a communication terminal has been performed. If neither, another process is performed in step S2041.

In case of generation of a local feature DB, the procedure advances to step S2013 to execute a local feature DB generating process. On the other hand, in case of reception of a local feature, the procedure advances to step S2023 to perform a pharmaceutical product recognizing process.

Next, in step S2025, a determination is made on whether a recognized pharmaceutical product is to be subjected to a process based on a prescription or to an inventory process. In the case of a prescription, the procedure advances to step S2027 to reference the prescription DB 620 (FIG. 10B) and determine propriety and the number of the pharmaceutical products. Subsequently, in step S2029, a determination result is transmitted. On the other hand, in the case of an inventory process, the procedure advances to step S2031 to reference the stock management DB 630 (FIG. 10C) and determine an arrangement/the number of the pharmaceutical products on a medicine shelf. Subsequently, in step S2033, a determination result is transmitted.

Moreover, while medical articles have been represented by a pharmaceutical product, a document such as a prescription or other articles may be recognized and determined. In addition, an accuracy of a local feature in the determining processes of steps S2027 and S2031 may be set higher than an accuracy of a local feature in the recognizing process of step S2023.

Local Feature DB Generating Process and Medical Article Recognizing Process

Since details of the local feature DB generating process (S2013) and the medical article recognizing process (S2023) shown in FIG. 20 are similar to those shown in FIGS. 17, 18A, and 18B as long as a medical article is replaced with a pharmaceutical product, descriptions will be substituted by the descriptions of FIGS. 17, 18A, and 18B.

Third Embodiment

Next, an information processing system according to a third embodiment of the present invention will be described. The information processing system according to the present embodiment differs from the second embodiment in that an accuracy of a local feature is adjusted and a recognizing process and a determining process are performed at different accuracies. Since other configurations and operations are similar to those of the second embodiment, same configurations and operations will be denoted by same reference characters and detailed descriptions thereof will be omitted.

According to the present embodiment, a more accurate recognizing process and a more accurate determining process can be realized while improving processing speed.

Operational Procedure of Information Processing System

Figure 21:
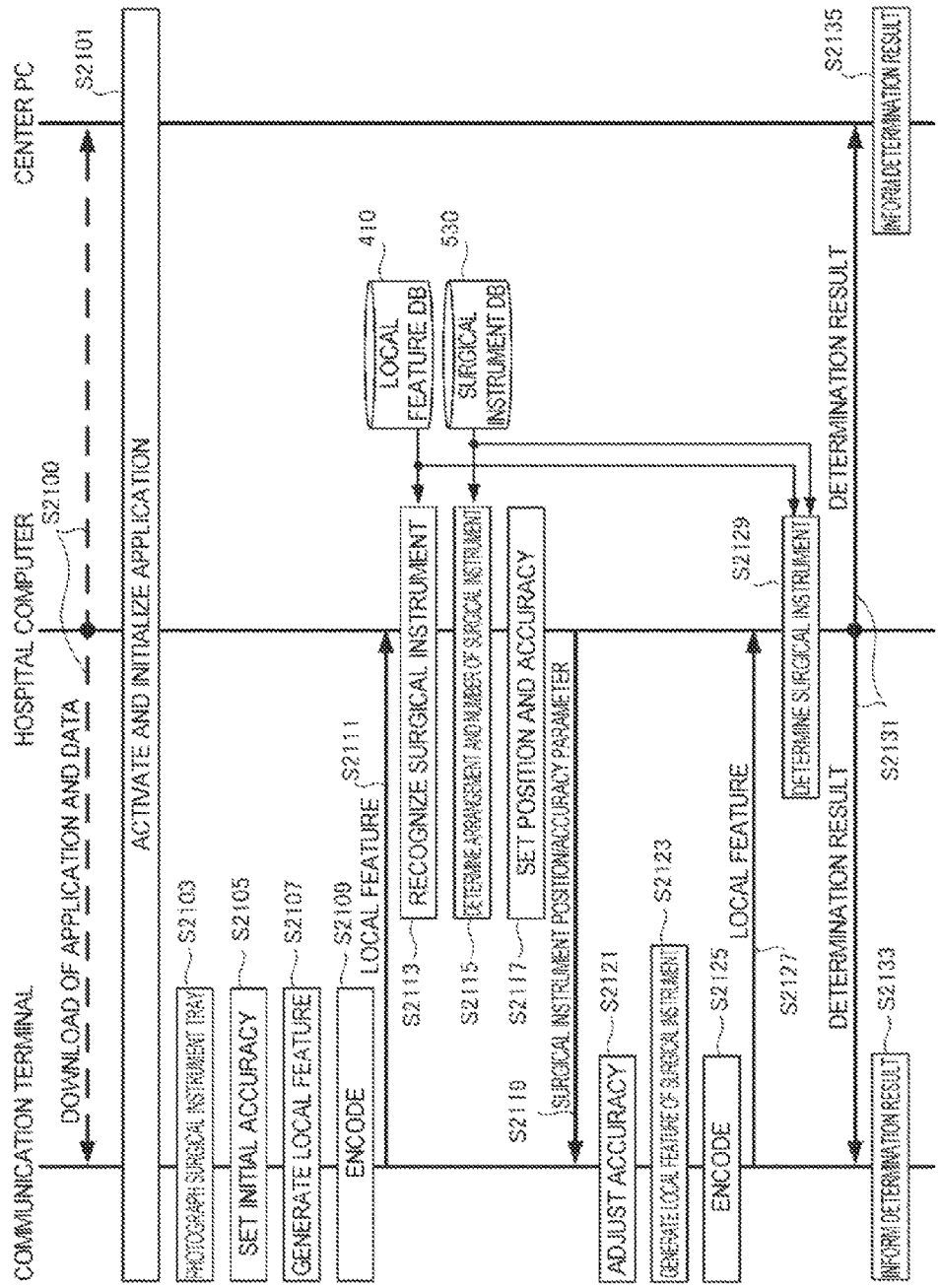
FIG. 21 is a sequence diagram showing an operational procedure of an information processing system according to a third embodiment of the present invention.

FIG. 21 is a sequence diagram showing an operational procedure of the information processing system according to the present embodiment. Moreover, while recognizing and determining processes of a surgical instrument in a surgical instrument tray in an operation room of a hospital will be representatively described with reference to FIG. 21, other processes with respect to a medicine tray or the like can also be realized by a similar procedure.

First, if necessary, in step S2100, an application and/or data is downloaded from the hospital computer 201a to a communication terminal or a center PC. In addition, in step S2101, the application is activated and initialized in order to perform processes of the present embodiment.

In step S2103, the communication terminal photographs the surgical instrument tray. Next, in step S2105, an initial accuracy of local feature generation is set. In step S2107, a local feature is generated at the initial accuracy from a video of the surgical instrument tray. Subsequently, in step S2109, the local feature is encoded together with a feature point coordinate. The encoded local feature is transmitted in step S2111 from the communication terminal to the hospital computer 201a.

In step S2113, the hospital computer 201a references a local feature DB 410 generated and stored with respect to each surgical instrument that is a medical article and performs recognition of a surgical instrument. Subsequently, in step S2115, an arrangement and the number of the surgical instruments in the surgical instrument tray which are stored in the surgical instrument DB 530 are referenced to determine whether or not an arrangement and the number of the surgical instruments are normal.

Next, in order to determine whether there is a defect in the surgical instrument itself, a determination of the surgical instrument at increased accuracy is performed by adjusting an accuracy of the local feature. To this end, in step S2117, in correspondence with a surgical instrument that requires a detailed inspection with respect to a defect, a position (an area in a video) and an adjusted accuracy are set. Subsequently, in step S2119, the set position and accuracy of the surgical instrument are transmitted to the communication terminal.

At the communication terminal, in step S2121, adjustment (setting of an accuracy parameter) is performed to the received accuracy. Next, in step S2123, a local feature of a surgical instrument at the specified position (area) is generated at increased accuracy. Subsequently, in step S2125, the local feature is encoded together with a feature point coordinate. The encoded local feature is transmitted in step S2127 from the communication terminal to the hospital computer 201a.

At the hospital computer 201a, in step S2129, a detailed propriety determination of a particular surgical instrument is performed by referencing the local feature DB 410 and the surgical instrument DB 530 with respect to the surgical instrument. Subsequently, in step S2131, a determination result of the arrangement/number of the surgical instrument in step S2115 and a detect inspection result in surgical instrument units in step S2129 are transmitted to the communication terminal and the center PC.

The communication terminal informs the received determination result in step S2133 and the center PC informs the received determination result in step S2135.

Functional Configuration of Communication Terminal

Figure 22:
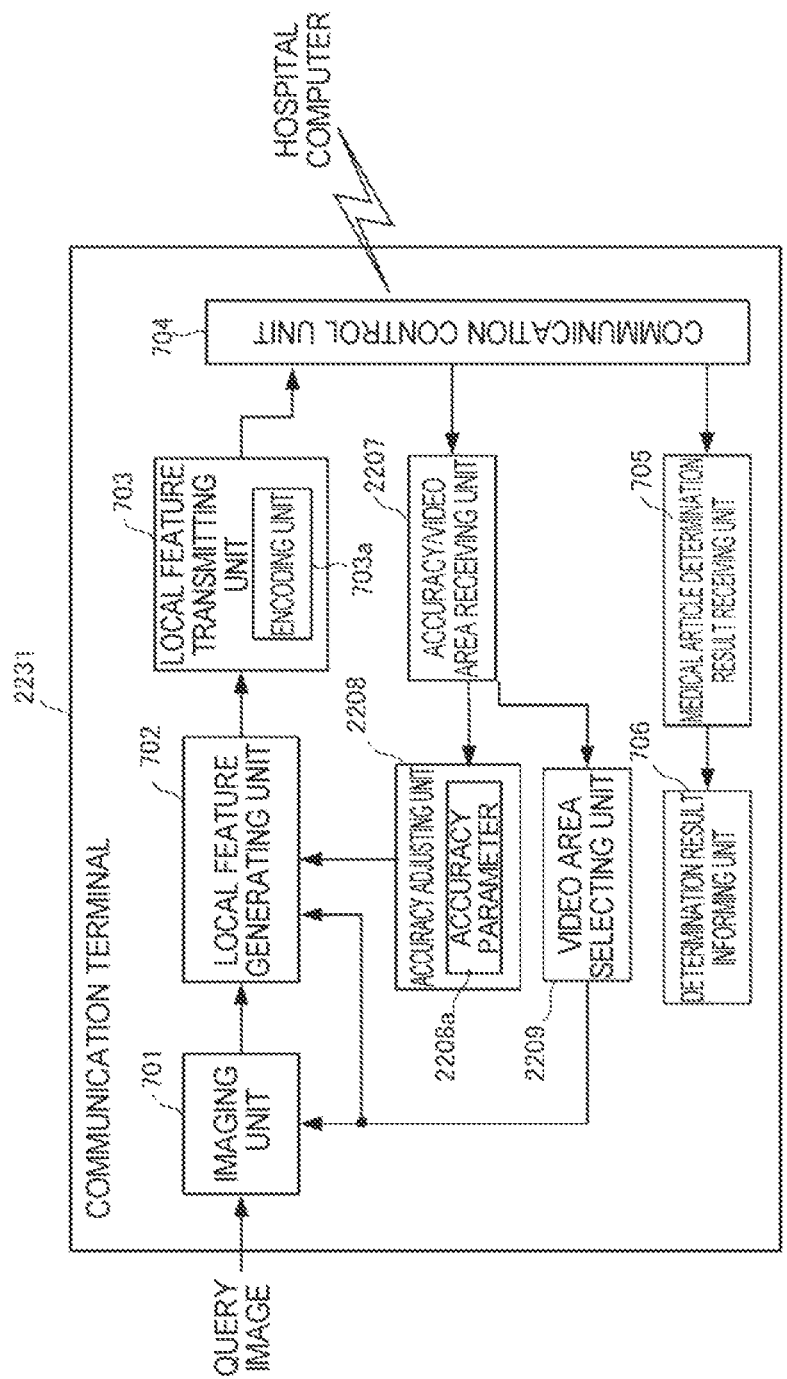
FIG. 22 is a block diagram showing a functional configuration of a communication terminal according to the third embodiment of the present invention.

FIG. 22 is a block diagram showing a functional configuration of a communication terminal according to the third embodiment of the present invention. Moreover, functional configurations similar to FIG. 7 according to the second embodiment will be denoted by same reference characters and descriptions thereof will be omitted.

An accuracy/video area receiving unit 2207 receives an accuracy parameter to be adjusted and an area (position) in a video for which a local feature is to be generated which have been transmitted from the hospital computer 201a via the communication control unit 704. An accuracy adjusting unit 2208 retains an accuracy parameter 2208a for accuracy adjustment and adjusts an accuracy of a local feature to be generated by the local feature generating unit 702 based on the accuracy parameter 2208a. In addition, a video area selecting unit 2209 selects an arrangement area of a surgical instrument that is an object in a video for which a local feature is to be generated.

Accuracy Adjusting Unit

Hereinafter, configurations of several examples of the accuracy adjusting unit 2208 will be described with reference to FIGS. 23A to 23C, 24, and 25.

First Configuration

Figure 23A:
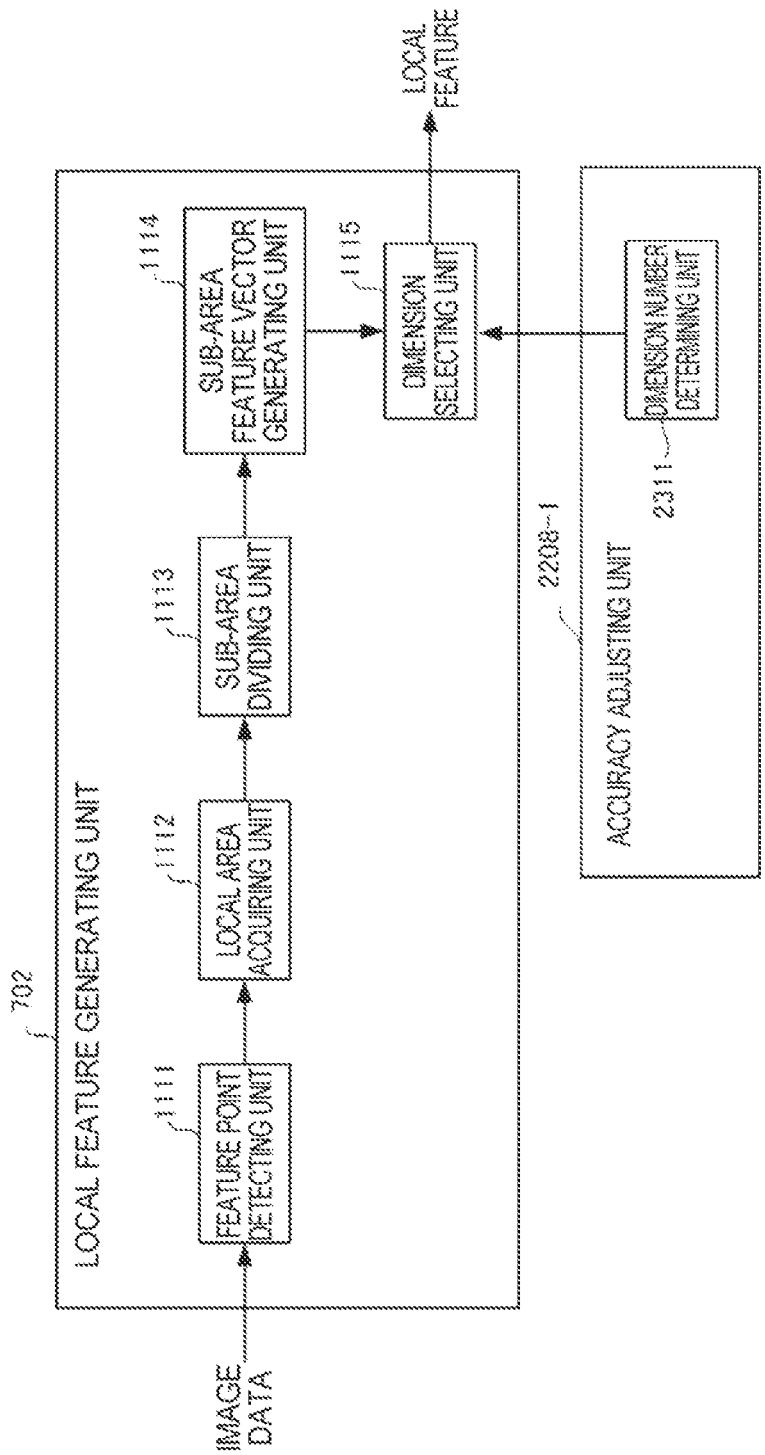
FIG. 23A is a block diagram showing a first configuration of an accuracy adjusting unit according to the third embodiment of the present invention.

FIG. 23A is a block diagram showing a first configuration 2208-1 of the accuracy adjusting unit 2208 according to the present embodiment. With the first configuration 2208-1 of the accuracy adjusting unit 2208, the number of dimensions can be determined by a dimension number determining unit 2311.

The dimension number determining unit 2311 is capable of determining the number of dimensions to be selected by the dimension selecting unit 1115. For example, by receiving information indicating the number of dimensions from a user, the dimension number determining unit 2311 can determine the number of dimensions. Moreover, the information indicating the number of dimensions need not necessarily indicate the number of dimensions itself and may be, for example, information indicating a collation accuracy and a collation speed. Specifically, for example, when an input requesting local feature generation accuracy, communication accuracy, and collation accuracy to be increased is received, the dimension number determining unit 2311 determines the number of dimensions so that the number of dimensions is increased. For example, when an input requesting local feature generation speed, communication speed, and collation speed to be increased is received, the dimension number determining unit 2311 determines the number of dimensions so that the number of dimensions is reduced.

Moreover, the dimension number determining unit 2311 may be configured to determine the same number of dimensions for all feature points detected from an image or to determine a different number of dimensions for each feature point. For example, when provided with importance of feature points by means of external information, the dimension number determining unit 2311 may increase the number of dimensions for feature points with high importance and reduce the number of dimensions for feature points with low importance. In this manner, the number of dimensions can be determined while taking into consideration collation accuracy, local feature generation speed, communication speed, and collation speed.

In the present embodiment, if conditions related to other accuracies are the same, processes can conceivably be performed for determining an appropriate number of dimensions for a medical article and changing the number of dimensions before and after the appropriate number of dimensions.

Second Configuration

Figure 23B:
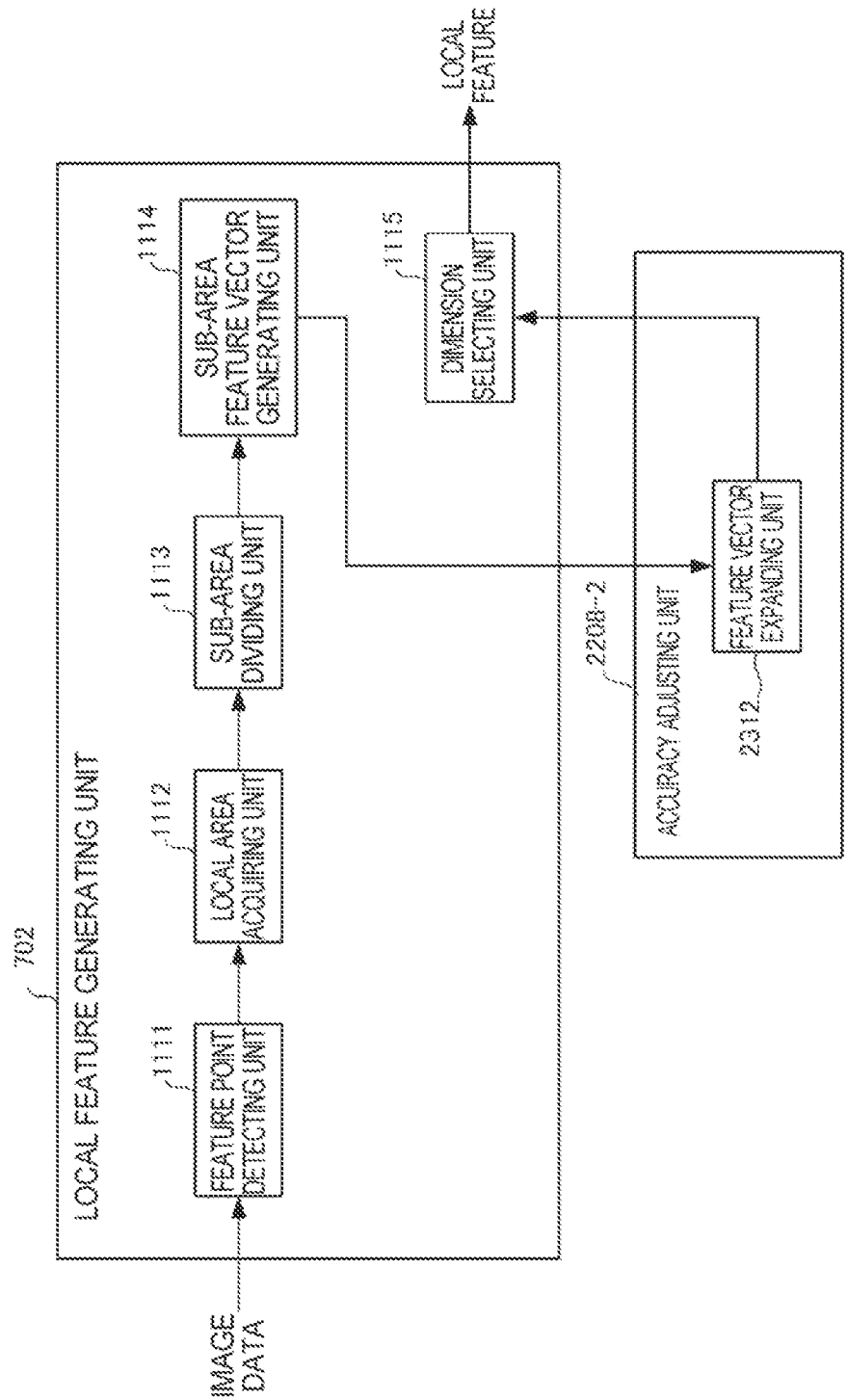
FIG. 23B is a block diagram showing a second configuration of the accuracy adjusting unit according to the third embodiment of the present invention.

FIG. 23B is a block diagram showing a second configuration 2208-2 of the accuracy adjusting unit 2208 according to the present embodiment. With the second configuration 2208-2 of the accuracy adjusting unit 2208, the number of dimensions can be modified by having a feature vector expanding unit 2312 consolidate values of a plurality of dimensions.

The feature vector expanding unit 2312 can expand a feature vector by generating a dimension in a greater scale (expanded divided area) using a feature vector outputted from the sub-area feature vector generating unit 1114. Moreover, the feature vector expanding unit 2312 can expand a feature vector using information regarding only a feature vector outputted from the sub-area feature vector generating unit 1114. Therefore, since it is not necessary to return to an original image and perform feature extraction in order to expand a feature vector, a processing time for expanding a feature vector is significantly short compared to a processing time for generating a feature vector from the original image. For example, the feature vector expanding unit 2312 may generate a new gradient direction histogram by compositing gradient direction histograms of adjacent sub-areas.

Figure 23C:
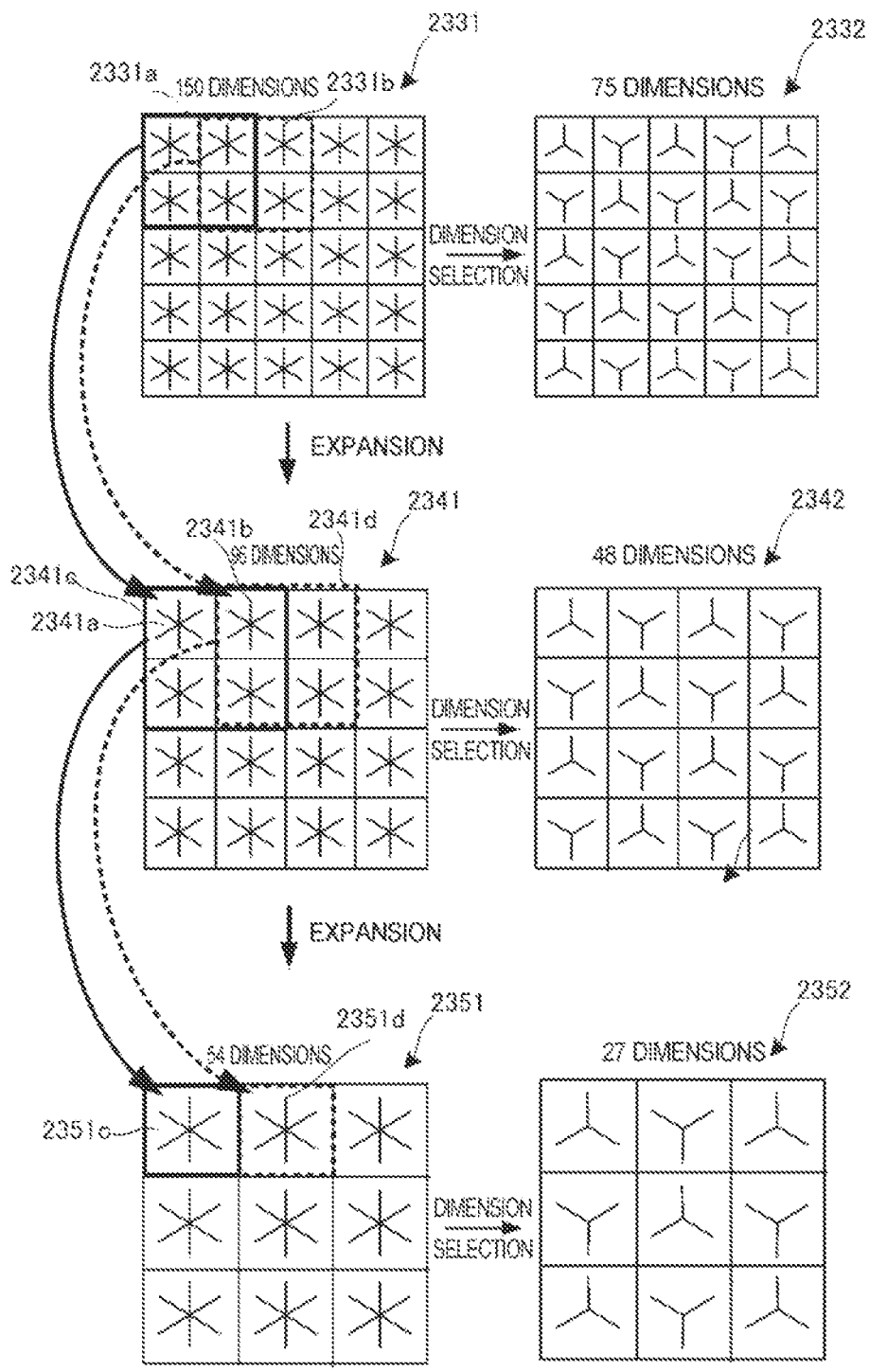
FIG. 23C is a diagram illustrating processing by the second configuration of the accuracy adjusting unit according to the third embodiment of the present invention.

FIG. 23C is a diagram showing a process performed by the second configuration 2208-2 of the accuracy adjusting unit 2208 according to the present embodiment. In FIG. 23C, by adopting respective blocks that are expansions of a total sum of gradient histograms of 2×2=4 blocks, the number of dimensions can be modified while improving accuracy.

As shown in FIG. 23C, for example, by expanding a gradient direction histogram 2331 of 5×5×6 dimensions (150 dimensions), the feature vector expanding unit 2312 can generate a gradient direction histogram 2341 of 4×4×6 dimensions (96 dimensions). In other words, the four blocks 2331a enclosed by a solid line are consolidated into one block 2341a. In addition, the four blocks 2331b enclosed by a solid dashed line are consolidated into one block 2341b.

In a similar manner, by obtaining a total sum of gradient direction histograms of 3×3 adjacent blocks among a gradient direction histogram 2341 of 5×5×6 dimensions (150 dimensions), the feature vector expanding unit 2312 can also generate a gradient direction histogram 2351 of 3×3×6 dimensions (54 dimensions). In other words, the four blocks 2341c enclosed by a solid line are consolidated into one block 2351b. In addition, the four blocks 2341d enclosed by a solid dashed line are consolidated into one block 2351d.

Moreover, when the dimension selecting unit 1115 performs dimension selection from the gradient direction histogram 2331 of 5×5×6 dimensions (150 dimensions) to a gradient direction histogram 2332 of 5×5×3 dimensions (75 dimensions), the gradient direction histogram 2341 of 4×4×6 dimensions (96 dimensions) becomes a gradient direction histogram 2342 of 4×4×6 dimensions (96 dimensions). In addition, the gradient direction histogram 2351 of 3×3×6 dimensions (54 dimensions) becomes a gradient direction histogram 2352 of 3×3×3 dimensions (27 dimensions).

Third Configuration

Figure 24:
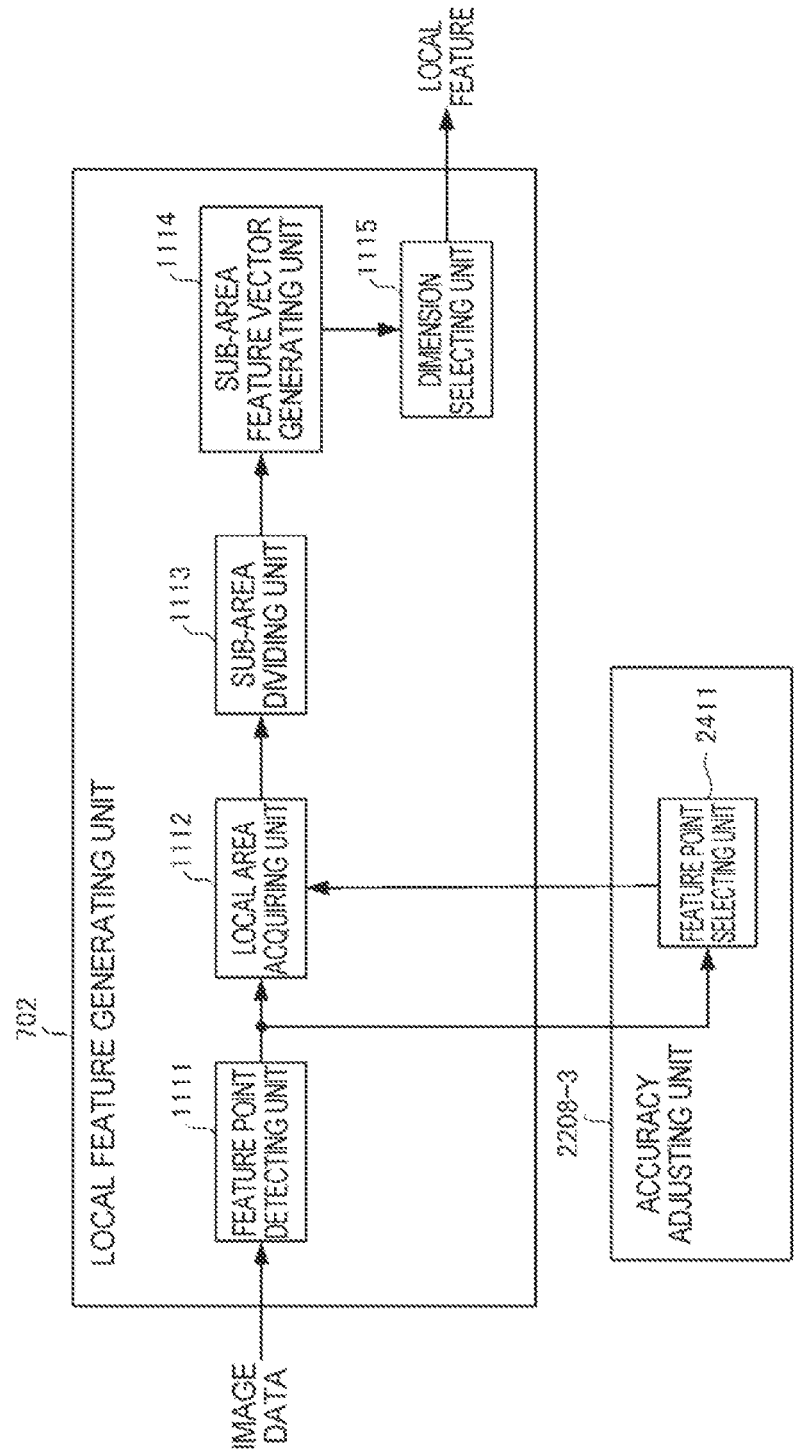
FIG. 24 is a block diagram showing a third configuration of the accuracy adjusting unit according to the third embodiment of the present invention.

FIG. 24 is a block diagram showing a third configuration 2208-3 of the accuracy adjusting unit 2208 according to the present embodiment. With the third configuration 2208-3 of the accuracy adjusting unit 2208, a data amount of a local feature can be modified while maintaining accuracy by having the feature point selecting unit 2411 modify the number of feature points when performing feature point selection.

For example, the feature point selecting unit 2411 can hold, in advance, specified number information that indicates a "specified number" of feature points to be selected. In addition, the specified number information may be information indicating a specified number itself or information indicating a total size (for example, the number of bytes) of a local feature of an image. When the specified number information is information indicating a total size of a local feature in an image, for example, the feature point selecting unit 2411 can calculate a specified number by dividing the total size by a size of a local feature at one feature point. The feature point selecting unit 2411 can randomly assign importance to all feature points and select feature points in a descending order of importance. In addition, once a specified number of feature points are selected, the feature point selecting unit 2411 can output information regarding the selected feature points as a selection result. Furthermore, based on feature point information, the feature point selecting unit 2411 can select only feature points included in a particular scale area among the scales of all feature points. In addition, when the number of selected feature points is larger than the specified number, for example, the feature point selecting unit 2411 may reduce the feature points down to the specified number based on importance and output information related to the selected feature points as a selection result.

Fourth Configuration

Figure 25:
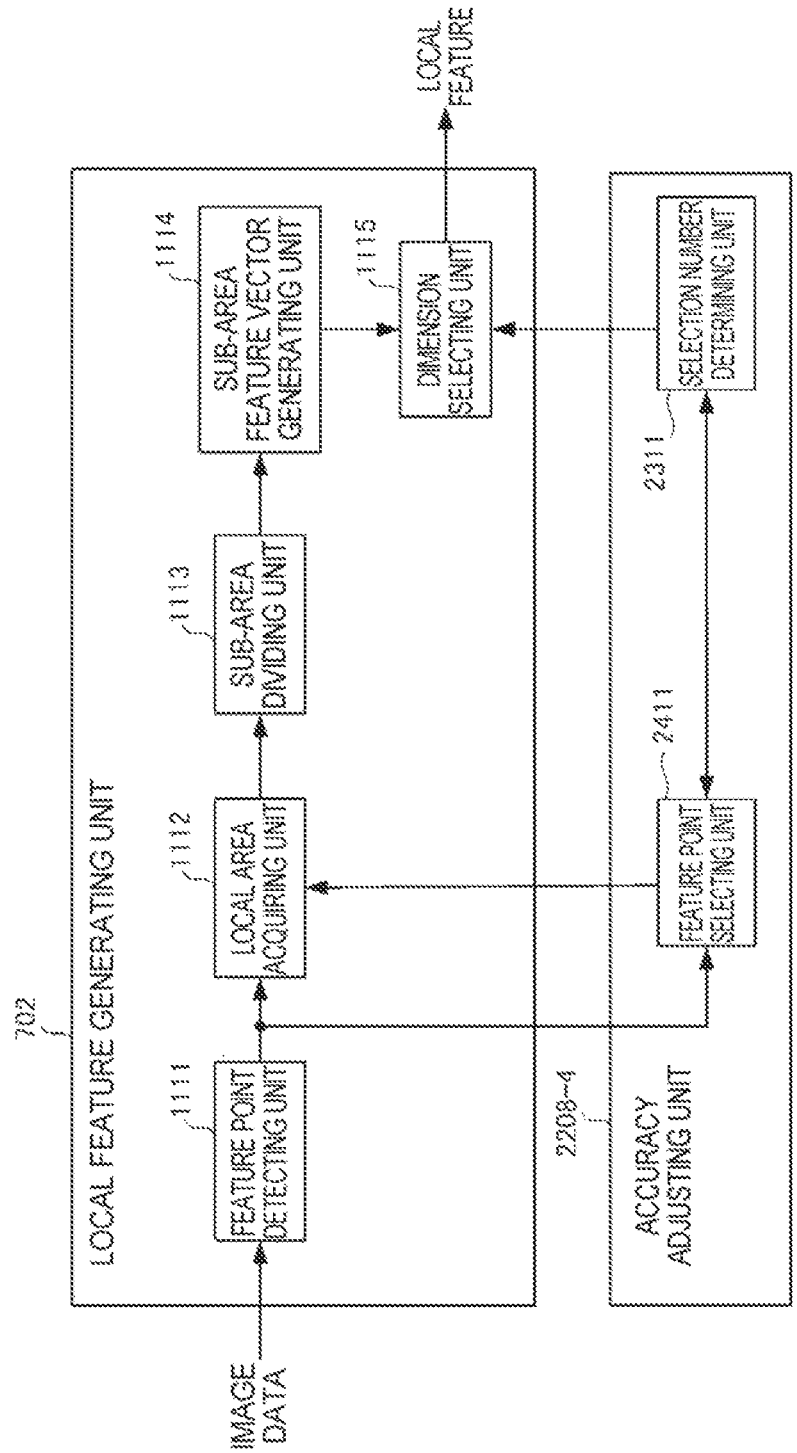
FIG. 25 is a block diagram showing a fourth configuration of the accuracy adjusting unit according to the third embodiment of the present invention.

FIG. 25 is a block diagram showing a fourth configuration 2208-4 of the accuracy adjusting unit 2208 according to the present embodiment. With the fourth configuration 2208-4 of the accuracy adjusting unit 2208, the dimension number determining unit 2311 and the feature point selecting unit 2411 cooperate with one another to modify a data amount of a local feature while maintaining accuracy.

Various relationships of the dimension number determining unit 2311 and the feature point selecting unit 2411 are conceivable in the fourth configuration 2208-4. For example, the feature point selecting unit 2411 may select feature points based on the number of feature points determined by the dimension number determining unit 2311. Alternatively, based on the specified feature size and the determined number of feature points selected by the feature point selecting unit 2411, the dimension number determining unit 2311 can determine the number of selected dimensions so that a feature size equals the specified feature size. In addition, the feature point selecting unit 2411 selects feature points based on feature point information outputted from the feature point detecting unit 1111. In addition, the feature point selecting unit 2411 can output importance information indicating an importance of each selected feature point to the dimension number determining unit 2311, and the dimension number determining unit 2311 can determine the number of dimensions to be selected by the dimension selecting unit 1115 for each feature point Accuracy Parameter FIG. 26 is a diagram showing a configuration of the accuracy parameter 2208*a* according to the present embodiment.

As a feature point parameter 2601, the accuracy parameter 2208*a* stores the number of feature points, a feature point selection threshold for selection as a feature point or not, and the like. In addition, as a local area parameter 2602, the accuracy parameter 2208*a* stores an area (size) corresponding to a Gaussian window, a shape representing a rectangle, a circle, or the like, and the like. Furthermore, as a sub-area parameter 2603, the accuracy parameter 2208*a* stores the number of divisions of a local area, a shape, and the like. In addition, as a feature vector parameter 2604, the accuracy parameter 2208*a* stores the number of directions (for example, eight directions or six directions), the number of dimensions, a dimension selection method, and the like.

Figure 26:
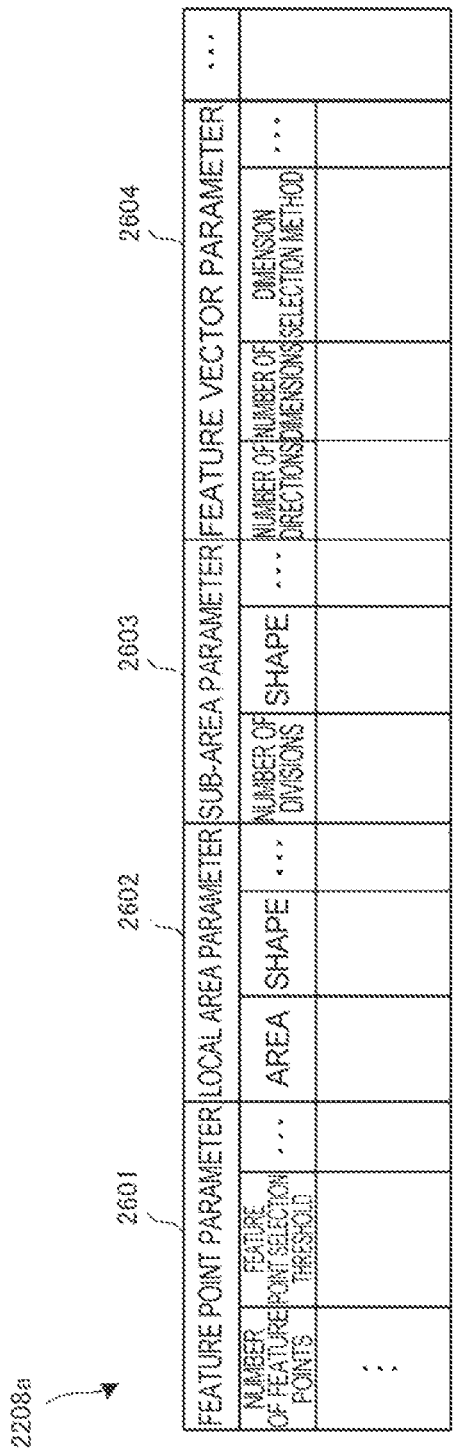
FIG. 26 is a diagram showing a configuration of an accuracy parameter according to the third embodiment of the present invention.

Moreover, the accuracy parameter shown in FIG. 26 is simply an example and is not restrictive.

Functional Configuration of Hospital Computer

Figure 27:
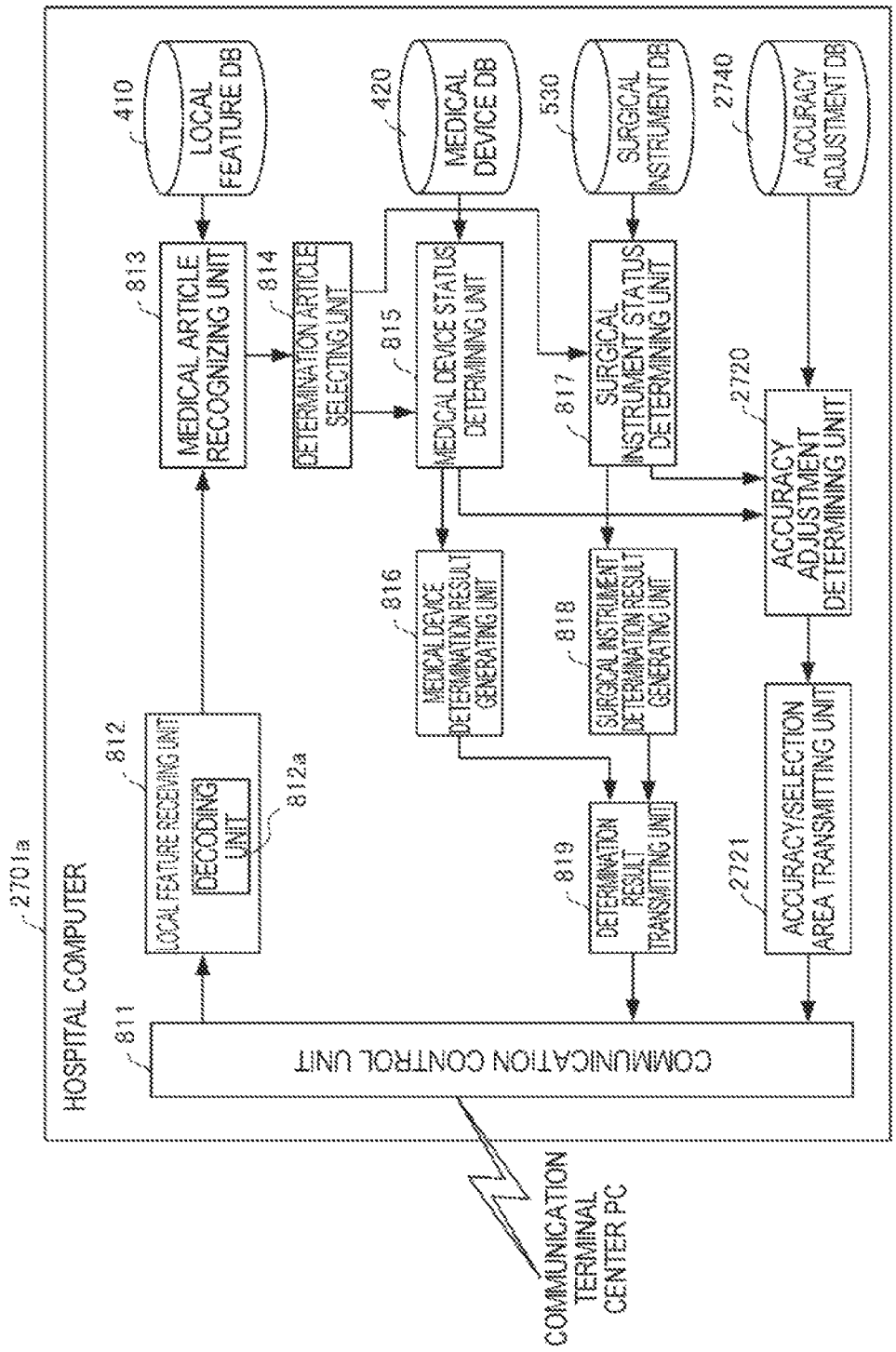
FIG. 27 is a block diagram showing a functional configuration of a hospital computer according to the third embodiment of the present invention.

FIG. 27 is a block diagram showing a functional configuration of a hospital computer 2701*a* according to the present embodiment. Moreover, functional configurations similar to FIG. 8 according to the second embodiment will be denoted by same reference characters and descriptions thereof will be omitted.

Upon receiving a determination by the medical device status determining unit 815 or the surgical instrument status determining unit 817, an accuracy adjustment determining unit 2720 references an accuracy adjustment DB 2740 (refer to FIG. 28) to adjust accuracy and determines accuracy at which a local feature is to be generated once again. An accuracy/selection area transmitting unit 2721 transmits area information of a medical device or a surgical instrument that is an object and the determined accuracy parameter to a communication terminal via the communication control unit 811.

Accuracy Adjustment DB

FIG. 28 is a diagram showing a configuration of the accuracy adjustment DB 2740 according to the present embodiment. A configuration of the accuracy adjustment DB 2740 is not limited to that shown in FIG. 28.

A first adjustment value 2803, a second adjustment value 2804, and the like for generating the accuracy parameter 2208*a* shown in FIG. 26 are stored in association with a medical article ID 2801 and a name/type 2802. Any adjustment value may be used depending on a parameter type. Since these parameters are interrelated, a parameter that is suitable for a medical article that is an object of recognition and determination is desirably selected. To this end, alternatively, a parameter may be generated and stored in advance or learned and retained in advance in accordance with a medical article that is an object.

Fourth Embodiment

Next, an information processing system according to a fourth embodiment of the present invention will be described. The information processing system according to the present embodiment differs from those of the second and third embodiments described above in that a communication terminal includes a communication terminal local feature DB and that a medical article recognizing process is shared by the communication terminal and a hospital computer. Since other configurations and operations are similar to those of the second and third embodiments, same configurations and operations will be denoted by same reference characters and detailed descriptions thereof will be omitted.

According to the present embodiment, when a recognizing process of a medical article by a communication terminal is sufficient, a local feature need not be sent from the communication terminal to a hospital computer. Therefore, traffic between the communication terminal and the hospital computer can be reduced and, at the same time, processing load on the hospital computer can be reduced.

Operational Procedure of Information Processing System

Figure 29:
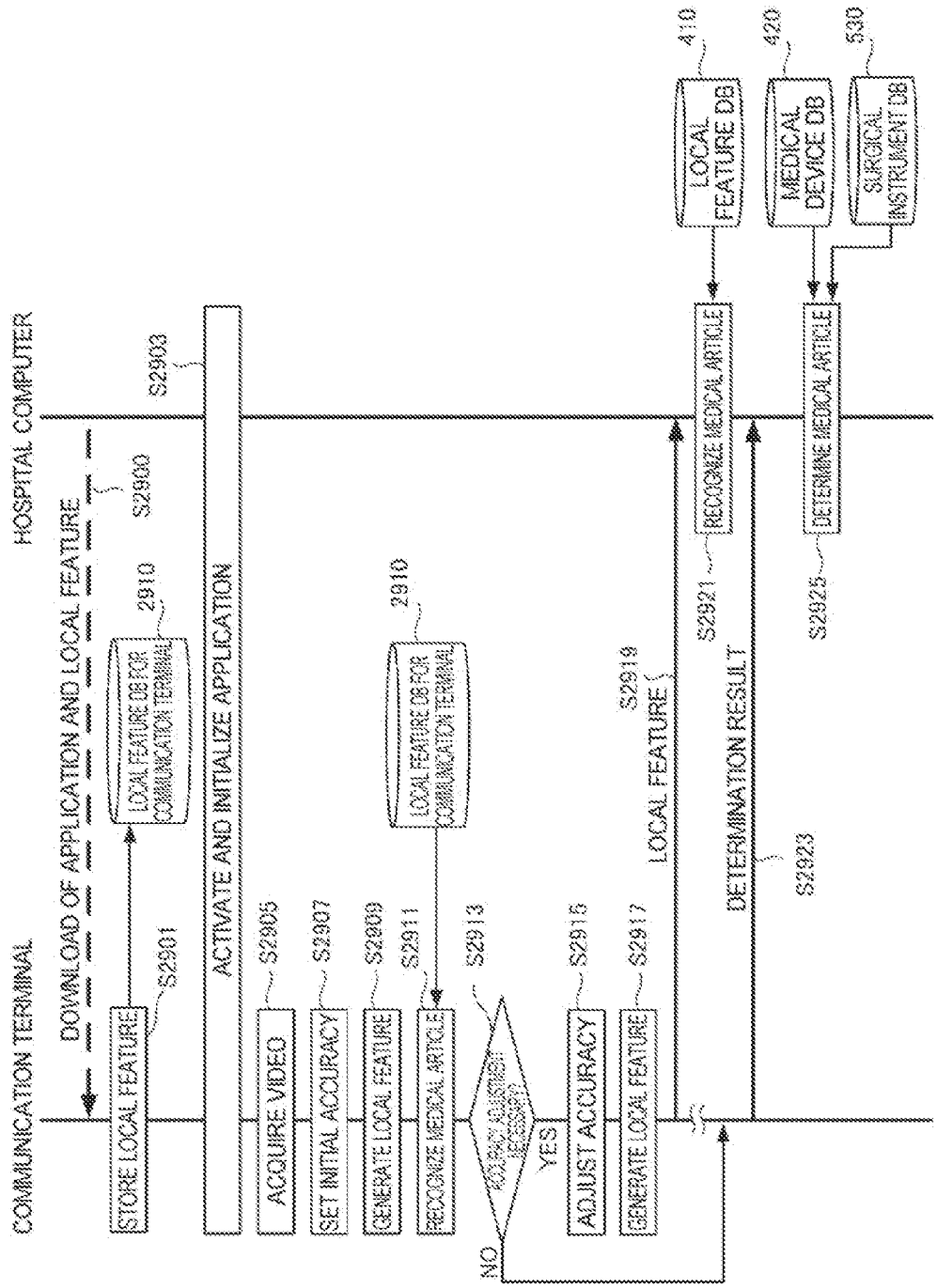
FIG. 29 is a sequence diagram showing an operational procedure of an information processing system according to a fourth embodiment of the present invention.

FIG. 29 is a sequence diagram showing an operational procedure of the information processing system according to the present embodiment. Moreover, while recognizing and determining processes of a medical article at a hospital will be representatively described in FIG. 29, processes at a pharmacy can also be realized by a similar procedure. In addition, while a center PC is not illustrated in FIG. 29, a center PC receives and informs a determination result in a similar manner to sequence diagrams described earlier.

First, if necessary, in step S2900, an application and a local feature for a communication terminal are downloaded from the hospital computer 201a to a communication terminal. At the communication terminal, in step S2901, received local features are respectively associated with medical articles and stored in a communication terminal local feature DB 2910. In addition, in step S2903, the application is activated and initialized in order to perform processes of the present embodiment.

In step S2905, the communication terminal captures and acquires a video. Next, in step S2907, an initial accuracy of local feature generation is set. In step S2909, a local feature is generated at the initial accuracy from the acquired video. In step S2911, recognition of a medical article in the video is performed by referencing the communication terminal local feature DB 2910.

In step S2913, a determination is made on whether the medical article recognition performed in step S2911 has sufficient reliability (whether accuracy adjustment is necessary). In other words, if the reliability is not sufficient, a local feature is generated by adjusting the accuracy and medical article recognition at high accuracy is performed by the hospital computer. Therefore, if the medical article recognition performed in step S2911 does not have sufficient reliability, the accuracy is adjusted in step S2915. In addition, in step S2917, a local feature with high accuracy is generated and, in step S2919, the local feature is transmitted to the hospital computer.

In step S2921, the hospital computer references the local feature DB 410 that stores local features with high accuracy and recognizes the medical article in the video.

On the other hand, if the medical article recognition performed in step S2911 has sufficient reliability, the procedure advances to step S2923 to transmit a determination result to the hospital computer.

According to the recognition result of the medical article, in step S2925, the hospital computer references the medical device DB 420 or the surgical instrument DB 530 and performs a determination of the medical article.

As described above, if recognition by the communication terminal is sufficient, determination of an arrangement, the number, and the like can be performed by simply transmitting a determination result (a medical article ID and a position) from the communication terminal to the hospital computer.

Fifth Embodiment

Next, an information processing system according to a fifth embodiment of the present invention will be described. The information processing system according to the present embodiment differs from the second to fourth embodiments described above in that a communication terminal independently performs recognition and determination of a medical article. Since other configurations and operations are similar to those of the second to fourth embodiments, same configurations and operations will be denoted by same reference characters and detailed descriptions thereof will be omitted.

According to the present embodiment, only a determination result is to be sent from a communication terminal to a hospital computer. As a result, traffic between the communication terminal and the hospital computer can be significantly reduced and, at the same time, processing load on the hospital computer can be further reduced.

Functional Configuration of Communication Terminal

Figure 30:
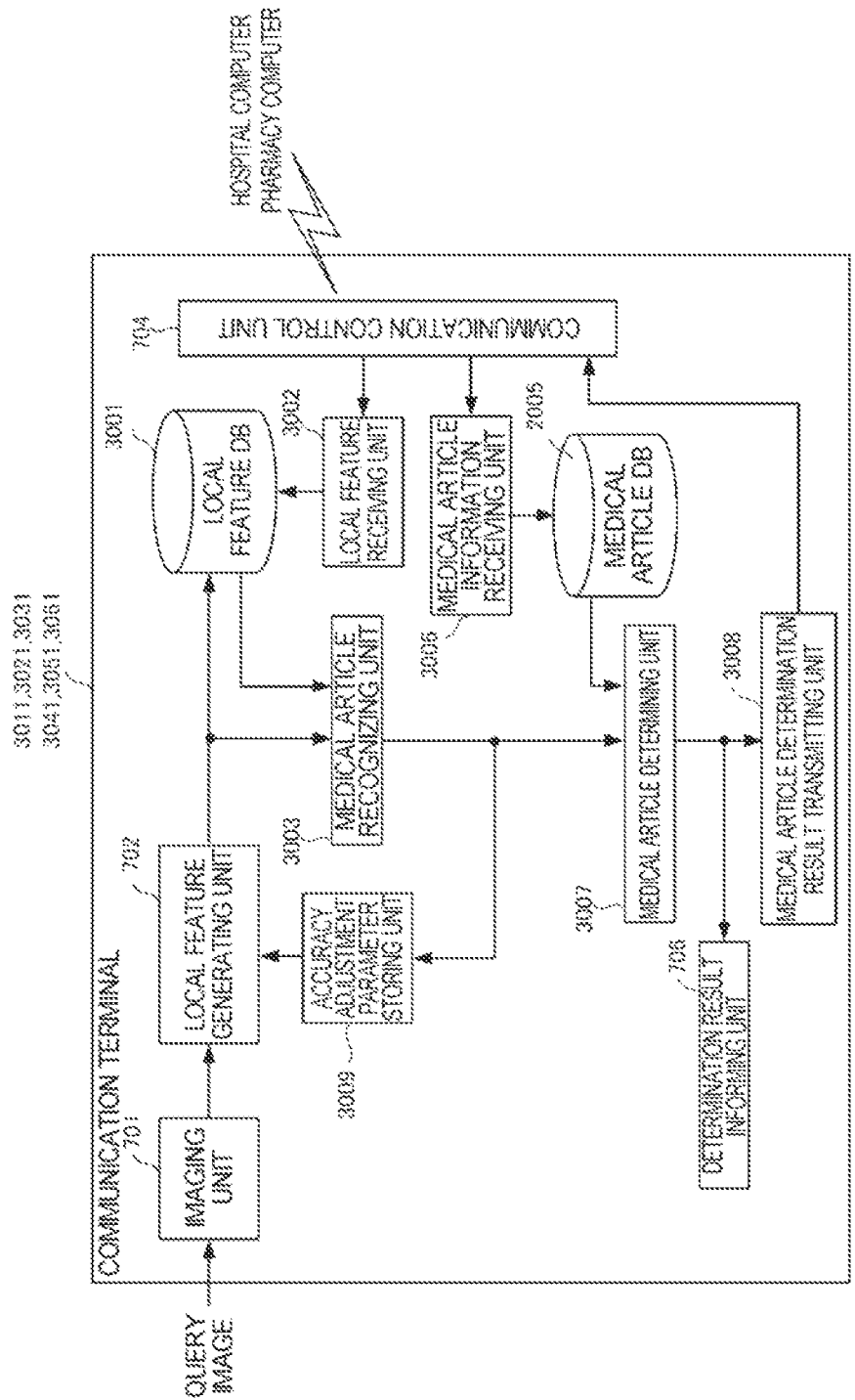
FIG. 30 is a block diagram showing a functional configuration of a communication terminal according to a fifth embodiment of the present invention.

FIG. 30 is a block diagram showing a functional configuration of the communication terminals 3011 to 3061 according to the present embodiment. Moreover, functional constituents similar to FIG. 7 according to the second embodiment will be denoted by same reference characters and descriptions thereof will be omitted.

A local feature DB 3001 stores local features downloaded by a local feature receiving unit 3002 from a hospital computer or a pharmacy computer via the communication control unit 704. Moreover, as learning, local features generated by the local feature generating unit 702 of the communication terminal may be accumulated in association with recognition results in the local feature DB 3001. A medical article recognizing unit 3003 collates a local feature generated by the local feature generating unit 702 with local features in the local feature DB 3001 and recognizes a medical article.

In addition, a local feature DB 2005 stores local features downloaded by a medical article information receiving unit 3006 from a hospital computer or a pharmacy computer via the communication control unit 704. The medical article information may include the medical device DB 420, the surgical instrument DB 530, the prescription DB 620, or the like.

A medical article determining unit 3007 references the medical article DB 2005 based on a recognition result obtained from the medical article recognizing unit 3003 and determines a medical article. The determination includes determinations of an arrangement and the number of the medical article or a mistake or defect of the medical article. The determination result is informed by the determination result informing unit 706 and, at the same time, transmitted to a hospital computer or a pharmacy computer by a medical article determination result transmitting unit 3008 via the communication control unit 704.

Furthermore, an accuracy adjustment parameter storing unit 3009 can be provided to adjust accuracy of the local feature generating unit 702 in accordance with the recognition result obtained from the medical article recognizing unit 3003.

Other Embodiments

While the present invention has been described with reference to embodiments, the present invention is not intended to be limited to the embodiments described above. Various modifications to configurations and details of the present invention will occur to those skilled in the art without departing from the scope of the present invention. In addition, systems or apparatuses that combine different characteristics included in the respective embodiments in any way are also included in the scope of the present invention.

Furthermore, the present invention may be applied to a system constituted by a plurality of devices or to a single apparatus. In addition, the present invention can also be applied to cases where a control program that realizes functions of the embodiments is directly or remotely supplied to a system or an apparatus. Accordingly, a control program to be installed in a computer, a medium storing the control program, and a WWW (World Wide Web) that enables the control program to be downloaded for the purpose of realizing functions of the present invention using a computer are also included in the scope of the present invention.

The present application claims priority on the basis of Japanese Patent Application No. 2012-017383 filed on Jan. 30, 2012, the entire contents of which are incorporated herein by reference.

A part of or all of the present embodiment may also be described as, but not limited to, the supplementary notes provided below.

(Supplementary Note 1)

An information processing system, including:

first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article;

second local feature generating unit that extracts n-number of feature points from an image of a video captured by imaging unit, and that generates n-number of second local features respectively constituted by a feature vector of 1 dimension to j dimensions for n-number of local areas including each of the n-number of feature points; and recognizing unit that selects a smaller number of dimensions among the number of dimensions i of the feature vector of the first local feature and the number of dimensions j of the feature vector of the second local feature, and that recognizes that the medical article exists in the image in the video when determining that a prescribed ratio or more of the m-number of first local features constituted by a feature vector up to the selected number of dimensions corresponds to the n-number of second local features constituted by a feature vector up to the selected number of dimensions.

(Supplementary Note 2)

The information processing system according to Supplementary note 1, further including informing unit that informs a recognition result obtained from the recognizing unit.

(Supplementary Note 3)

The information processing system according to Supplementary note 2, including a communication terminal carried by a user, and an information processing apparatus that communicates with the communication terminal, wherein the communication terminal includes the imaging unit, the second local feature generating unit, and the informing unit, and the m-number of second local features are transmitted from the communication terminal to the information processing apparatus, and the information processing apparatus includes the first local feature storing unit and the recognizing unit, and the recognition result obtained from the recognizing unit is transmitted from the information processing apparatus to the communication terminal.

(Supplementary Note 4)

The information processing system according to any one of Appendices 1 to 3, wherein the first local feature storing unit stores the m-number of first local features generated from images of a plurality of medical articles in association with each of the medical articles, and the recognizing unit recognizes a plurality of medical articles included in the image captured by the imaging unit, and includes arrangement determining unit that determines an arrangement of the plurality of medical articles in the image captured by the imaging unit based on an alignment of the n-number of second local features.

(Supplementary Note 5)

The information processing system according to Supplementary note 4, wherein the medical article is a medical device and an image captured by the imaging unit is of an examination room, a hospital room, or an operation room, the arrangement determining unit recognizes an arrangement of the medical device in the examination room, the hospital room, or the operation room, the second local feature generating unit includes accuracy adjusting unit that adjusts accuracy of the second local feature, and the recognizing unit further recognizes a mistake, a defect, or a state of the medical device based on a second local feature generated by the second local feature generating unit by adjusting to a higher accuracy.

(Supplementary Note 6)

The information processing system according to Supplementary note 4, wherein the medical article is a medical instrument and an image captured by the imaging unit is of a tray on which the medical instrument is arranged, the arrangement determining unit recognizes an arrangement of the medical instrument on the tray, the second local feature generating unit includes accuracy adjusting unit that adjusts accuracy of the second local feature, and the recognizing unit further recognizes a mistake, a defect, or a state of the medical instrument based on a second local feature generated by the second local feature generating unit by adjusting to a higher accuracy.

(Supplementary Note 7)

The information processing system according to Supplementary note 4, wherein the medical article is a pharmaceutical product and an image captured by the imaging unit is of a medicine shelf or a medicine tray, the arrangement determining unit recognizes an arrangement of the pharmaceutical product on the medicine shelf or the medicine tray, the second local feature generating unit includes accuracy adjusting unit that adjusts accuracy of the second local feature, and the recognizing unit further recognizes a mistake, a defect, or a state of the pharmaceutical product based on a second local feature generated by the second local feature generating unit by adjusting to a higher accuracy.

(Supplementary Note 8)

The information processing system according to Supplementary note 7, further including managing unit that performs inventory based on an arrangement of the plurality of pharmaceutical products recognized by the arrangement determining unit.

(Supplementary Note 9)

The information processing system according to any one of Appendices 1 to 8, wherein the first local feature and the second local feature are each generated by dividing a local area including a feature point extracted from an image into a plurality of sub-areas and generating a feature vector of a plurality of dimensions constituted by a histogram in a gradient direction in the plurality of sub-areas.

(Supplementary Note 10)

The information processing system according to Supplementary note 9, wherein the first local feature and the second local feature are each generated by selecting a dimension at which a correlation between adjacent sub-areas is lower among the generated feature vector of a plurality of dimensions.

(Supplementary Note 11)

The information processing system according to Supplementary note 9 or 10, wherein the plurality of dimensions of the feature vector are arranged to circle the local area once for every predetermined number of dimensions so that dimensions can be selected starting from a first dimension in a descending order of contributions to the feature point and in accordance with an increase in accuracy that is required with respect to the local feature.

(Supplementary Note 12)

The information processing system according to Supplementary note 11, wherein the second local feature generating unit generates the second local feature corresponding to a correlation of the medical articles so that the second local feature with a larger number of dimensions is generated for a medical article that has a higher correlation with another medical article.

(Supplementary Note 13)

The information processing system according to Supplementary note 11 or 12, wherein the first local feature storing unit stores the first local feature corresponding to a correlation of the medical articles so that the first local feature with a larger number of dimensions is stored for a medical article that has a higher correlation with another medical article.

(Supplementary Note 14)

An information processing method in an information processing system including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the method including the steps of:

extracting n-number of feature points from an image in a captured video and generating n-number of second local features respectively constituted by a feature vector of 1 dimension to j dimensions for n-number of local areas including each of the n-number of feature points; and selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions.

(Supplementary Note 15)

A communication terminal, including:

second local feature generating unit that extracts n-number of feature points from an image of a video captured by imaging unit, and that generates n-number of second local features respectively constituted by a feature vector of 1 dimension to j dimensions for n-number of local areas including each of the n-number of feature points;

first transmitting unit that transmits the m-number of second local features to an information processing apparatus that recognizes a medical article included in the captured image based on a collation of local features; and first receiving unit that receives information indicating a medical article included in the captured image from the information processing apparatus.

(Supplementary Note 16)

A communication terminal control method including the steps of:

extracting n-number of feature points from an image of a video captured by imaging unit and generating n-number of second local features respectively constituted by a feature vector of 1 dimension to j dimensions for n-number of local areas including each of the n-number of feature points;

transmitting the m-number of second local features to an information processing apparatus that recognizes a medical article included in the captured image based on a collation of local features; and receiving information indicating a medical article included in the captured image from the information processing apparatus.

(Supplementary Note 17)

A control program that causes a computer to execute the steps of:

extracting n-number of feature points from an image of a video captured by imaging unit and generating n-number of second local features respectively constituted by a feature vector of 1 dimension to j dimensions for n-number of local areas including each of the n-number of feature points;

transmitting the m-number of second local features to an information processing apparatus that recognizes a medical article included in the captured image based on a collation of local features; and receiving information indicating a medical article included in the captured image from the information processing apparatus.

(Supplementary Note 18)

An information processing apparatus, including:

first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article;

second receiving unit that extracts n-number of feature points from an image of a video captured by a communication terminal and that receives, from the communication terminal, n-number of second local features respectively constituted by a feature vector of 1 dimension to j dimensions for n-number of local areas including each of the n-number of feature points;

recognizing unit that selects a smaller number of dimensions among the number of dimensions i of the feature vector of the first local feature and the number of dimensions j of the feature vector of the second local feature, and that recognizes that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and second transmitting unit that transmits information indicating the recognized medical article to the communication terminal.

(Supplementary Note 19)

A control method of an information processing apparatus including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the method including the steps of:

extracting n-number of feature points from an image of a video captured by a communication terminal and receiving, from the communication terminal, n-number of second local features respectively constituted by a feature vector of 1 dimension to j dimensions for n-number of local areas including each of the n-number of feature points;

selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and transmitting information indicating the recognized medical article to the communication terminal.

(Supplementary Note 20)

A control program of an information processing apparatus including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the program causing a computer to execute the steps of:

extracting n-number of feature points from an image of a video captured by a communication terminal and receiving, from the communication terminal, n-number of second local features respectively constituted by a feature vector of 1 dimension to j dimensions for n-number of local areas including each of the n-number of feature points;

selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and transmitting information indicating the recognized medical article to the communication terminal.

We claim:

1. An information processing system, comprising:
   first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article;
   second local feature generating unit that extracts n-number of feature points from an image of a video captured by imaging unit, and that generates n-number of second local features respectively constituted by a feature vector of 1 dimension to j dimensions for n-number of local areas including each of the n-number of feature points; and
   recognizing unit that selects a smaller number of dimensions among the number of dimensions i of the feature vector of the first local feature and the number of dimensions j of the feature vector of the second local feature, and that recognizes that the medical article exists in the image in the video when determining that a prescribed ratio or more of the m-number of first local features constituted by a feature vector up to the selected number of dimensions corresponds to the n-number of second local features constituted by a feature vector up to the selected number of dimensions.

2. The information processing system according to claim 1, further comprising informing unit that informs a recognition result obtained from the recognizing unit.

3. The information processing system according to claim 2, comprising a communication terminal carried by a user, and an information processing apparatus that communicates with the communication terminal, wherein
   the communication terminal includes the imaging unit, the second local feature generating unit, and the informing unit, and the n-number of second local features are transmitted from the communication terminal to the information processing apparatus, and
   the information processing apparatus includes the first local feature storing unit and the recognizing unit, and the recognition result obtained from the recognizing unit is transmitted from the information processing apparatus to the communication terminal.

4. The information processing system according to claim 1, wherein
   the first local feature storing unit stores the m-number of first local features generated from images of a plurality of medical articles in association with each of the medical articles, and
   the recognizing unit recognizes a plurality of medical articles included in the image captured by the imaging unit, and includes arrangement determining unit that determines an arrangement of the plurality of medical articles in the image captured by the imaging unit based on an alignment of the n-number of second local features.

5. The information processing system according to claim 4, wherein
   the medical article is a medical device and an image captured by the imaging unit is of an examination room, a hospital room, or an operation room,
   the arrangement determining unit recognizes an arrangement of the medical device in the examination room, the hospital room, or the operation room,
   the second local feature generating unit includes accuracy adjusting unit that adjusts accuracy of the second local feature, and
   the recognizing unit further recognizes a mistake, a defect, or a state of the medical device based on a second local feature generated by the second local feature generating unit by adjusting to a higher accuracy.

6. The information processing system according to claim 4, wherein
   the medical article is a medical instrument and an image captured by the imaging unit is of a tray on which the medical instrument is arranged,
   the arrangement determining unit recognizes an arrangement of the medical instrument on the tray,
   the second local feature generating unit includes accuracy adjusting unit that adjusts accuracy of the second local feature, and
   the recognizing unit further recognizes a mistake, a defect, or a state of the medical instrument based on a second local feature generated by the second local feature generating unit by adjusting to a higher accuracy.

7. The information processing system according to claim 4, wherein the medical article is a pharmaceutical product and an image captured by the imaging unit is of a medicine shelf or a medicine tray, the arrangement determining unit recognizes an arrangement of the pharmaceutical product on the medicine shelf or the medicine tray, the second local feature generating unit includes accuracy adjusting unit that adjusts accuracy of the second local feature, and the recognizing unit further recognizes a mistake, a defect, or a state of the pharmaceutical product based on a second local feature generated by the second local feature generating unit by adjusting to a higher accuracy.

8. The information processing system according to claim 7, further comprising managing unit that performs inventory based on an arrangement of the plurality of pharmaceutical products recognized by the arrangement determining unit.

9. The information processing system according to claim 1, wherein the first local feature and the second local feature are each generated by dividing a local area including a feature point extracted from an image into a plurality of sub-areas and generating a feature vector of a plurality of dimensions constituted by a histogram in a gradient direction in the plurality of sub-areas.

10. The information processing system according to claim 9, wherein the first local feature and the second local feature are each generated by selecting a dimension at which a correlation between adjacent sub-areas is lower among the generated feature vector of a plurality of dimensions.

11. The information processing system according to claim 9, wherein the plurality of dimensions of the feature vector are arranged to circle the local area once for every predetermined number of dimensions so that dimensions can be selected starting from a first dimension in a descending order of contributions to the feature point and in accordance with an increase in accuracy that is required with respect to the local feature.

12. The information processing system according to claim 11, wherein the second local feature generating unit generates the second local feature corresponding to a correlation of the medical articles so that the second local feature with a larger number of dimensions is generated for a medical article that has a higher correlation with another medical article.

13. The information processing system according to claim 11, wherein the first local feature storing unit stores the first local feature corresponding to a correlation of the medical articles so that the first local feature with a larger number of dimensions is stored for a medical article that has a higher correlation with another medical article.

14. An information processing method in an information processing system including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the method comprising the steps of:

extracting n-number of feature points from an image in a captured video and generating n-number of second local features respectively constituted by a feature vector of 1 dimension to j dimensions for n-number of local areas including each of the n-number of feature points; and selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions.

15. An information processing apparatus, comprising:

first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article;

second receiving unit that extracts n-number of feature points from an image of a video captured by a communication terminal and that receives, from the communication terminal, n-number of second local features respectively constituted by a feature vector of 1 dimension to j dimensions for n-number of local areas including each of the n-number of feature points;

recognizing unit that selects a smaller number of dimensions among the number of dimensions i of the feature vector of the first local feature and the number of dimensions j of the feature vector of the second local feature, and that recognizes that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and second transmitting unit that transmits information indicating the recognized medical article to the communication terminal.

16. A control method of an information processing apparatus including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the method comprising the steps of:

extracting n-number of feature points from an image of a video captured by a communication terminal and receiving, from the communication terminal, n-number of second local features respectively constituted by a feature vector of 1 dimension to j dimensions for n-number of local areas including each of the n-number of feature points;

selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and transmitting information indicating the recognized medical article to the communication terminal.

17. A non-transitory computer-readable storage medium with a control program of an information processing apparatus including first local feature storing unit that stores, in association with each other, a medical article and m-number of first local features which are respectively constituted by a feature vector of 1 dimension to i dimensions and which are generated for each of m-number of local areas including each of m-number of feature points in an image of the medical article, the program causing a computer to execute the steps of:

extracting n-number of feature points from an image of a video captured by a communication terminal and receiving, from the communication terminal, n-number of second local features respectively constituted by a feature vector of 1 dimension to j dimensions for n-number of local areas including each of the n-number of feature points;

selecting a smaller number of dimensions among the number of dimensions i of the feature vector of the first local feature and the number of dimensions j of the feature vector of the second local feature, and recognizing that the medical article exists in the image in the video when determining that a prescribed ratio or more of the m-number of first local features constituted by a feature vector up to the selected number of dimensions corresponds to the n-number of second local features constituted by a feature vector up to the selected number of dimensions; and transmitting information indicating the recognized medical article to the communication terminal.

* * * * *